United States Patent [19]
Zhou et al.

[11] Patent Number: 5,814,479
[45] Date of Patent: Sep. 29, 1998

[54] BSK RECEPTOR-LIKE TYROSINE KINASE

[75] Inventors: Renping Zhou, Piscataway, N.J.;
Nicholas T. Schulz, Pittsburg, Pa.;
Lawrence F. Kromer, Arlington;
George F. Vande Woude, Berryville,
both of Va.

[73] Assignee: The United States of America as represented by the Secretary of the Department of Health and Human Services, Washington, D.C.

[21] Appl. No.: 673,789

[22] Filed: Jun. 11, 1996

Related U.S. Application Data

[63] Continuation of Ser. No. 177,812, Jan. 4, 1994, abandoned.

[51] Int. Cl.$^6$ ........................... C12N 15/12; C12N 15/52
[52] U.S. Cl. ...................... 435/69.1; 435/194; 435/325; 435/348; 435/252.3; 435/254.11; 435/320.1; 536/23.5; 536/23.2; 536/24.31
[58] Field of Search ................................. 435/69.1, 194, 435/325, 348, 252.3, 254.11, 320.1; 536/23.5, 23.2, 24.31

[56] References Cited

PUBLICATIONS

Barinaga, Science, vol. 264, p. 772, 1994.
Maisonpierre, Peter C., et al.; "Ehk–1 and Ehk–2: Two Novel Members Of The Eph Receptor–Like Tyrosine Kinase Family With Distinctive And Neuronal Expression"; *Ongogene*, (1993), vol. 8, pp. 3277–3288.
Maru, Y. et al., "Evolution, Expression, and Chromosomal Location of a Novel Receptor Tyrosine Kinase Gene, eph." *Mol. and Cell Biology*, 8:3770–3776 (1988).
Sajjadi, F.G., et al., "Identification of a New eph–Related Receptor Tyrosine kinase Gene From Mouse and Chicken That is Developmentally Regulated and Encodes at Least Two Forms of the Receptor", *The New Biologist* 3:769–778 (1991).
Lindberg, R.A. and Hunter, T. "cDNA Cloning and Characterization of eck, an Epithelial Cell Receptor Protein–Tyrosine kinase in the eph/elk Family of Protein Kinases" *Mol. and Cell. Biology* 10:6316–6324 (1990).
Lhotak, V. et al., "Characterization of Elk, a Brain–Specific Receptor Tyrosine Kinase", *Mol and Cell Biology* 11:2496–2502 (1991).
Gilardi–Hebenstreit, P. et al., "An Eph–Related Receptor Protein Tyrosine Kinase Gene Segmentally Expressed in the Developing Mouse Hindbrain", *Oncogene* 7:2499–2506 (1992).
Saijadi, F.G. and Pasquale, E.B., "Five Novel Eph–related Tyrosine Kinases are Differently Expressed", *Oncogene*, 8:1807–1813 (1993).
Pasquale "Identification of Chicken Embryo Kinase 5, a Developmentally Regulated Receptor–Type Tyrosine Kinase of the Eph Family" *Cell Regulation* 2:523–534 (1991).
Chan And Watt "*Eek and Erk*, New Members of the Eph Subclass of Receptor Protein–Tyrosine Kinases" *Oncogene* 6:1057–1061 (1991).
Hirai et al., "A Novel Putative Tyrosine Kinase Receptor Ecoded by the Eph Gene" *Science* 238:1717–1720 (1987).
Wicks et al., "Molecular Cloning of Hek, the Gene Encoding a Receptor Tyrosine Kinase Expressed by Human Lymphoid Tumor Cell Lines" *Proc. Natl. Acad. Sciences* (USA) 89:1611–1615 (1992).
Nieto et al., "A Receptor Protein Tyrosine Kinase Implicated in the Segmental Patterning of the Hindbrain and Mesoderm" *Development* 116:1137–1150 (1992).

*Primary Examiner*—Stephen Walsh
*Assistant Examiner*—Sally P. Teng
*Attorney, Agent, or Firm*—Morgan & Finnegan

[57] ABSTRACT

The present invention provides a nucleic acid sequence encoding a receptor-like tyrosine kinase designated, Bsk. The Bsk receptor-like tyrosine kinase is expressed predominantly in the brain, specifically the limbic system. Also included is the receptor encoded by the Bsk nucleic acid sequence and antibodies reactive with the Bsk protein. This invention further relates to bioassays using the nucleic acid sequence, receptor protein or antibodies of this invention to diagnose, assess, or prognose a mammal afflicted with neurodegenerative disease. Therapeutic uses for the Bsk receptor-like tyrosine kinase are also provided. This invention also relates to the ligand for the Bsk receptor, and diagnostic and therapeutic uses for the Bsk ligand.

17 Claims, 19 Drawing Sheets

FIG. 2A

```
   1  AATTCGGCACGAGTGAAAGGGAACCTTCACCACCACTCCGACCCTGTGGCACTTAAAAGAAGAAGAGGGGCTGCCAGAAAAAGAAAAAGTCTTAAAGGGCAA
 121  AGAAGCGGGACTCCCGACCCTCTACGACCCTTGACCGAGCCCACCAGGACTGTACTAGCCATCACAACTTCATCTTATCCAAACTGAAAGGGAGGGCGACAGAGCCAGAAGC
 241  AAACTTCTTCAGCGTCTCTGCGGATCGTGTGAGATTCCCGACATTTAGAGAGCCAGAGGGGTAGTAGAAATGCGGGGCTCCGGGCACCCCCCCGGGCTCCGGGCACCCTTTCCACTGCCCCTTCCACCAA
 361  GCCTGAACCTTAGGCTGAGCCTGACCACCGACCAGGACGCAGAAGAGGCAGAGAGGGTAGTAGAAATGCGGGGCTCCGGGCACCCCCCCGGGCTCCGGGCACCCCAGGGCAGAGGTGGGCGGGAC
         * *          M  R  G  S  G  P  R  G  A  G  H  R  R  T  Q  G  R  G  G  G  D
   1
 481  GACACCCCCGCGTCCCTGCCTCTGCAGGCTGCTATTCGGCACCTGTCTAAAGGGCCCCTTTGCGCTTTGTGCGGGCGCTCCCGACCCTTTGGCCAGCCCAGCAAC
  22     D  T  P  R  V  P  A  S  L  A  G  C  Y  S  A  P  L  K  G  P  L  M  T  C  L  L  L  C  A  A  L  R  T  L  L  A  S  P  S  N
 601  GAAGTGAATTTGTTGGATTCGCGCACTGTCATGGGGATGGACCTTGGATTGCTTTTCCAAAGAACGGTTGGTGAAGTTGATGAGAACTGAAGAATTGTGAAGATTGTTGGAAGAGATTGGTGAAGTTGATGAGAACATGCCCCATCCACACATAC
  62     E  V  N  L  D  S  R  T  V  M  G  D  L  G  W  I  A  F  P  K  N  G  W  E  E  I  G  E  V  D  E  N  Y  A  P  I  H  T  Y
 721  CAAGTGTGCAAAGTTCACAGAAGTTATGGAACAGAATCAGAATGGCTCTAACGAAGTGCTTCCAGAATCTCTAACGAAGTGCTTCCAGAATCTTATTGAACTCAAGAATCTTTAAGGACTGCAACAGC
 102     Q  V  C  K  V  M  E  Q  N  Q  N  N  W  L  L  T  S  W  I  S  N  E  G  A  S  R  I  F  I  E  L  K  F  T  L  R  D  C  N  S
 841  CTTCCTGGAGGACTGGGACTTGTAAGGAGACATTTAACATGTATTATTTGAATCAGATGATGAATGGGAGAATGAAGTATCAAAGAGAACCAATACATCAAGATTGATACCATCGCTGCTGCA
 142     L  P  G  G  L  G  T  C  K  E  T  F  N  M  Y  Y  F  E  S  D  D  E  N  G  R  S  I  K  E  N  Q  Y  I  K  I  D  T  I  A  A
 961  GATGAGAGCTTCACAGAACTTGATCTTGGTGATAGAGTCATGAAGCTGAATACCGAAGTCCGAGATGTCGGACCTCTGAGCAAAAAGGGATTTTATCTTGCTTTCCAAGATGTCGGTGCT
 182     D  E  S  F  T  E  L  D  L  G  D  R  V  M  K  L  N  T  E  V  R  D  V  G  P  L  S  K  K  G  F  Y  L  A  F  Q  D  V  G  A
1081  TGCATTGCTCTGGTTTCTGTTCGTGTCCGTGTCTACTATAAAAGTGCCCCTCTGTAGTAAGACACTTGGCTATCTTCCCTGACACTTACTGGAGATCCAGAGATTCATCAGAGTTGTTGAGAGTGTCA
 222     C  I  A  L  V  S  V  R  V  Y  K  C  P  S  V  V  R  H  L  A  I  F  P  D  T  I  T  G  A  D  S  S  Q  L  L  E  V  S
1201  GGCTCCTGCGTCAACATTCTGTGACAGATGATCCTCCCAAGATGCATTGCAGTGCTGCTGTTCCCATTGGGAAATCATGCAAGCCTGGATATGAAGAGAAAAAT
 262     G  S  C  V  N  H  S  V  T  D  D  P  P  K  M  H  C  S  A  E  G  E  W  L  V  P  I  G  K  C  M  C  K  A  G  Y  E  E  K  N
1321  GGTACCTGCCAAGTCCCCTTCCAGTGCAAGTCCCAGTCAACAGCATTCTTTGTCTTGCAAGAGCCAGAATTGCAAAGAACACAGAAGATTGCAAAGAACACAGAAGATTGAAGATTATCCTGAGTATGCAA
 302     G  T  C  Q  A  P  S  P  V  T  N  V  K  K  G  K  I  A  K  N  S  I  S  L  S  W  Q  E  P  D  R  P  N  G  I  I  L  E  Y  E
```

FIG. 2B

```
1441  ATCAAGTACTTTGAAAAGGACCAAGAGACCAGTTACACAATTATCAGCTAAAGAGACCTAAAGAGTCTAAAGAGACCTGAAACCTGTGTATGCTCTTCCAAATTCGAGCACGT
 342    I  K  Y  F  E  K  D  Q  E  T  S  Y  T  I  I  K  S  K  E  T  S  I  T  A  E  G  L  K  P  A  S  V  V  F  Q  I  R  A  R

1561  ACAGCAGCAGGCTACGGCGTCTTCAGTCGAGATTGAGTTTGAAACACCAGTGTCAGTTGCAGCATCAAAGCCAGATTCCATCATTGCAGTGTCAGTGACAGTGGGA
 382    T  A  A  G  Y  G  V  F  S  R  R  F  E  F  E  T  P  V  S  V  A  A  S  N  D  Q  S  Q  I  P  I  I  A  V  S  V  T  V  G

1681  GTCATCTTGTTGCAGTGATGATCGGCTTCCTCCTCAGTGGCAGTTGCTGCGATTGTGGCCCATCCAAGCCTAATATGGCGGTGTGGC
 422    V  I  L  L  A  V  M  I  G  F  L  L  S  G  S  C  C  C  D  C  G  R  A  S  S  L  C  A  V  A  H  P  S  L  I  W  R  C  G

1801  TACAGCAAAGCAAAGCAGGATCCAGAAGAAGAGGAAAAGATGCACTTTCATAACGGGCACATTAAACTGCCAGGAGTCAGAACTGTCAGATCGGACACACTTATGATCGACAACTACCTGAAAGAGAATTA
 462    Y  S  K  A  K  Q  D  P  E  E  E  K  M  H  F  H  N  G  H  I  K  L  P  G  V  R  T  Y  I  D  P  H  T  Y  E  D  P  N  Q  A

1921  GTTCATGAATTTGCGAAGCAGATTGAAGCTTCATGCATCACCATTGAGAGAGTGATCGAGCAGGAATTTGGTGAAGTTTGCAGTGGATGTTTGAAACTACCTGAAAAGAGAATTA
 502    V  H  E  F  A  D  E  I  E  A  S  C  I  T  I  E  R  V  I  Ⓖ  A  Ⓖ  E  F  Ⓖ  E  V  C  S  G  C  L  K  L  P  G  K  R  E  L

2041  CCTGTGGCTATCAAAACTCTAAAGTAGGCTATACTGAAAAGCAGCAGAGATTTCCTGGGTGAAGCAAGTATTATGGGGCAGTTCGATCATCCAAACATCATCATCTAGAAGGTGTT
 542    P  V  A  I  Ⓚ  T  L  K  V  G  Y  T  E  K  Q  R  R  D  F  L  G  E  A  S  I  M  G  Q  F  D  H  P  N  I  I  H  L  E  G  V

2161  GTGACTAAAAGCAACAAACCTGTGATGATAGTGACAGAGTACATGGAAAATGGCTCCTTAGACACGTTTTTAAAGAAAAACGATGGACACTTCACTGTGATTCAGCTTGTTGGCATGCTGAGA
 582    V  T  K  S  K  P  V  M  I  V  T  E  Y  M  E  N  G  S  L  D  T  F  L  K  K  N  D  G  Q  F  T  V  I  Q  L  V  G  M  L  R

2281  GGCATCGCTGCAGGAATGAAGTACTTGTCTGACAATGGGCTACGTCACATAGACGTACTTGCTGCTAGAAACATCTTAATCAACAGTAACCTTGTGTGCAAGGTGTCTGACTTTGGACTTTCC
 622    G  I  A  A  G  M  K  Y  L  S  D  N  G  |Y  V  H  R  D  L  A  A  R  N  I  L  I  N  S  N  L  V  C  K  V  S  D  F  G  L  S

2401  AGGGTACTGGAAGATGATCCTGAGGCAGCTGCCACACACGGAGGCAATTCCAATCAGATGGACTGCCCCGGAGCAATAGCTTTTCGAAAGTTCACCTCTGCCAGTGATGTCTGG
 662    R  V  L  E  D  D  P  E  A  A  Y  T  T  R  G  G  K  I  P  I  R  W  T  A  P  E  A  I  A  F  R  K  F  T  S  A  S  D  V  W

2521  AGCCTTCAAGAGATCAAGGTCAGATGTGAAGGTGTGCCAGTGTGACCCGGCATGGTAAACGGGATGTGAACAACCTGTAAACAACCCTGAAACAACCCTGAAATTTATTT
 702    S  Y  G  I  V  M  W  E  V  V  S  Y  G  E  R  P  Y  W  E  M  T  N  Q  D  V  I  K  A  V  E  E  G  Y  R  L  P  S  P  M  D
```

FIG. 2C

```
2641 TGCCCTGCTGCTCTCTTATCAATTAATGCTGGATTGCTGGCAGAAAGATCGAAACAGCAGCCCAAGTTTGATGAAATCGTCAACATGCTGGACAAACTGATACGAAACCCAAGTAGTCTG
 742  C  P  A  A  L  Y  Q  L  M  L  D  C  W  Q  K  D  R  N  S  R  P  K  F  D  E  I  V  N  M  L  D  K  L  I  R  N  P  S  S  L

2761 AAGACACTGGTGAATGCTCGAGCAGAGTGCTCACATTGTTGCCAGAACATGTTCTTTGGGCTCTGGTGGTCTCAGATCAGTAGGTGAATGGCTGGAAGCAATCAAAATGGGTCGGTAC
 782  K  T  L  V  N  A  S  S  R  V  S  T  L  L  A  E  H  G  S  L  G  S  G  A  Y  R  S  V  G  E  W  L  E  A  I  K  M  G  R  Y

2881 ACAGAGATTTTCATGGAAAATGGATACAGTTCAATGACGCTGTGGCTCAGGTGACCTTGGAGGATTTGAGGCGCCTGGAGTGCGGTCGGTGTCACCGAAGAAGATCATGAGC
 822  T  E  I  F  M  E  N  G  Y  S  S  M  D  A  V  A  Q  V  T  L  E  D  L  R  R  L  G  V  T  L  V  G  H  Q  K  K  I  M  S

3001 AGCCTTCAAGAGATGAAGGTGCAGATGGTGTAAACCGGATGGCTGACCGGCGATGGTCTAAACTCAGCACTTTGTAAACAACCCTGAGATTTATTTT
 862  S  L  Q  E  M  K  V  Q  M  V  N  G  M  V  P  V  *

3121 AACAGAGAAAGGGGAAAGGGTGGTTCTAAACCTTTGCCTTAAGGCATTGCCCTTAATCAATATTTTACTAAAAATCTCCTGATCTTCCCTCTTAATTCCACAATGTACAG
3241 GTAACCTGCAAAGAGAGCTAACATGACGATCGATCAAATCCTTATTAAAATATGTAACGAAATCTTCCTGTACAGGAGTCTTGTACAGGAAATGTATCAAGCTAGAGCACCTTT
3361 AGAGACTGTTAAGGCAGCCCCCTTCAACCTCCAGGATCAACTTAACTGTGTGGGCTAAGAAAACTGCATTTTACTGACGTTTACTTCAAGTCTTAAT
3481 TGTCTACATGAGTGTATTGAAGAGCAATATGATTAGATTATTTTTCTGTGTGAATAGACTTTGTAATTTTAGTTGCTCTTTAGTTGTAATGAAATGCATGTTGTAAGTTATAGATAGTTATATATGTATAGTTTGCAATAT
3601 GTCAAGGAAAAGTTCAATACAGGGTGTAATTGTGTGTGCTGAAATTGTGAGGTATGTGGAGGTATTTTTTTGCCTTTGGATAGTGTTTTAAT
3721 ATGCAGGAACATACAGGAAAGTGTCTATCGAAATGTCTTCTAGACTCTATCATGGGTAAAAGAGTAGAAAGCCTAGACCAAATTGGTATCTTATGCTTATGCTCTCATTTTAAAGCAACTAATTA
3841 TTTGACGACATACAGGAAAGTGTCTTCTAGACTCTATCATGGGTAAAAGAGTAGAAAGCCCTAGACCAAATTGGTATCTTATGCTTATGCTCTCATTTTAAAGCAACTAATTA
3961 GTTCATTTAAACAGCTAATGCCTCTAGACTAAAATCTTCTAAAGCAATTTGACACAAAGGGCACACTTGTGAAGAAGAGGCACACTTGTGAAGAAGAGGCATGTTTATACTAAGACAGCATTAAAAATCCAC
4081 CTAAGTTCCTGAAAATATCTTCTAAAGCAATTTGACACCACTTCCAGCTGTGACTCATTCACAGAGATCTGCTGGCTTCGTTGTTACCATCCAATTCAGGCAGAGGTACTCTA
4201 TATCTCCCTTCATGTTTATCCATTTGTGACCACTTCCACTGTGACTCATTCACAGAGATCGTGTTTTATACTAAGACAGCATTAAAAATTATGAAGAAAATTATGAAGAAAAATTATGAAGAGAGGTACTCTA
4321 AA
```

FIG. 3A

[Figure 3A: Multiple sequence alignment of Bsk, Sek, Cek8, Cek4, Cek5, Elk, Cek10, Eck, and Eph protein sequences. The alignment is presented in three horizontal blocks, with conserved positions marked by asterisks (*) below each block. Residue numbers are shown at the left of each sequence.]

FIG. 3B

```
                                  *         #           #  #  #  #                         #       #   *                *           #                                                  #
Bsk  313  FFRADNDAAS  MPCTRPPSAP  LNLISNVNET  SVNLEWSSPQ  NTGGRQDISY  NVVCKKCG--  AGDPSKCRPC  GSGVHYTPQQ  NGLKTTRVSI
Sek  176  ---------- ----------  ----------  ----------  ----------  ----------  ----------  ----------  ----------  #
Cek8 309  Y..SEK.PP.  .A........  Q.........  ....A...D.  .K...D....  ...R......  ..E.H..S..  .....FS...  .....K....
Cek4 317  YY...A.PVD  ...TI.D...  R.V....I..  ..I.D.WPL.  D....K.VTF  .II.......  --SSKI.E..  SDN.RFL.R.  T..TN.T.TV
Cek5 307  YY..F.PPE.  VA..SV..G.  QAV..S....  ..LM..TP.R  DS...E.LV.  .II...S...  S.RGA-.TR.  .DN.QFA.R.  L..TEP.IY.
Elk  296  ....A.P.D.  SA..SV....  R.V..I....  ..II..HP.R  ET...D.VT.  .II....R--  AD.RS-.SR.  DDN.EFV.R.  L..TEC....
Cek10   1 ---------- ----------  RSV.......  ..FV....E..  DA...D.LL.  ..........  SVERRL.SR.  DDN.EFV.R.  L..TER.IY.
Cek9  1   ---------- ----------  ----------  ----------  ----------  ----------  ..........VR.  GDN.QFE.R.  V..TES..QV
Eck  314  ...PQDPA..  ..........  HY.TAVGMGA  KVE.R.TP..  DS....E..V.  S.T.EQ.W--  PE-SGE.G..  EAS.R.SEPP  H..TR.S.TV
Eph  317  HY..PGEGPQ  VA..G.....  R..SFSASG.  GLS.R.EP.A  DT......VR.  SVR.SQ.QGT  .Q.GGP.Q..  .V...FS.GA  RA...PA.HV

#                       # #                                      +           +        +             +
Bsk  306  ---------- ---------A  PSPVTNVKKG  KIAKNSISLS  WQEP-DRPNG  IILEYEIKYF  EK--------
Sek  401  TDLLAHTNYT  FEIWAVNGVS  KYNPSPDQSV  SVTVTTNQA.  ..SIAL.QAK  EVTRY.VA.A  .L........  V.......Y.
Cek8 264  ........V.  ......H..Q  ..A.......  ..IALIQAK.  E.TRH.VA.A  .L......-R  .........V  ..V...V..Y
Cek4 396  V.........  ...D......  DLSTLSR.FA  A.SI......  ..I.VIR.D.  RTSR..V...  ......-EH.  .....D..V.Y
Cek5 404  S.....Q...  .....Q....  DQS.FSP.FA  ..NI......  ..A.SIMHQV  SRTVD..T..  .SQ...Q...  V..D.LQ.Y.
Elk  394  SS.W...P..  .D.Q.I....  SKS.F.P.H.  ..NI......  ..T.PIMHQV  SATMR..T..  .PQ...EQ..  ..D..R.Y..
Cek10 383 SKVM..PQ..  ..Q..VNGI.  SKS.Y.PHFA  ..NI.......V  L.A.PTMHLH  SSTG..ME..  .TP.-ER...  ..D......S
Cek9  24  SN..RVQ...  ..Q...L.T  ELSSEAP.YA  TINVS.SQSV  .AIPMMHQV.  SRATS.IT..  .PQ...Q...  VILD.QLRYF  D-
Eck  401  S..EP.M...  .TVE.R....  GLVT-SRSFR  TAS.SI..TE  .PK.R.---E  GRSTT.L.V.  .SI-PPQQS  RVWK..VT.R  K-
Eph  407  NG.EPYA...  .NVE.Q....  GLGS.GHA.T  ..SISMGHAE  SLSGLSLRLV  .KEPRQLE.T  .AGSRP.SP.  AN.T..LHVL
Cek6                                                                                                   LSRICTPD

+                    +           +            +
Bsk  348  ---------- ---DQETSYTI  IKSKETSITA  EGLKPASVYV  FQIRARTAAG  YGVFSRRPEF  ETTPVSVAAS  NDQSQIPIIA  VSVTVGVILL
Cek7  1   ---------- ----------  ----------  ----------  ----------  ..........  .S....-L..  .S........V  ..........
Sek  482  -DQN.R..R.  VRTAARNTDI  K..N.LTS..  ..........  ..........  ..D..EPL.V  T.NT.PSRII  G.GANSTVLL  ...SGS.V.V
Cek8 345  -DQN.RT.R.  VKTASRNTDI  K..N.LTS..  ..........  .HV.......  ..D..GP...  T.NT.PSPII  GDGTNPTVLL  ...AGS.V.V
Cek4 477  -QE.......  LRA.S.NV.I  S....DTT..  ..........  .HV.......  ..TS..K...  ..S.D.FSI.  SEN..VVM..  ISAA.AI...
Cek5 485  -NLS.LNSTA  V..PTNTV.V  QN..AGTI..  ..........  ...V......  ..RY.GKMY.  Q.MTEAEYQT  SV.EKL.L.I  G.SAA.LVF.
Elk  475  EHNEFNSSM-  AR.QTNTARI  D..R.GM...  ..........  ...V......  ..K..GKMC.  Q.LTDDDYK.  ELRE.L.L..  G.AAA..VFV
Cek10 464 QGQGDGIANT  VTSQKNSVRL  D..ANAR.M   V.V....VA.  ..........  ..RY.LPT..  Q..AEDGST.  KTFQEL.L.V  G.A.A.LLFV
Cek9 105  -AED.DNSFT  LTSETNMA.I  LN.SPGKI.V  ..........  ...V......  ..PY.GKMY.  Q.LMGGEHSE  MA.DRL.L.V  G.ALG.LAF.
Eck  479  -GDSNSYNV   RRTEGF.VTL  DD.A.DTT.L  V.VQAL.QE.  ..........  Q.AG.KVH..  Q.L------.  PEG.GNLAVI  GG.AVG.V..
Eph  487  ---NQDEERY  QMVLEPRVLL  TELQPDTTYI  VRV.ML.PL.  P..P..PDH.  ..........  R.S.PVSRGL  TGGEIVAV.F  GLLLGAAL..
Cek6      VSGTVGSRPA  A
```

FIG. 3C

```
          AVMIGFLLSG SCCDCGCGRA SSLCAVAHPS LIWRCGYSKA KQDPEEEKMH FHNGHIKLPG VRTYIDPHTY EDPNQAVHEF AKEIEASCIT
Bsk   426 .V........ ....H...W. ....R...Y. .......... .......... .......... ......V.F. .......... .......... 
Cek7   52 .......... R--------- ---------- --R.SK.... ----KQEA.. DEEK..N-Q. ......V.F. .......R.. ......D..K
Sek   561 VIL.AAFVIS R--------- ---------- --R.SK.... ----KQEA.. DEEK.LN-Q. ........L. .......R.. ......D..K
Cek8  424 VIL.AAFVIS ---------- ---------- --RF...K.S .HGTD,KEL. .G...I.... ......E.R. .......... ......D..N.S
Cek4  556 T.VVYV.I-- ---------- ---------- --R.R.FER. DSEYTDKLQ. YTS..MT--- MKI.I..F.. .......... ......DI.VK
Cek5  564 IAVVIIIVC  N--------- ---------- --RKRA..-- EAVYSDKLQ. YST.RGS--- MKI....F.. .......E.R. .....DV.FVK
Elk   554 VSLVAISIVC ---------- ---------- ---RKRA..- QRNSTDPEYT EKLQQYVTP. MKI....F.. .......E.R. .....DI.VK
Cek10 544 IVVVIIAIVC ---------- ---------- -----FRK-- ETPYTDRLQQ YIST-RG--- MKV....F.. .......E.R. .....DV.FVK
Cek9  184 VIAAIAILAI I--------- ---------- ----FKSKRR R.S.D---V  YFSKSEQ.KP VKY....S.. .......E.IR ......DV.FIK
Eck   551 L.LA.VGFFI ---------- ---------- --HR.RKNQR. ---------- ---------- LK.V...... .......LK.. TT.HP.V.
Eph   564 GILVF----- -RSRRAGRQR QQRHVTAP.M W.E.TSCAE. LCGTSRHTRT L.REPWT... GWSNFPS--- ---------- -R.LDPAWLM

IERVIGAGEF GEVCSGCLKL -PGKRELPVA IKTLKVGYTE KQRRDFLGEA SIMGQFDHPN IIHLEGVVTK SKPVMIVTEY MENGSLDTFL
Bsk   516 .......... .......R.. -Q......F. .......... .......... .......... .......... .......... ..........
Cek7  142 ..K...V... .......... .......IC. .....A...D .......S.. .......... ..C....I.. .......... .....A....
Sek   623 ..K...V... ......R.V. .......IC. .....A...D .......S.. .......... ..C....I.. .......... ..ME.A....
Cek8  486 .DK.V..... .......R.. -S.K.IS... .......IF. .......... .......... .......R.. .......... .......S..
Cek4  623 ...Q...... .......H.. .......IF. .......IY. .......S.. .......... .......... .....S..V.F .......S..
Cek5  632 ...E...... ....YK.R.. .......IY. .......A.S .......S.. .......... .......R.. .......R..I.F ....A.S..
Elk   621 ...E...... .......R.R. .......IY. .......V..E ER.....D.S. .......... .......R.. .......R....E ....CA.S..
Cek10 607 ...E.S...S ....F.R..H. .......YT. .......S..D E...E...S. .......D.. .......... .......R....F .......S..
Cek9  249 ..KI.S..S. ....Y.R.QV -.QRDV.... .....A..A. .....R.Q..R ....G..... .......... .......R... .GRLA.....A
Eek     1 .RQT...E.. ....YK.M.T SS..K.V... ......A... .....A..... G.......SH. .......T.. .......R.. ..IS.Y.M.I ......A.K.
Eck   617 .VDT...E.. ....YR.T.R. -PSQDCKT.. .....DTSPG G.WWN..R.. .......S.. .......L.. .......R..I.I..F ....AA.A..
Eph   634

KKNDGQFTVI QLVGMLRGIA AGMKYLSDMG YVHRDLAARN ILINSNLVCK VSDFGLSRVL EDDPE-AAYT TR-GGKIPIR WTAPEAIAFR
Bsk   605 .......... .......... S......... .......... .......... .......... .......... --........ ..........
Cek7  231 ..R...R... .......... S......... .......... .......V.. .......M.. .......... ----.----- .......Y..
Sek   712 ..R...R... .......... S......G... .......... .......V.. .......M.. .......... ----.----- .......Y..
Cek8  575 R.H.A..... .......... S......... .......... .......V.. .......... .......... ----.----- .......Y..
Cek4  712 .RQ....... .......... .......... ....A..N.. .......V.. .......... .......F.. .TSDPT.SAL .......Y..
Cek5  721 .RQ....... .......... .......... .......E.N .......V.. .......... .......Y..Q .TSDPT.SSL ......V.Y..
Elk   710 .RL....... .......... .......... .......E.N .......V.. .......... .......F.. .ADPT..SSL .......Y..
Cek10 696 .RQKE..S.L .......... .......... ....R...D.N .......V.. .......... .......F.. .ASNPT.GAL.C .......Y..
Cek9  338 .RTH...IL. .......... .......... .......R..L. .......VDGR .......... .......A.. ....A-..... ......VQY.
Eek    90 .REK...S.L .......K.VG .......... .......AN.N .......V.. .......... .......... .....-T..S- .......SY.
Eck   706 .RERED.LVPG .......A..Q .......... .......N..NHN .....V.Q..C .......... .......T.L -..FD-GT.E .Q-......H
Eph   723
```

FIG. 3D

```
           KFTSASDVWS YGIVMWEVVS YGERPYWEMT NQDVIKAVEE GYRLPSPMDC PAALYQLMLD CWQKDRNSRP KFDEIVNMLD KLIRNPSSLK
Bsk    693 .......... .......... .......... .......... .......... .......... .......... .......... ..........
Cek7   319 .......... ....M..... .......... ....I..... .......P.. ..I.H..... ....E.SD.. ....GQ.... ...N......
Sek    800 .......... ....M..... ......D.S. ....I..... .......P.. ..I.H..... ....E.SD.. ....GQ.... ...N......
Cek8   663 .......... ....M..... ......D.S. .......... .......... .......... .......... ....EQ.SI. ..........
Cek4   800 ........A. ...L.M.... ........S. ......F... .......P.. .....N.H.. .......N.. ....GQ...T ...N......
Cek5   811 .......... ....M..... .......D.. ......N..Q .......P.. .....N.H.. .......H.. ....GQ...T ...M......
Elk    800 .......... ....M..... ......D.S. F......... .......P.. ..........  .......... R.A......T ...M......
Cek10  786 .......... ....M..... .......... ......N..Q .......P.. ....T..H.. ....VR...L ....AQ...T ...A......
Cek9   428 .......S.. ....M..... ......D.S. ......N.IDQ .......P.. .....TV.HL .......VQ. ....EQ.SA. ...AA.....
Eek    178 T..S...... .F..V....LA ......P..NMT .......... .....A..G. ......R..H ......H..AQ R.SHV.SV.E A.VHS.E.R
Eck    794 .......... .F.......MT ..........LS .HE.M..IND .F....T... ....S.I..MQ .....QE.AR. ....AD.SI. ...A.D....
Eph    810 ..I...T... .F........L .F.DK...G..S ...E.M.SI.D ......P.V. ..P..EL.KN ..AY..AR.. H.QKLQAH.E Q.LA..HC.R

TLVNASSRVS HGSLGSGAYR SVGEWLEAIK MGRYTEIFME NGYSSMDAVA QVTLEDLRRL GVTLVGHQKK KIMSSLQEMK
Bsk    783 TLLAE----- .......... .......... .......... .......... .......... .......... ..........
Cek7   409 N..V..---- .SPV...... .......... .......... .S........ .......... .......... --E.PC.KW.
Sek    890 RTGSE...PN .A.LD----- PS.PEFS.VV ...D..Q... E..KDN.TA. AG.TTLE..V HMSQD..A.I I.AIT..-N. ..L..V.A.R
Cek8   753 RTDSE...PS .A.LD----- PS.PEFS.VV ..SD..Q... E..KDN.CA. AG.TTLE..V HMNQD..A.I ITAIT..-N. ..L..V.A.R
Cek4   890 IITN.AA.P. N..LD----- QSNIDISAF. TA.D..NGFR T.QCLG..TG VE...C..TI. KISTD.MKKV ....V..P.. ..V..IKTLE
Cek5   901 AMAPL..G.N LP.LD----- RTIPDYTSFN T.D....D.. .SQ.K.S.AS A.FTTF.IVS M.V..IL.V. .......A.. ..LN.I.V.R
Elk    890 .VATITAVP. QP.LD----- RSIPDFTAFT T.DD...S.. VQ.RDS.LT. A.FT.LQL.T M.S....L.I .......A.. ...L..IHS.R
Cek10  876 VIASVQ.GV. QPL.D----- RTVPDYTTFT T..D..D... ..K.N.VN.. H.FA.F.LV. M.A....L.I .......A.. ..ILS.IQDMRL
Cek9   518 ATGTG...P. QPL.S----- NSPPDFPSLS NAH....D.. ..K.N.DQ.. A.LITF.VIS RM......Q.I .......I.. ..ILN.IQLMKV
Eek    268 ATATV.RCPA PAF.RSCFDL RAGGNGNGDL T..D..DS.R ..R.RDH.AA GG...LGM.L HMNAQ.V.AL .I..MG..-K ..LG.I.T.R
Eck    884 ..ADFDP... IR.PST---- -SGSDGIP.. T.S....S.K .QQ.TEH.MA A..TAIEK.V .M.ND.IK.I ..R.P..... R.AY.LLGL.
Eph    900 .IANFDPRVT LR.PCL---- -SQSDGIP.. T.S....S.R .KR.ILH.HS A.LDTMECVL EL.A.D.TQM IT.P..---- R.LC.I.GF.

VQMVNG---M VPV
Bsk    868 SLTLHPLFPT GYQT
Cek7   477 T..QQMHGR. ....
Sek    974 S..QQMHGR. ....
Cek8   837 THTK.S---P ....
Cek4   974 A..NQIQS-- .E..
Cek5   985 .NQSPSV. A
Elk    974 QMNQTL---P .Q..
Cek10  961 HLNQLEP--- .E..
Cek9   603 S.LSCTQGPR RHL
Eek    357 D.VNTVGIPI
Eck    968 D
Eph    984
```

FIG. 5D¹
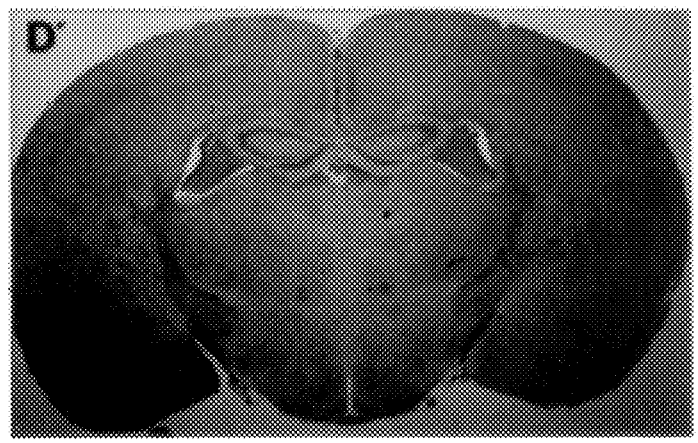
FIG. 5E¹
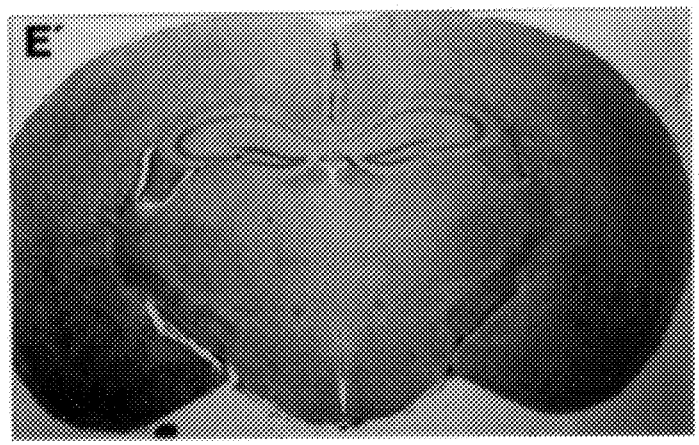
FIG. 5F¹
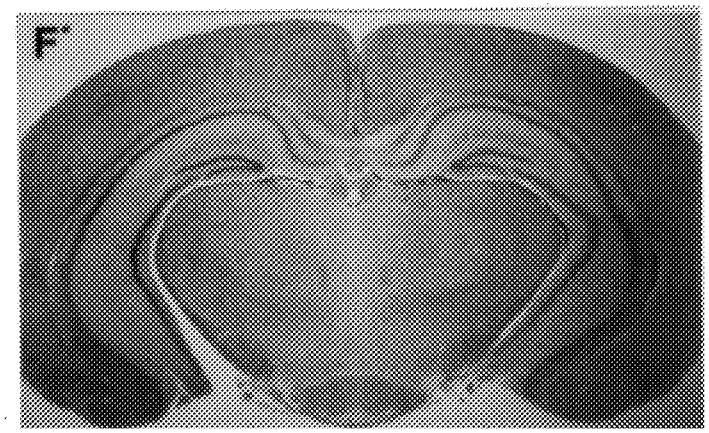

BSK RECEPTOR-LIKE TYROSINE KINASE

This is a continuation of application Ser. No. 08/177,812, filed on Jan. 4, 1994 now abandoned.

FIELD OF THE INVENTION

This invention is in the field of the neurotrophic receptors and their ligands. More specifically this invention relates to the receptor-like tyrosine kinase Bsk and its corresponding ligand and to therapeutic and diagnostic applications which employ the Bsk receptor or ligand.

BACKGROUND OF THE INVENTION

Neuronal degeneration has been shown to be involved in many neurological disorders (Price et al, (1987). In Wiley and Chichester (eds): "Selective neuronal death" Ciba Foundation Symposium 126, pp. 30–48). For example, in Alzheimer's Disease (AD), neuronal loss has been reported in a variety of brain structures including the locus coeruleus and raphe complex of the brainstem, the basal forebrain cholinergic system, amygdala, hippocampus and neocortex (Coleman and Flood, (1987) *Neurobiol. Acing* 8:521–545). Although the pattern of cell loss in AD has similarities to that in the aging brain, the speed and amount of loss is far greater. The most striking loss of neurons compared with the age-matched controls occurs in the hippocampal region, with a loss of up to 57% of the pyramidal cells (Coleman and Flood (1987) *Neurobiol. Aging* 8:521–545). These observations indicate that the hippocampus is a key structure in the neurobiology of AD. The extent of cell loss is most evident in the CA1 and subiculum, while areas CA3 and CA4 and granular cells of the dentate gyrus are largely spared (Van Hoesen and Hyman, (1990) *Progress in Brain Research* 83: 445–457).

Neuronal degeneration in the hippocampus has long been known to be a site of pathological change in epileptic patients (Nadler, (1989). In Chan-Palay V., Koehler C. (eds): "The Hippocampus-New Vistas" Alan R. Liss, Inc., pp. 463–481). CA3-CA4 damage is nearly always observed in pharmacologically intractable complex partial (limbic, temporal lobe, psychomotor) epileptic patients, while CA1 damage is also frequently observed (Nadler, (1989) in Chan-Palay V., Koehler C (eds) "The Hippocampus New Vistas" Alan R. Liss, Inc. pp 463–481). Since frequently prominent cell loss in the CA3-CA4 area may be present without obvious damage to area CA1, it is believed that the CA3 pyramidal cells and the morphologically diverse CA4 neurons are most vulnerable. Although the relationship between hippocampal sclerosis and seizure has been a controversy for over a century, recent studies with animal models indicate that although other etiologies may exist, hippocampal lesions can arise from prolonged febrile convulsions/status epilepticus (Sutula, (1990) *Epilepsia* 31:545–554). Furthermore, whatever the original cause of the sclerotic lesion, the damage serves as a focus for hyperexcitability and eventually causes spontaneous seizures. Formation of aberrant excitatory circuitry through axon sprouting and permanently depressed synaptic inhibition were thought to be two major factors linking hippocampal damage to the subsequent development of an epileptic focus (Nadler, (1989) in Chan-Palay V, Koehler C (Eds): "The Hippocampus-New Vistas" Alan R. Liss, Inc. pp. 341–355; Sutula, (1990) *Epilepsia* 31 (Suppl. 3): 545–554).

Hippocampal defects are also suggested to be involved schizophrenia (Bogerts et al., (1985) *Arch. Gen. Psychiatry* 42: 784–791). Significant reductions in hippocampal volume were found in chronic schizophrenic patients, possibly due to degenerative shrinkages of unknown etiology (Bogerts et al., (1985) *Arch. Gen. Psychiatry* 42: 784–791; Bogerts et al., (1993) *Biol. Psychiatry* 33: 236–246). The reduced volume in hippocampus and other limbic system structures such as amygdala and parahippocampal gyrus was associated with increased severity of psychopathology (Bogerts et al., (1993) *Biol. Psychiatry* 33: 236–246). These changes in the limbic system in schizophrenia are rather specific since the volumes of the putamen, caudate nucleus, nucleus accumbens, and the red nucleus of the stria terminalis did not differ between patients and controls (Bogerts et al., (1993) *Biol. Psychiatry* 33: 236–246).

The hippocampus and its adjacent, anatomically related entorhinal, perirhinal, and parahippocampal cortices play an essential, although temporal, role for establishing long-term memory for facts and events (Squire and Zola-Morgan, (1991) *Science* 253: 1380–1386). The widespread and reciprocal connections between hippocampal structures and neocortex may explain their degeneration in a variety of neurological diseases. Understanding the mechanism of neuronal survival in the hippocampus may help to develop effective treatments of neural degenerative diseases or disorders as well as neoplasms involving neuronal tissue.

It is known that growth/trophic factors promote the differentiation and survival of neurons during development and regeneration of the nervous system, with specific types of neurons requiring specific growth factors (Barde, (1989) *Neuron* 2:1525–1534). Nerve growth factor (NGF) has been a model trophic factor (Levi-Montalcini, (1987) *Science* 237:1154–1162; Black et al., (1990) In Nilsen-Hamilton M (ed): "Current Topics In Developmental Biology Volume 24" Academic Press Inc., pp. 161–182; Gage et al., (1991) In Bothwell M (ed): "Current Topics In Microbiology and Immunology Volume 165 " Springer Verlag, pp. 71–92). In vivo depletion by inducing an auto-immune reaction to NGF in rats and guinea pigs during embryonic development results in the destruction of up to 85% of the dorsal root ganglion neurons and the destruction of peripheral sympathetic neurons (Dolkart-Gorin and Johnson, (1979) *Proc. Natl. Acad. Sci. USA* 76:5382–5386; Johnson et al., (1980) *Science* 210:916–918). Other polypeptide growth factors also have trophic effects on neurons (Nieto-Sampedro and Bovolenta, (1990) In Storm-Mathison, Zimmer, Otterson (eds): "Progress in Brain Research Vol 83" Elsevier, pp 341–355). The fibroblast growth factors are well known mitogens (Gospodarowicz, (1990) In Nilsen-Hamilton M (ed): "Current topics in developmental biology Vol 24." Academic Press Inc., pp 57–93) that exhibit potent neurotrophic activity both in vivo (Anderson et al., (1988). *Nature* 332:360–361) and on cultured neurons from many brain regions (Morrison et al., (1986) *Proc. Natl. Acad. Sci. USA* 83:7537–7541; Morrison (1987) *Neuroscience Res.* 17:99–101; Walicke (1988) *J. Neurosci.* 6:1114–1121; Wagner (1991) In Bothwell M. (ed): "Current topics in microbiology and immunology Vol 165." Springer Verlag., pp 95–112) including the hippocampus (Walicke et al., (1986) *Proc. Natl. Acad. Sci. USA* 83:3012–3016). Epidermal growth factor (EGF) was shown to enhance the survival and process outgrowth of primary cultures of subneocortical telencephalic neurons of neonatal rat brain (Morrison et al., (1987) *Science* 238:72–75). Brain derived neurotrophic factor (BDNF) (Leibrock et al., (1989) *Nature* 341:149–152), and neurotrophin-3 (NT-3) (Maisonpierre et al., (1990) *Science* 247:1446–1451; Hohn et al., (1990) *Nature* 344:339–341) are two neurotrophic factors cloned recently. BDNF, related to NGF, has neurotrophic activity for sensory and retinal ganglion neurons and rescues spinal motor neurons in vivo from axotomy-induced cell death (Sendtner et al., (1992) *Nature* 360:757–759; Yan et al., (1992) *Nature* 360: 753–755). NT-3 was shown to support the growth of neurons from dorsal root ganglion, the neural placode-derived nodose ganglion and the paravertebral chain sympathetic ganglion (Maisonpierre et al., (1990) *Science* 247: 1446–1451).

The potential involvement of growth factors in neuronal regeneration after injuries or in disease is demonstrated by the fact that brain injury causes a time dependant increase in neurotrophic activity at the lesion site (Nieto-Sampedro et al., (1982) *Science* 217: 860–861). Furthermore, intraventricular administration of NGF prevents retrograde degeneration of axotomized septal cholinergic neurons (Hefti (1986) *J. Neurosci.* 6:2155–2162; Kromer (1987) *Science* 235: 214–216; Williams et al., (1986) *Proc. Natl. Acad. Sci. USA* 83:9231–9235) and local application of BDNF prevents spinal motor neuron degeneration after nerve section (Sendtner et al., (1992). *Nature* 360:757–759; Yan et al., (1992). *Nature* 360: 753–755). The therapeutic value of neurotrophic factors for nerve injury or neurodegenerative disease is shown by the observation that the symptoms of the mice with progressive motor neuropathy is relieved by the use of ciliary neurotrophic factor (Sendtner et al., (1992). *Nature* 358:502–504).

Growth/trophic factors function through their receptors which often possess intrinsic protein tyrosine kinase activity (Schlessinger and Ullrich (1992) *Neuron* 9:383–391). In general, the receptor protein-tyrosine kinases are composed of an extracellular domain, a membrane spanning domain and a catalytic domain (Schlessinger and Ullrich (1992) *Neuron* 9:383–391). Binding of the growth/trophic factor to the extracellular domain activates the catalytic domain inside the cell and results in phosphorylation of substrates within the cell. Activation of the receptor is believed to mediate a variety of cellular processes including cell growth and differentiation. In addition, many receptor tyrosine kinases are expressed during embryogenesis and are therefore believed to be important in the mechanisms underlying oncogenesis and cellular growth (Wilks, AF (1993) *Advances in Cancer Research* 60:43–73). Increased or aberrant expressions of tyrosine kinase receptors has been associated with several human neoplasms, including glioblastomas, squamos carcinomas, breast and gastric cancers (Carpenter, (1987) *Ann. Rev. Biochem* 56, 881–914; Muller et al., (1988) *Cell* 54, 105–109; Kraus et al (1989) *Proc. Natl. Acad. Sci. U.S.A.* 86: 9193–9197). Recently it has been demonstrated that expression of trk, the tyrosine kinase receptor for NGF, in neuroblastomas is indicative of a better prognosis for the patient than those patient's having neuroblastomas without trk expression (Kogner P. et al., (1993) *Cancer Research* 53:2044–2050; Nakagawara et al., (1993) *New Eng. J. Med.* 328:847–854; Suzuki, T. et al (1993) *J. Natl. Can Inst* 85:377–384), suggesting a therapeutic value for the neurotrophic receptors as well as their ligands.

Recently a new family of tyrosine kinase receptors have been discovered and designated the eph/elk family (Zhou et al., (1994) *J.Neuroscience Res.* 37(1):129–143; Sajjadi et al., (1993) *Oncogene* 8:1807–1813). Members of the eph/elk family have also been demonstrated to have aberrant expression in certain neoplasm as well as transforming ability. For example, elevated expression of Eph has been detected in carcinomas of the liver, lung, breast and colon (Hirai et al., (1987) *Science* 238:1717–1720; Maru et al., (1988) *Mol. Cell Biol.* 8:3770–3776). Over expression of eph has been shown to result in transformation of cells as well as development of tumors in nude mice (Maru et al., (1990), *Oncogene* 5:445–447). The distinct tissue distributions of the eph/elk family members suggest that each member may serve specific functions.

These findings demonstrate the extensive involvement of growth factors and their corresponding receptors in the survival of neurons and their potential therapeutic value in neurodegenerative diseases, neuronal disorders and neoplasms. Alzheimer's, epilepsy and schizophrenia are but a few of the diseases associated with degeneration of neurons in the hippocampus. However, the factors needed for the regeneration and survival of neurons in the hippocampus and its associated limbic system are poorly characterized. The identification of factors which promote the regeneration and survival of these neurons will be potentially useful in the treatment of the neoplasms, neurodegenerative diseases or disorders and brain injuries involving the limbic system.

SUMMARY OF THE INVENTION

It is a general object of the present invention to provide a nucleic acid sequence which encodes for the Bsk receptor-like tyrosine kinase.

It is another object of this invention to provide a recombinant molecule comprising a vector and all or part of the nucleic acid sequence encoding Bsk.

It is another object of this invention to produce recombinant proteins encoded by all or part of the nucleic acid sequence encoding Bsk.

It is a further object of this invention to provide monoclonal or polyclonal antibodies reactive with the Bsk protein.

It is an object of this invention to provide methods of detecting the Bsk gene or Bsk mRNA in a biological sample.

It is another object of this invention to provide methods of detecting the Bsk protein in a biological sample.

It is an object of this invention to provide diagnostic methods for human disease, in particular neurodegenerative diseases, disorders, and injuries.

It is a further object of this invention to provide methods for therapeutic uses involving all or part of the nucleic acid sequence encoding Bsk and its corresponding protein.

It is a further object of this invention to provide assays for the isolation of the ligand or ligands capable of activating the Bsk receptor and therapeutic uses for said ligand.

It is another object of this invention to provide assays for the assessment and development of drugs capable of activating the Bsk receptor and therapeutic uses for said drugs.

DESCRIPTION OF THE FIGURES

FIG. 2A–C shows complete nucleotide sequence of the longest Bsk cDNA clone (SEQ ID NO: 1) and predicted amino acid sequence. (SEQ ID NO:2) The putative signal peptide at the very N-terminal and the transmembrane domain are underlined, the potential N-linked glycosylation sites are underlined by dashed lines, the glycine and lysine residues of the ATP-binding domain are circled. Regions characteristic of the eph/elk family receptor tyrosine kinases are boxed. The stop codons preceding and after the coding region are indicated by asterisks.

FIG. 3A–D shows comparison of the amino acid sequences from all the known members of the eph/elk family. The human and mouse homologs of cek4, hek and mek, are not included. Only 19 residues of cek6 (SEQ ID NO:12), which is not known to be present in its rat homolog elk are shown. Amino acid residues in cek7 (SEQ ID NO:13), Sek (SEQ ID NO:3), cek 8 (SEQ ID NO:10), cek4 (SEQ ID NO:4), cek5 (SEQ ID NO:5), elk (SEQ ID NO:6), cek10 (SEQ ID NO:7), cek9 (SEQ ID NO:11), eck (SEQ ID NO:8), eph (SEQ ID NO:9), and eek (SEQ ID NO:14 ) identical to the corresponding residues in Bsk are represented by dots. In the region deleted in Bsk (SEQ ID NO:2), sequences of sek (SEQ ID NO:3) is shown and amino acid residues in other family members identical to that of sek are also replaced by dots to show homology among the family members. Putative signal peptide sequences and transmembrane domains are underlined. The conserved cysteine residues among the eph/elk family members are indicated by asterisks; The conserved amino acid residues in the two fibronectin III-like domains are marked with "#" and "+" signs respectively. The cysteines in the juxtamembrane domain in Bsk are identified by circles. Amino acids are numbered at the left of the sequences. The amino acid sequences were analyzed using the PILEUP program (Genetics Computer Group, Inc., Wisconsin). References for the sequences are as follows: sek, Gilardi-Hebenstreit et al., (1992) *Oncogene* 7: 2499–2506; cek4 and mek4: Sajjadi et al., (1991) *The New Biologist* 3: 769–778; cek6,7, 8, 9, 10: Sajjadi and Pasquale, (1993) *Oncogene* 8: 1807–1813; elk, Lhotak et al., (1991) *Mol. and Cell Biol.* 11: 2446–2502; eek, Chan and Watt, (1991) *Oncogene* 6: 1057–1061; eck, Lindberg and Hunter, (1990) *Mol. and Cell Biol.* 10: 6316–6324.; eph, Hirai et al, (1987) *Science* 238: 1717–1720; hek, Wicks et al., (1992) *Proc. Natl. Acad. Sci USA* 89: 1611–1615.

FIGS. 5A–F, show dark field views of coronal sections of one month old mouse brain hybridized to [$^{35}$S]-labeled Bsk-specific anti-sense probe. Boxed regions are shown in more details in FIG. 6. FIGS. A'–F' show neighboring sections of those shown in A–F respectively and were stained with hematoxylin and eosin and photographed in bright field. AF: anterior frontal cortex, AC: anterior cingulate cortex; IL: infralimbic cortex; TT: tenia tecta; Pir: Piriform cortex; OT: olfactory tubercle; IG: indusium griseum; DB: vertical diagonal band/media septum; HDB: horizontal limb diagonal band; HP: hypothalamus; DG: dentate gyrus; CM: central medial thalamic nuclei; AD: amygdaloid area.
Magnification 12.5×.

FIGS. 6A–C and 6'–6C' shows magnified view of Bsk-positive regions boxed in FIG. 5. FIG. 6A shows the darkfield view of the piriform cortex showing the Bsk-positive pyramidal cell layer and the Bsk-negative olfactory tubercle (OT). FIG. 6B shows the darkfield view of indusium griseum (IG). FIG. 6C shows the darkfield view of the CA1-CA2-CA3 (CA:Cornu Ammonis) junction region, showing the different intensities of Bsk signal in CA1 and CA3 regions of the hippocampus. FIGS. 6A'–C' show hematoxylin and eosin staining of the corresponding regions as shown in FIGS. 6A–C respectively.
Magnification 50×.

FIGS. 7B and B' show dark and bright field view (silver stained tissue) of the hippocampal area. H: hippocampus; OB: olfactory bulb; S: subiculum. Magnification 12.5×.

DETAILED DESCRIPTION OF THE INVENTION

Figure 1:
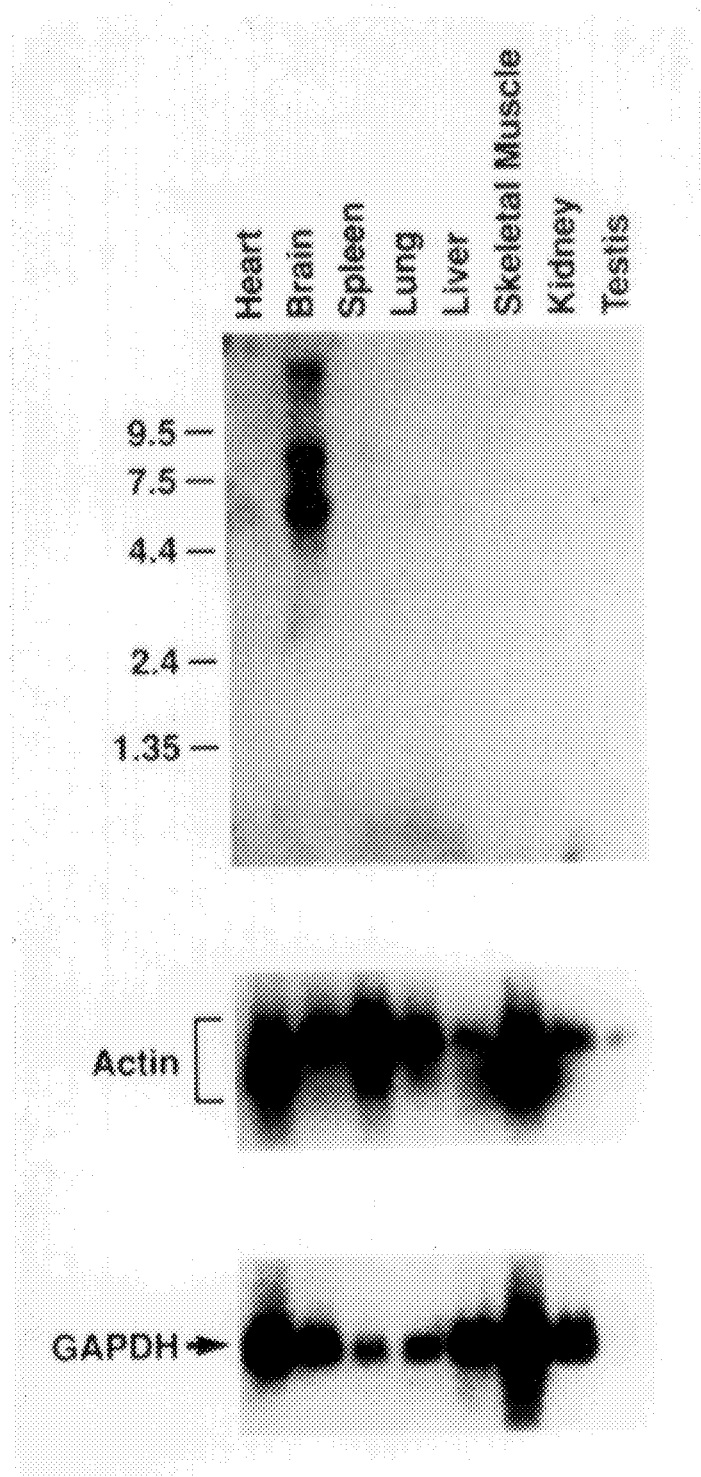
FIG. 1 shows Northern blot analysis of Bsk expression in adult mouse tissues. Two micrograms of poly A⁺ mRNA from each adult tissue as indicated were hybridized with a nick-translated 4.3 kilobase (kb) Bsk cDNA probe (upper panel). RNA size markers (in kb) are indicated at left. Middle and lower panels show the results of the rehybridization of the same blot with a human actin and a rat glyceraldehyde-3-phosphate dehydrogenase (GAPDH) probe respectively.

For the purpose of a more complete understanding of the invention, the following definitions are described herein. Nucleic acid sequences includes, but is not limited to, DNA, RNA or cDNA. Nucleic acid sequence as used herein refers to an isolated and purified nucleic acid sequence. Bsk messenger RNA (mRNA) refers to one or more RNA transcripts which are a product of the Bsk gene. Substantially homologous as used herein refers to substantial correspondence between the nucleic acid sequence of Bsk shown in FIG. 2 (SEQ ID NO.:1) and that of any other nucleic acid sequence. Substantially homologous means about 60% homology, preferably by about 75% homology, and most preferably about 85% homology between the Bsk sequence and that of any other nucleic acid sequence. In addition, substantially homologous as used herein also refers to substantial correspondences between the amino acid sequence of the Bsk receptor shown in FIG. 2 (SEQ ID NO.:2) and that of any other amino acid sequence.

Ligand refers to any protein or proteins that may interact with the Bsk receptor binding domain. Said ligand or ligands may be soluble or membrane bound. The ligand or ligands may be a naturally occurring protein, or synthetically or recombinantly produced. The ligand may also be a nonprotein molecule that acts as ligand when it interacts with the Bsk receptor binding domain. Interactions between the ligand and receptor binding domain include, but are not limited to, any covalent or non-covalent interactions. The receptor binding domain is any region of the Bsk receptor molecule that interacts directly or indirectly with the Bsk ligand.

Drugs include, but is not limited to proteins, peptides, degenerate peptides, agents purified from conditioned cell medium, organic molecules, inorganic molecules, antibodies or oligonucleotides. Other candidate drugs include analogs of the Bsk ligand or ligands. The drug may be naturally occurring or synthetically or recombinantly produced. One skilled in the art will understand that such drugs maybe developed by the assays described below.

The term neurodegenerative disease includes, but is not limited to, states in a mammal which can include chromosomal abnormalities, degenerative growth and developmental disorders, viral infections, bacterial infections, brain injuries, or neoplastic conditions. Examples of neurodegenerative diseases that can be diagnosed, assessed or treated by methods described in the present application include, but are not limited to, Alzheimer's disease, epilepsy, schizophrenia. In a preferred embodiment diseases characterized by neurodegeneration in the limbic system are diagnosed, assessed or treated by methods disclosed in the present application. Examples of injuries to the nervous system include, but are not limited to, stroke and cerebral ischemia due to stroke or cardiac arrest. Also considered within this definition is the treatment of injury to the nervous system. Further, neoplasms involving neuronal tissue may be diagnosed, assessed or therapeutically treated by methods suggested herein.

One skilled in the art will understand that the bioassays of the present invention may be used in the analysis of biological samples or tissues from any vertebrate species. In a preferred embodiment mammalian biological samples or tissues are analyzed.

Tissue includes, but is not limited to, single cells, whole organs and portions thereof. Biological samples include, but are not limited to, tissues, primary cultures of mammalian tissues, biopsy specimens, pathology specimens, and necropsy specimens. Mammal includes but is not limited to, humans, monkeys, dogs, cats, mice, rats, pigs, cows, pigs, horses, sheep and goats.

The present invention provides a nucleic acid sequence which encodes a novel receptor tyrosine kinase. This novel receptor like kinase is designated Bsk (brain specific kinase). Bsk is highly related to the eph/elk receptor like kinase family and thus represents a new member of this family. The Bsk receptor-like tyrosine kinase appears to have its greatest level of expression in the hippocampus and its associated limbic structures. The cDNA sequence for Bsk is shown in FIG. 2 (SEQ ID NO:1), the deduced amino acid sequence for the Bsk protein is also shown in FIG. 2 (SEQ ID NO.:2).

The nucleic acid sequence for Bsk shown in FIG. 2 (SEQ ID NO.:1), represents a preferred embodiment of the invention. It is, however, understood by one skilled in the art that due to the degeneracy of the genetic code variations in the cDNA sequence shown in FIG. 2 (SEQ ID NO.:1) will still result in a DNA sequence capable of encoding the Bsk protein. Such DNA sequences are therefor functionally equivalent to the sequence set forth in FIG. 2 (SEQ ID NO.:1) and are intended to be encompassed within the present invention. Further, naturally occurring allelic variations in a given species of the Bsk nucleic acid sequence shown in FIG. 2 (SEQ ID NO.:1) are also intended to be encompassed by the present invention.

The predicted Bsk protein is about a 105 kd transmembrane polypeptide with structural features which identify it as a member of the eph/elk family of tyrosine kinase receptors. This invention further includes the Bsk protein or peptides having substantially the same function as the Bsk receptor like tyrosine kinase protein of this invention. Such proteins or polypeptides include, but are not limited to, a fragment of the protein, or a substitution, addition or deletion mutant of the Bsk protein. This invention also encompasses proteins or peptides that are substantially homologous to the Bsk receptor. Substantially homologous means about 80% homology, preferably about 90% homology, and most preferably about 95% homology between the Bsk receptor and any another amino acid sequence or protein.

This invention also provides a recombinant DNA molecule comprising all or part of the Bsk nucleic acid sequence (SEQ. ID NO.:1) and a vector. Expression vectors suitable for use in the present invention comprise at least one expression control element operationally linked to the nucleic acid sequence. The expression control elements are inserted in the vector to control and regulate the expression of the nucleic acid sequence. Examples of expression control elements includes, but is not limited to, lac system, operator and promoter regions of phage lambda, yeast promoters and promoters derived from polymer, adenovirus, retrovirus or SV40. Additional preferred or required operational elements include, but are not limited to, leader sequence, termination codons, polyadenylation signals and any other sequences necessary or preferred for the appropriate transcription and subsequent translation of the nucleic acid sequence in the host system. It will be understood by one skilled in the art the correct combination of required or preferred expression control elements will depend on the host system chosen. It will further be understood that the expression vector should contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecules Biology", John Wiley and Sons, New York, N.Y.) or commercially available.

Another aspect of this invention relates to a host organism into which recombinant expression vector containing all or part of the Bsk nucleic acid sequence has been inserted. The host cells transformed with the Bsk nucleic acid sequence of this invention includes eukaryotes, such as animal, plant, insect and yeast cells and prokaryotes, such as *E. Coli*. The means by which the vector carrying the gene may be introduced into the cell includes, but is not limited to, microinjection, electroporation, transduction, or transfection using DEAE-dextran, lipofection, calcium phosphate or other procedures known to one skilled in the art (Sambrook et al. (1989) in "Molecular Cloning. A Laboratory Manual", Cold Spring Harbor Press, Plainview, N.Y.).

In a preferred embodiment, eukaryotic expression vectors that function in eukaryotic cells are used. Examples of such vectors include but are not limited to vaccinia virus vectors, adenovirus vectors, herpes virus vector and the baculovirus transfer vectors. Preferred eukaryotic cell lines include, but are not limited to, COS cells, CHO cells, HeLa cells, NIH/3T3 cells and PC12 cells. In a particularly preferred embodiment the recombinant Bsk protein expression vector is introduced into mammalian cells, such as NIH/3T3, COS or CHO, to ensure proper glycosylation of the Bsk protein.

In one embodiment the expressed recombinant Bsk protein may be detected by methods known in the art which include Coomassie blue staining and Western blotting using antibodies specific for the Bsk protein.

In a further embodiment, the recombinant protein expressed by the host cells can be obtained as a crude lysate or can be purified by standard protein purification procedures known in the art which may include differential precipitation, molecular sieve chromatography, ion-exchange chromatography, isoelectric focusing, gel electrophoresis, affinity, and immunoaffinity chromatography and the like. (Ausubel et. al., (1987) in "Current Protocols in Molecular Biology" John Wiley and Sons, New York, N.Y.). In the case of immunoaffinity chromatography, the recombinant protein may be purified by passage through a column containing a resin which has bound thereto antibodies specific for the Bsk protein (Ausubel et. al., (1987) in "Current Protocols in Molecular Biology" John Wiley and Sons, New York, N.Y.).

The nucleic acid sequence or portions thereof, of this invention are useful as probes for the detection of expression of the Bsk gene in normal and disease tissue. Therefore, another aspect of the present invention relates to a bioassay for detecting messenger RNA encoding the Bsk protein in a biological sample comprising the steps of (a) contacting all or part of the nucleic acid sequence of this invention with said biological sample under conditions allowing a complex to form between said nucleic acid sequence and said messenger RNA, (b) detecting said complexes and, (c) determining the level of said messenger RNA.

RNA can be isolated as whole cell RNA or as poly(A)$^+$ RNA. Whole cell RNA can be isolated by a variety of methods known to those skilled in the art. (Ausubel et al., (1987) on "Current Protocols in Molecular Biology", John Wiley and Sons, New York). Such methods include extraction of RNA by differential precipitation (Birnboim, H. C. (1988) *Nucleic Acids Res.*, 16:1487–1497), extraction of RNA by organic solvents (Chomczynski, P. et al. (1987) *Anal. Biochem.*, 162:156–159) and the extraction of RNA with strong denaturants (Chirgwin, J. M. et al. (1979) *Biochemistry*, 18:5294–5299). Poly(A)$^+$ RNA can be selected form whole cell RNA by affinity chromatography on oligo-d(T) columns (Aviv, H. et al. (1972) *Proc. Natl. Acad. Sci.*, 69:1408–1412). Examples of methods for determining cellular messenger mRNA levels for step (c) include, but is not limited to Northern blotting (Alwine, J. C. et al. (1977) *Proc. Natl. Acad. Sci.*, 74:5350–5354), dot and slot hybridization (Kafatos, F. C. et al. (1979) *Nucleic Acids Res.*, 7:1541–1522), filter hybridization (Hollander, M. C. et al. (1990) *Biotechniques*; 9:174–179), RNase protection (Sambrook et. al., (1989) in "Molecular Cloning, A Laboratory Manual", Cold Spring Harbor Press, Plainview, N.Y.), polymerase chain reaction (Watson, J. D. et al. (1992) in "Recombinant DNA" Second Edition, W. H. Freeman and Company, New York) and nuclear run-off assays (Ausubel et. al., (1987) in "Current Protocols in Molecular Biology" Supplement 9 (1990); John Wiley and Sons, New York, N.Y.).

Detection of complexes in Step (b) of the bioassay can also be carried out by a variety of techniques. Detection of the complexes by signal amplification can be achieved by several conventional labelling techniques including radiolabels and enzymes (Sambrook et. al., (1989) in "Molecular Cloning, A Laboratory Manual", Cold Spring Harbor Press, Plainview, N.Y.; Ausubel et al., (1987) in "Current Protocols in Molecular Biology", John Wiley and Sons, New York N.Y.). Radiolabelling kits are also commercially available. The Bsk nucleic acid sequence used as a probe in step(c) of the bioassay may be RNA or DNA. Preferred methods of labelling the DNA sequences are with [$^{32}$P] using Klenow enzyme or polynucleotide kinase. Preferred, methods of labeling RNA or riboprobe sequences are with [$^{32}$P] or [$^{35}$S] using RNA polymerases. In addition, there are known non-radioactive techniques for signal amplification including methods for attaching chemical moieties to pyrimidine and purine rings (Dale, R. N. K. et al. (1973) *Proc. Natl. Acad. Sci.*, 70:2238–2242; Heck, R. F. (1968) *S. Am. Chem. Soc.*, 90:5518–5523), methods which allow detection by chemiluminescence (Barton, S. K. et al. (1992) *J. Am. Chem. Soc.*, 114:8736–8740) and methods utilizing biotinylated nucleic acid probes (Johnson, T. K. et al. (1983) *Anal. Biochem.*, 133:125–131; Erickson, P. F. et al. (1982) *J. of Immunology Methods*, 51:241–249; Matthaei, F. S. et al (1986) *Anal. Biochem.*, 157:123–128) and methods which allow detection by fluorescence using commercially available products. Non-radioactive labelling kits are also commercially available.

Examples of biological samples that can be used in this bioassay include, but are not limited to, primary mammalian cultures, continuous mammalian cell lines, mammalian organs such as brain and testes, tissues, biopsy specimens, neoplasms, pathology specimens, and necropsy specimens.

In a preferred embodiment, a $^{32}$[P] radiolabelled Bsk probe, as exemplified in Example 1, is used. Preferably the Bsk probe is the 4.3 kilobase nucleic acid fragment shown in FIG. 2 (SEQ ID NO.:2). The complete 4.3 kb Bsk cDNA (FIG. 2; SEQ ID NO:1) was cloned into the pBluescript vector and the resulting pBsk plasmid, deposited with the American Type Culture Collection (ATCC) 12301 Parklawn Drive, Rockville, Md. 20852 USA on Dec. 7, 1993, and given ATCC Deposit Number 75620. The full length Bsk nucleic acid sequence can be isolated from the pBsk plasmid by digestion with EcoR1 and Xho1 restriction enzymes. This 4.3 kb nucleic acid sequence can then be nick translated and used as a probe. This probe is used to detect Bsk mRNA in a poly A$^+$ RNA isolated from a variety of tissues or biological samples.

In another embodiment, combinations of oligonucleotide pairs based on the Bsk sequence in FIG. 2 (SEQ ID NO.:1) are used as Polymerase Chain Reaction (PCR) primers to detect Bsk mRNA in a biological sample. These primers can be used in a method following the reverse transcriptase—Polymerase Chain Reaction (RT-PCR) process for amplifying selected RNA nucleic acid sequences as detailed in Ausubel et al., (eds) (1987) In "Current Protocols in Molecular Biology" Chapter 15, John Wiley and Sons, New York, N.Y. The oligonucleotides can be synthesized by automated instruments sold by a variety of manufacturers or can be commercially prepared based upon the nucleic acid sequence of this invention.

The Bsk nucleic acid sequence or portions thereof (FIG. 2: SEQ ID NO:1) of this invention are useful to detect alterations of the Bsk gene in normal or diseased mammalian tissue. By alteration, we mean additions, deletions, substitutions or duplications in the Bsk gene sequence or gene amplification of the Bsk gene sequence. Therefore, another aspect of the present invention relates to an assay for detecting alterations of the Bsk gene in a biological sample comprising the steps of (a) contacting all or part of the nucleic acid sequence of this invention with genomic DNA isolated from a biological sample under conditions allowing a complex to form between said nucleic acid sequence and said genomic DNA, (b) detecting said complexes, and (c) determining alterations in said Bsk gene by comparison to a control sample.

Standard methods for isolating DNA from a biological sample, detecting alterations in a gene and detecting complex between the Bsk nucleic acid probe and genomic DNA sequences are provided in manuals such as Sambrook et al., (eds) (1989) "Molecular Cloning, A Laboratory Mineral", Cold Spring Harbor Press, Plainview, N.Y. and in Ausubel et al., (eds) (1987) in "Current Protocols in Molecular Biology" John Wiley and Sons, New York, N.Y.

The Bsk nucleic acid sequences of this invention (FIG. 2; SEQ ID No.:1) can also be used as probes to isolate the Bsk homologs in other species. In a preferred embodiment the Bsk CDNA (FIG. 2; SEQ ID No.:1) is used to screen a mammalian CDNA library, positive clones are selected and sequenced. Examples of tissue sources from which the cDNA library can be synthesized includes, but are not limited to brain, testes and embryos. Preferably a human brain cDNA library is screened using the 4.3 kb Bsk cDNA as a probe (FIG. 2; SEQ ID No. 1). One skilled in the art will understand the appropriate hybridization conditions to be used to detect the homologs. Conventional methods for nucleic acid hybridization, construction of libraries and cloning techniques are described in Sambrook et al., (eds) (1989) In "Molecular Cloning A Laboratory Manual" Cold Spring Harbor Press, Plainview, N.Y. and Ausubel et al., (eds) in "Current Protocols in Molecular Biology" (1987), John Wiley and Sons, New York, N.Y.

It is known that Bsk is a member of the eph/elk family of tyrosine kinase receptors. It also is known, as discussed above, that alterations in the levels of expression of members of the eph/elk family is associated with some neoplastic conditions. It is therefore another aspect of this invention to provide Bsk nucleic acid probes to be utilized in detecting alterations in the level of Bsk mRNA in biological sample isolated from a mammal afflicted with a disease. Examples of such diseases, include but is not limited to, neurodegenerative diseases or disorders and neoplasms. By alterations in the level of Bsk mRNA we mean an increase or decrease in the level of an RNA relative to a control sample or the appearance or disappearance of the Bsk mRNA relative to a control sample. Detection in the alterations of Bsk mRNA will allow for diagnosis or the assessment of the diseased state. As discussed previously, the presence of the trk receptors on neural tumors is predictive of a better prognoses for the afflicted individual. Therefore, alterations in the level of Bsk mRNA may be predictive of the prognosis for the afflicted mammal.

In another embodiment the nucleic acid of this invention can be used in in situ hybridization on mammalian tissues to determine the precise site of expression of the Bsk gene within a tissue. A preferred method of labeling the Bsk nucleic acid sequence is by synthesizing a [$^{35}$S]-labeled RNA probe by in vitro transcription utilizing the T7 polymerase. In the pBsk plasmid (ATCC Deposit # 75620) the sense strand is under the control of the T3 promoter, the antisense strand is under the T7 promoter. It is preferable that the probe be hydrolyzed to a probe length of approximately 200 base pairs (Zhou et al (1994) *J. Neuroscience. Res.* 37(1):129–143). Conventional methods for preparation of tissues for in situ, synthesis of probes and detection of signal can be found in Ausubel et. al., (eds) (1987) in "Current Protocols in Molecular Biology," John Wiley and Sons, New York, N.Y. Chapter 14 and Vander Ploeg, M., Raap A. K. (1988) In "New Frontiers in Cytology" Goerttler, K., Feichter, GE, Witte. S. (eds) pp 13–21 Springer-Verlag, N.Y. The probe is then contacted with mammalian tissue sections and in situ analyses performed by conventional methods. Examples of tissues that can be used include but is not limited to, mammalian embryos, adult mammalian tissues, such as brain and testes, biopsy specimens, pathology specimens and necrospy specimens.

Hippocampal neurons are formed from embryonic day 10 until birth (Angevine, (1965) *Experimental Neurology Supp* 2:1–70). In a preferred embodiment mouse embryos from day 9 to birth and newborn mouse pups will be sacrificed and fixed in 4% formalin, embedded and sectioned (Zhou et. al. (1994) *J. Neuroscience Res* 37(1): 129–143; Ausubel et. al. (eds) (1987) In "Current Protocols in Molecular Biology" Chapter 14, John Wiley & Sons, New York, N.Y.). The sections can be hybridized to [$^{35}$S] -labeled Bsk antisense and sense control probe generated using the pBsk plasmid (ATCC # 75620). Messenger RNA from embryonic day 9 (E9) through birth will be extracted by conventional methods described above and analyzed using the Bsk nucleic acid sequence of this invention as a probe.

This invention further comprises an antibody reactive with the Bsk protein having the amino acid sequence defined in FIG. 2 (SEQ ID NO: 2) or a unique portion thereof. In this embodiment of the invention the antibodies are monoclonal or polyclonal in original. Bsk protein or peptides used to generate the antibodies may be from natural or recombinant sources or generated by chemical synthesis. Natural Bsk proteins can be isolated from mammalian biological samples. Biological samples include, but is not limited to mammalian tissues such as brain, testis, primary or continuous cultures of mammalian cells. The natural Bsk proteins may be isolated by the same methods described above for recombinant proteins. Recombinant Bsk proteins or peptides may be produced and purified by conventional methods. Synthetic Bsk peptides may be custom ordered or commercially made on the predicted amino acid sequence of the present invention (FIG. 2; SEQ ID:2) or synthesized by methods known to one skilled in the art (Merrifield, R. B. (1963) *J. Amer. Soc.* 85:2149). If the peptide is too short to be antigenic it may be conjugated to a carrier molecule to enhance the antigenicity of the peptide. Examples of carrier molecules, includes, but is not limited to human albumin, bovine albumin and keyhole limpet hemo-cyanin ("Basic and Clinical Immunology" (1991) Stites, D. P. and Terr A. I. (eds) Appleton and Lange, Norwalk Connecticut, San Mateo, Calif.).

Exemplary antibody molecules for use in the detection methods of the present invention are intact immunoglobulin molecules, substantially intact immunoglobulin molecules or those portions of an immunoglobulin molecules that contain the antigen binding site, including those portions of an immunoglobulin molecules known in the art as F(ab), F(ab'); F(ab')$_2$ and F(v). Polyclonal or monoclonal antibodies may be produced by methods known in the art. (Kohler and Milstein (1975) *Nature* 256, 495–497; Campbell "Monoclonal Antibody Technology, the Production and Characterization of Rodent and Human Hybridomas" in Burdon et al. (eds.) (1985) "Laboratory Techniques in Biochemistry and Molecular Biology," Volume 13, Elsevier Science Publishers, Amsterdam). The antibodies or antigen binding fragments may also be produced by genetic engineering. The technology for expression of both heavy and light chain genes in *E. Coli* is the subject of the PCT patent applications: publication number WO 901443, WO 901443 and WO 9014424 and in Huse et al. (1989) *Science* 246:1275–1281.

The antibodies of this invention may react with native or denatured Bsk protein or peptides. The specific immunoassay in which the antibodies are to be used will dictate which antibodies are desirable. Antibodies raised against the C-terminus of the Bsk protein or against synthetic peptides homologous to the carboxy terminus, of the Bsk protein are desirable.

In one embodiment the antibodies of this invention are used in immunoassays to detect the novel Bsk receptor protein in biological samples. In this method the antibodies of the present invention are contacted with a biological sample and the formation of a complex between the Bsk protein and antibody is detected. Immunoassays of the present invention may be radioimmunoassay, Western blot assay, immunofluorescent assay, enzyme immunoassay, chemiluminescent assay, immunohistochemical assay and the like. (In "Principles and Practice of Immunoassay" (1991) Christopher P. Price and David J. Neoman (eds), Stockton Press, New York, N.Y.; Ausubel et al. (eds) (1987) in "Current Protocols in Molecular Biology" John Wiley and Sons, New York, N.Y.). Standard techniques known in the art for ELISA are described in *Methods in Immunodiagnosis*, 2nd Edition, Rose and Bigazzi, eds., John Wiley and Sons, New York 1980 and Campbell et al., *Methods of Immunology*, W. A. Benjamin, Inc., 1964, both of which are incorporated herein by reference. Such assays may be a direct, indirect, competitive, or noncompetitive immunoassay as described in the art (In "Principles and Practice of Immunoassay" (1991) Christopher P. Price and David J. Neoman (eds), Stockton Pres, New York, N.Y.; Oellirich, M. 1984. *J. Clin. Chem. Clin. Biochem.* 22: 895–904) Biological samples appropriate for such detection assays include mammalian tissues, cell lines PC12 cells, pathology specimens, necropsy specimens, and biopsy specimens.

Proteins may be isolated from biological samples by conventional methods described in (Ausubel et al., (eds) (1987) in "Current Protocols in Molecular Biology" John Wiley and Sons, New York, N.Y.).

As discussed previously, alterations in the level of expression of certain eph/elk family members has been associated with neoplastic disease. The antibodies of this invention can therefore be used in immunoassays to determine alteration in expression of the Bsk protein in biological samples isolated from mammals afflicted with a disease or disorder. Examples of biological samples include, but are not limited to, mammalian tissues, biopsy tissue samples, brain and testis biopsy samples, pathology and tissue samples. Examples of diseases that can be assessed by these immunoassays, include, but are not limited to, Alzheimer's, epilepsy and schizophrenia. By alteration in level, we mean an increase or decrease of the Bsk protein relative to a control sample. Alterations is also meant to encompass substitution, deletion or addition mutants of the Bsk protein. Such mutations can be determined by using the antibodies of this invention known to react with specific epitopes of the Bsk protein and determining which epitopes are present relative to a control. The antibodies of this invention can therefore be used in immunoassay to diagnose, assess or prognose a mammal afflicted with the disease.

In another embodiment, antibodies of this invention may be used to purify the Bsk receptor protein or portions thereof. Immunoaffinity chromatography can be defined by conventional methods known to one skilled in the art (Ausubel et al. (eds) (1987) in "Current Protocols in Molecular Biology" John Wiley and Sons, New York, N.Y.).

In a preferred embodiment rabbit antisera containing antibodies which specifically recognize the Bsk receptor protein is used to detect said protein in western blot analysis. Such antisera is directed to a synthetic peptide representing a unique portion of the Bsk protein, preferably the synthetic peptide having the sequence (in single letter amino acid code) HGSLGSGAYRSVGE corresponding to amino acid positions 798–811 in the predicted sequence of the Bsk protein (FIG. 2; SEQ ID NO:2). A cysteine residue is attached to the amino terminal end of the peptide to allow linkage of the peptide to a carrier molecule. (M. Bodanszky (1984) "Principles of Peptide Synthesis," Springer Verlag, New York, N.Y.). The peptide is synthesized by standard methods on a automated peptide synthesizer and purified by high pressure liquid chromatography (HPLC). The purified peptide is conjugated to a carrier, preferably keyhole limpet, via the terminal cysteine. Using conventional methods, rabbits are immunized with the Bsk peptide conjugated to carriers. Preferably about 0.5–2 milligrams (mg) of antigen in Freund's most adjuvant are used, most preferably about 1 mg of antigen in Freunds' adjuvant. The animal receives similar booster doses and antisera titer is assessed by ELISA assay. Satisfactory levels of antisera are obtained when the anti-peptide antibody titer reaches a plateau. This antibody can be used in the standard immunoassays described above.

The anatomical boundaries of the limbic system is continually been redefined since it is a complex system and there were no good markers for limbic neurons. If the expression of a particular gene in a specific type of cell indicates a shared property of these cells, then the previously isolated monoclonal antibody against a limbic associated membrane protein (LAMP) (Levitt P (1984) *Science* 223: 299–301) and the antibodies of this invention will serve to better define the limbic system. Study of LAMP and Bsk expression may identify previously unknown neurons involved in limbic function. Thus, yet another embodiment of this invention is use of the Bsk reactive antibodies in assays to define neurons potentially involved in limbic system function.

In another embodiment, the expression of Bsk protein will be studied in developing embryos using immunocytochemistry. Peptide anti-Bsk antibodies will be affinity-purified using antigen peptides. Embryo sections from different stages will be stained using affinity-purified anti-Bsk antibodies using conventional methods (Harlow and Lane (eds.) (1988) In "Antibodies A Laboratory Manual", Cold Springs Harbor Press, Cold Spring Harbor, N.Y.; Ausubel et. al., (eds) (1987). In "Current Protocols in Molecular Biology," John Wiley and Sons, New York, N.Y.).

Growth/trophic factors exert their functions through their receptors. The binding of the ligands to the receptors activates the tyrosine kinase activity intrinsic to the receptors, thus transmitting the signals through the cell membrane. Studies of chimeric receptors consisting of extracellular domain of one receptor and the intracellular domain of a different receptor indicate that a common mechanism of signal transduction through the cell membrane is shared by different growth factor receptors (Riedel et al., (1986) *Nature* 324:68–70; Riedel et al., (1989) *EMBO J.* 8:2943–2954). The specificity of the receptors resides in the intracellular domain (Riedel et al., (1989) *EMBO J.* 8:2943–2954). This property allows the assessment of the biological function of the receptors before their ligands have been identified. Chimeras between the extracellular domain of a known ligand and intracellular domain of an orphan receptor can be activated by the known ligand, yet the biological function elicited is similar to the receptor with the intracellular domain (Riedel et al., (1989) *EMBO J.* 8:2943–2954). Numerous chimeric receptors including insulin receptor (IR)/epidermal growth factor receptor (EGFR) (Riedel et al., (1986) *Nature* 324:68–70), EGFR/IR (Riedel et al., (1989) *EMBO J.* 8:2943–2954), platelet-derived growth factor receptor beta (PDGFR-beta)/fibroblast growth factor receptor-1 (FGFR-1; Mares et al., (1992) *Growth Factors* 6:93–101), and M-CSFR (Colony Stimulating Factor Receptor)/trk have been constructed and elicited proper biological responses.

This property can be utilized to construct a chimeric receptor using the extracellular domain of a receptor with known ligand and the intracellular domain of Bsk. It is preferable that there should be no expression of this receptor in the PC12 cells or the brain, since the endogenous receptor would complicate the interpretation of the results. It is also preferable that the ligand be available in sufficient quantity for biological assays. The human macrophage colony stimulating factor receptor (M-CSFR) which mediates the differentiation of macrophage cells induced by M-CSF (Coussens et al., (1986) *Nature* 320:277–280) satisfies this criteria. The M-CSF receptor is expressed mostly in hematopoietic cells and with no expression detected in the brain (Sherr et al., (1985) *Cell* 41:665–676) M-CSF is also commercially available. M-CSFR has been successfully used in M-CSFR/Trk chimeric receptor studies.

In a preferred embodiment M-CSFR/Bsk chimeric receptor is constructed containing the M-CSFR extra cellular domain and the Bsk transmembrane and intracellular domains. Alternatively, the chimeric receptor can contain the M-CSFR extracellular domain and transmembrane domain and intracellular domain of Bsk. Either of these chimeric receptors can be expressed under the LTR promoter in NIH/3T3 to study whether it has a mitogenic effect or in PC12 cells to determine whether it induces differentiation.

An alternative embodiment to study the biological function of Bsk kinase involves the use of constitutively active Bsk kinase receptors. Receptor kinase mediate functions of their ligands through activation of their kinase activity which lays dormant without ligand stimulation. It is possible to create mutant forms of the receptors which are constitutively active, bypassing the need of ligand stimulation. These truncated activated receptors will function in a similar fashion as that of the ligand-stimulated normal receptors.

Constitutively active Bsk Receptor tyrosine kinases can be generated by a variety of mutations, many of which involve gross structural changes such as truncation or replacement of the N- or C-terminal domains of the receptors (Wilks, (1993) *Advances in Cancer Research* 60:43–73). However, activating point mutations also exist (Roussel et al., (1990) *Oncogene* 5:25–30). A single point mutation in the extracellular domain of M-CSF receptor was able to activate an otherwise wild-type protein (Roussel et al., (1990) *Oncogene* 5:25–30). Receptors with such mutations resemble the ligandactivated receptors more closely than those with large structural changes, since the substrate interaction sites of the receptors are most likely conserved.

To create a constitutively active Bsk kinase, a full length Bsk receptor kinase can be cloned into a retroviral vector. Due to the low fidelity of reverse transcriptase, retroviral replication introduces mutations frequently into genes in the viral genome (Temin, (1988) *Cancer Research* 48:1697–1701). The virus can be propagated in NIH/3T3 cells, and the virus with the activating mutations is selected by its ability to form foci, since it has been shown that activated versions of the normal receptors such as trk (Coulier et al., (1990) *Mol. Cell. Biol.* 10:4202–4210) can cause transformation in fibroblasts, much like the ligand-activated normal trk (Jing et al., (1992) *Neuron* 9:1067–1079 and trk B (Klein et al. (1991) *Cell* 66:395–453). The foci will be picked and propagated separately. Virus from each foci will be characterized by Northern blot analysis of viral RNA, Southern blot analysis of integrated viral DNA and Western blot of Bsk protein to study the changes which activates the kinase. Viruses carrying the activated Bsk kinase with the least amount of structural changes can be used for further studies.

In another embodiment to study the biological effect of Bsk, the activated Bsk gene can be cloned with a RT-PCR technique which combines the use of reverse transcription and PCR reactions and expressed using herpes simplex virus- or adenovirus-based vectors (LeGal LeSalle et al., (1993) *Science* 259:988–990).

Several studies have demonstrated that the introduction of an expression vector for receptor tyrosine kinases into mammalian cells results in coupling of the introduced receptor to the secondary messenger systems within the host cell and thus the potential to mediate the biological activities of the host cell (Jing et al. (1992) *Neuron* 9:1067–1079). An expression vector containing the Bsk nucleic acid sequence is introduced into a host cell and expressed to produce functional Bsk receptor integrated in the membrane of the host cell. Such recombinant cell systems are useful for developing and assessing candidate drugs or ligands that would mediate Bsk receptor activity. The type of biological activity mediated by the recombinant Bsk receptor will depend on the cell type and stage of differentiation of the cell or tissue. Examples of biological activities that would identify a Bsk candidate drug, ligand or ligand analogs includes, but are not limited to, detection of autophosphorylation of the Bsk receptor protein, stimulation of DNA or protein synthesis, induction of the transformed phenotypes in cells such as NIH/3T3 and phosphorylation of cytoplasmic proteins. Accordingly, another embodiment of the present invention relates to a bioassay for testing candidate drugs or ligands of the Bsk receptor for the ability to affect biological activity mediated by the Bsk receptor, comprising the steps of (a) contacting a candidate drug or ligand with a cell producing functional Bsk receptors and (b) evaluating the biological activity mediated by said contact.

Examples of cell into which the Bsk receptor can be introduced and functionally expressed includes but is not limited to, PC12 cells, primary hippocampal neurons, and NIH/3T3 cells. Examples of sources for candidate drugs or ligands with which to expose recombinant cells expressing the Bsk receptor includes, but is not limited to, medium from primary cultures of hippocampal neurons, conditioned medium from PC12 cells or NIH/3T3 cells and mammalian brain homogenates.

In a preferred embodiment, the Bsk nucleic and sequence shown in FIG. 2 (SEQ.ID.NO:1) is cloned into an adenoviral vector and introduced by infection into PC12 cells. Integration of a functional Bsk receptor into the PC12 membrane can be determined by surface labeling. PC12 cells expressing the Bsk receptor can be exposed to the candidate drug or ligand and the cells evaluated for neurite outgrowth. Cells transfected with vector alone serve as controls. It is preferred that the cells into which the Bsk expressions vector is introduced are not expressing endogenous Bsk receptor.

In another embodiment the Bsk sequence encoding the Bsk receptor (FIG. 2, SEQUENCE ID NO:1) is cloned into a retroviral expression vector and introduced into NIH/3T3 cells by infection. The NIH/3T3 expressing the Bsk receptor are exposed to candidate drugs or ligands and the ability of the candidate drug or ligand to induce transformation evaluated. The ligand or candidate drug may be isolated by conventional biochemical techniques.

The present invention further relates to therapeutic methods using the constitutively activated form of the Bsk receptor protein. The constitutively activated form of the Bsk protein can be generated and delivered into the limbic system of patients with limbic system neurodegenerative disease, disorder or injury to promote or enhance limbic system neuron regeneration or growth.

Because of the blood-brain barrier, the constitutively active Bsk receptor must be directly micro-injected into the diseased or injured region of the mammal's limbic system. Examples of appropriate gene delivery systems include, but are not limited to, viruses, retroviruses or adenoviruses.

Conventional methods can be used to microinject a therapeutically effective amount of the gene delivery system into the mammalian brain (L. Heimer and M. Robards (eds) (1981) "Neural Anatomical Track-Tracing Methods" Plenum Press, New York). The constitutively active form of the Bsk receptor to be used in the gene delivery systems will be determined by the in vitro bioassays described above for evaluating the constitutive forms of the Bsk receptor.

In an alternative embodiment stem cell populations for either neuronal or glial cells can be genetically engineered to express a functional Bsk receptor. Such cells recombinantly expressing the Bsk receptor, can be transplanted to the diseased or injured region of the mammal's limbic system (S. B., Donnet and A. Djorklund (eds) (1992) "Neural Transplantation. A Practical Approach" Oxford University Press, New York). In yet another alternative embodiment, embryonic tissue or fetal neurons can be genetically engineered to express functional Bsk receptor and transplanted to the diseased or injured region of the mammal's limibic system. The feasibility of transplanting fetal dopamine neurons into Parkinsonian patients has recently been demonstrated. (Lindvall et al. *Archives of Neurology* (1989) 46:615–631).

Studies of the molecular interactions between ligands and their receptors showed that only the extracellular domain of the receptor is involved in the special physical interaction between the molecules (Riedel et al., (1986) *Nature* 324:68–70; Riedel et al. (1989) *EMBO J.* 8:2943–2954). Thus, the extracellular domain of a receptor can be used as a probe to screen an expression cDNA library for the Bsk ligand or ligands. In one approach for detection of the receptor probe, placental alkaline phosphatase will be fused to the extracellular domain of a receptor, and positive clones will be detected by the presence of alkaline phosphatase activity.

An alternative approach is to isolate the putative Bsk ligand is to utilize the findings that coexpression of a receptor and its ligand in the same cells results in uncontrolled proliferation and malignant transformation (Klein et al., (1991) *Cell* 66:395–403; Gazit et al., (1984) *Cell* 39:89–97). A eukaryotic cDNA expression library can be transfected into cells expressing a receptor, and the presence of a ligand will create an autocrine loop, resulting in a transformed phenotype. This approach has been successfully used by Miki et al. (1991) *Science* 251:72–75 to isolate the receptor of the keratinocyte growth factor (KGF) using cells expressing KGF. In yet another alternative approach the Bsk receptor protein can be expressed in a cell line or in *Xenopus oocytes* by the recombinant techniques described above and its ligand stimulated activation of tyrosine kinase activity, as detected by an anti-phosphotryosine antibody (UBI, Happauge, N.Y.) can be used to assay and purify the ligand. For example, cells expressing the recombinant Bsk receptor can be exposed to mammalian brain extract. The brain extracts can be fractionated by chromatography and used to assay for the presence of the ligand activity. Once an activity is identified in a particular fraction, it can be further purified by conventional biochemical techniques.

In another alternative approach the Bsk extracellular domain can be used to screen a random peptide library (Cull et al., (1982) *Proc. Natl. Acad. Sic. USA* 89: 1865–1869; Lam et al., (1991) *Nature* 354:82–84). Peptides isolated can be assayed for their ligand activity in the above described assays for drug screening.

In another embodiment of this invention, the Bsk ligand is expressed as a recombinant gene in a cell, so that the cells may be transplanted into a mammal, preferably a human in need of gene therapy. To provide gene therapy to an individual, a genetic sequence which encodes for all or part of the Bsk ligand is inserted into a vector and introduced into a host cell. Examples of diseases that may be suitable for gene therapy include, but are not limited to, neurodegenerative diseases or disorders, Alzheimer's, schizophrenia, epilepsy, neoplasms and cancer. Examples of vectors that may be used in gene therapy include, but are not limited to, defective retroviral, adenoviral, or other viral vectors (Mulligan, R.C., (1993) *Science* 260: 926–932). The means by which the vector carrying the gene may be introduced into the cell include, but is not limited to, microinjection, electroporation, transduction, or transfection using DEAE-dextran, lipofection, calcium phosphate or other procedures known to one skilled in the art (Sambrook et. al. (eds) (1989) in "Molecular Cloning. A Laboratory Manual", Cold Spring Harbor Press, Plainview, N.Y.).

Examples of cells into which the vector carrying the gene may be introduced include, but are not limited to, continuous culture cells, such as COS, NIH/3T3 and PC12.

Means of administering the Bsk ligand or parts thereof include, but are not limited to, oral, sublingual, intravenous, intraperitoneal, percutaneous, intranasal, intrathecal, subcutaneous, intracutaneous, or enteral. Local administration to the afflicted site may be accomplished through means known in the art, including, but not limited to, topical application, injection, and implantation of a porous device containing cells recombinantly expressing the infusion, implantation of a porous device in which the Bsk ligand or portions thereof are contained. Alternatively, such porous device may also contain recombinant host cells expressing the Bsk ligand.

In another embodiment, successful candidate drugs developed in the bioassays of this invention may be administered by the above mentioned methods.

All books, articles, or patents referenced herein are incorporated by reference. The following examples illustrate various aspects of the invention but are no way intended to limit the scope thereof.

EXAMPLE 1

DNA Sequence and Deduced Amino Acid Sequence of Bsk

Isolation and sequencing of positive clones

Bsk was isolated by screening an adult mouse brain expression cDNA library in lambda ZAP II vector (Stratagene, LaJolla, Calif.) using the anti-phosphotyrosine antibody 4G10 (gift of Derby Morrison at Advanced Biological Laboratory, Frederick, Md.; also available from UBI, Hauppauge, N.Y.). This antibody is specific for tyrosine-phosphorylated proteins and does not cross-react with phosphoserine, phosphothreonine, phosphohistidine, or tyrosine sulfate (Kanakura et al., (1991). *J. Biol. Chem.* 266:490–495). The primary antibody was detected by alkaline phosphatase conjugated secondary antibody and visualized with the phosphatase substrates (BioRad, Hercules, Calif.). Of the 1,000,000 clones examined, 270 positive clones were isolated. Lambda phage of the positive clones were then hybridized with a probe made from one of the positive clones. After stringent washes [(0.1× standard saline citrate (SSC), 0.5% sodium-dodecyl-sulfate (SDS), 68° C.)] of the hybridized filters, clones hybridizing to the probe were detected by X-ray autoradiography. These clones were scored as different isolates of the same gene. The filters were then washed in boiling water and reprobed with a probe from the remaining clones. The reprobing was continued until all the clones had been analyzed. Probes from each gene group were then used in Northern Blot analysis to identify brain specific genes. cDNA clones were sequenced using a dideoxynucleotide chain termination sequencing reaction (Sanger et al., (1977). *Proc. Natl. Acad. Sci. USA* 74:5463–5467). Sense and antisense oligonucleotide primers based on partial sequences obtained from sequencing reactions using the T7 or Sk primers were used to complete sequencing with T7 DNA polymerase (USB, Ohio).

Northern Blot Analysis

Nylon membranes containing 2 micrograms of poly A$^+$ mRNA from each tissue indicated were purchased from Clontech, Palo Alto, Calif. (Catalog #7767-1). Prehybridization and hybridization were carried out at 42° C. in 50% formamide, 0.5M NaCl, sheared heat-denatured salmon testes DNA (100 microgram/ml), 7% SDS, 0.25M sodium phosphate (pH 7.2), and 1 mM EDTA, containing [$^{32}$P] -labeled probe at a final concentration of $10^6$ to $10^7$ cpm/ml. The murine Bsk probe was the 4.3 kb gel purified fragment, labeled by nick-translation. The 4.3 kb fragement is contained in the pBsk plasmid deposited with ATCC on Dec. 7, 1993, ATCC Deposit Number 75620. Posthybridization washes were as follows: twice with 2× standard saline citrate (SSC) and 0.1% SDS at 25° C. for 25 min, twice in 25 mM sodium phosphate (pH 6.5) and 0.1% SDS at 50° C. for 25 min, and twice in 25 mM sodium phosphate (pH 6.5) and 1.0% SDS at 50° C. for 25 min. After the high-stringency wash, the filters were exposed to Kodak X-AR film at −70° C. with DuPont Cronex Lightning Plus intensifying screens.

The cross hybridization and partial DNA sequence analysis of the clones isolated in the screening of the mouse brain cDNA library showed that these clones represent eight distinct tyrosine kinase genes. Four of these genes have been isolated previously, they are syn (Semba et al., (1986). *Proc. Natl. Acad. Sci. USA* 83:5459–5463), lyn (Yamanashi et al., (1987) *Mol. Cell. Biol.* 7:237–243), elk (Lhotak et al., (1991) *Mol and Cell Biol.* 11:2496–2502), and cek-5 (Pasquale, (1991) *Cell Regulation* 2:523–534). Partial sequences of the remaining four genes indicate that they are novel tyrosine kinases. Northern blot analysis indicated that one is expressed only in adult brain (FIG. 1), with no detectable signals in heart, spleen, lung, liver, skeletal muscle, kidney or testis. This gene is therefore designated Bsk, for brain specific kinase.

Twelve independent clones of Bsk sequence were isolated and the longest cDNA clone (4.3 kb) was sequenced. The Bsk DNA sequence (SEQ ID NO:1) and deduced amino acid sequence (SEQ ID NO:2) are shown in FIG. 2A–C. A putative initiation ATG codon, preceded by two stop codons is located beginning at nucleotide position 418. The −3 position of the initiation codon (SEQ ID NO:1, nucleotide position 415) is a conserved A residue for translational initiation (Kozak, (1989) *J. Cell. Biol.* 108:229–241). An open reading frame extends for 877 amino acids. A putative signal peptide found at the N-terminal (SEQ ID NO:2, amino acid residues 1–51), and a transmembrane domain in the middle (SEQ ID NO:2, amino acid position 413–433) of the protein indicate that it is a transmembrane protein (FIG. 2A–C) (Singer, (1990). In Palade GE, Alberts BM, Spudich JA (ed) "Annual Review of Cell Biology Volume 6" Annual Reviews Inc., pp 247–296). The predicted molecular weight of Bsk after removing the signal peptide is 98600 Daltons (Da). The extracellular domain of Bsk contains a cysteine-rich domain (SEQ ID NO:2 - residues 52–306) and a region homologous to fibronectin type III (SEQ ID NO:2 residues 307–412) characterized by the presence of aromatic and hydrophobic residues and lack of conserved cysteine residues (FIG. 3A–D).

The cytoplasmic domain (residues 433–877) contains the characteristic features of protein tyrosine kinase catalytic domains, including a typical ATP-binding site (GXGXXG) (Hanks et al., (1988). *Science* 241:42–52) and the receptor kinase signature motif as well as the characteristic sequence motifs for the eph/elk family of receptors (FIG. 2A–C). This indicates that Bsk is a putative growth factor receptor with intrinsic tyrosine kinase activity. Immediately following the transmembrane domain, there is an additional cysteine rich domain (residues 434–460) which is not present in other eph/elk family members (FIG. 3A–D), indicating that Bsk may have unique functions. Sequence analysis also showed that Bsk had extensive homology with members of the eph/elk receptor-like protein tyrosine kinase family members (FIG. 3A–D). Bsk shares a 95% homology with the partial cDNA sequence of cek-7 published recently (Sajjadi and Pasquale, (1993). *Oncogene* 8:1807–1813) over a region of 470 amino acids covering the transmembrane domain, the ATP-binding and catalytic domain (FIG. 3A–D). Thus Bsk may represent the murine homolog of cek-7 receptor-like kinase in chicken. Consistent with this observation, cek-7 is also expressed exclusively in the brain (Sajjadi and Pasquale, (1993). *Oncogene* 8:1807–1813). Bsk is also highly related to sek (Gilardi-Hebenstreit et al., (1992). *Oncogene* 7:2499–2506) and cek 8 (Sajjadi and Pasquale (1993). *Oncoqene* 8:1807–1813) (74.2% identity over the intracellular domain) (FIG. 3A–D). Cek8 shares a 93.5% homology at the amino acid level over the known coding region of 849 amino acids with sek, a putative receptor kinase implicated in the segmental patterning of the hindbrain and mesoderm (Nieto et al. *Development* 116:1137–1150). Thus, cek8 is likely to be a chicken homolog of the previously isolated mouse sek gene.

The extracellular domains of the eph/elk family receptor kinases have a long cysteine rich region and two fibronectin III-like repeats (Pasquale, (1991) *Cell Regulation* 2:523–534) (FIG. 3A–D). Bsk is unique among the eph/elk family members in that a 170 amino acid region including 9 out of 19 conserved cysteines of the eph/elk family is missing in the extracellular domain (FIG. 3A–D). This region also contains one of the two fibronectin III-like repeats. Thus Bsk has only part of the cysteine-rich domain and one fibronectin III-like repeat.

Restriction enzyme digestion analysis of other independently isolated Bsk clones indicates there are at least five different cDNA structures suggesting differential splicing.

The Northern blot analysis revealed at least two distinct mRNA species (FIG. 1). The largest band seen in brain in the Northern Blot Analysis (FIG. 1) is possibly DNA or unprocessed Bsk mRNA. Thus, it is likely that the clone presented here is one of the many splice variants of the Bsk gene. Bsk is also unique in that there is an additional cysteine rich juxta-membrane domain not present in other members of the family (FIG. 3A–D).

EXAMPLE 2

Bsk Encodes a Protein of Approximately 105 kD in Mouse Brain.

Peptide synthesis and antibody preparation

The peptide CHGSLGSGAYRSVGE (amino acids positions 798 to 811 of SEQ ID NO:2, with a cysteine residue attached to the amino terminal end of the peptide) was assembled on a peptide synthesizer (Applied Biosystems Model 430A) using t-butoxycarbonyl chemistry. The peptide was severed from the resin and side chain protecting groups with hydrogen fluoride containing 10% anisole and 19% dimethylsulfide, triturated with ether, and extracted into 60% acetonitrile and 50% acetic acid. Following lyophilization the peptide was purified by reversed phase high performance liquid chromatography. The purified peptide gave a correct amino acid composition. The peptide was conjugated to keyhole limpet hemocyanin (KLH) via the terminal cysteine using the bifunctional reagent, m-maleimidobenzoyl-N-hydroxysuccinimide ester (Pierce, Rockford, Ill. ). The ratio of peptide to KLH was 1:1 (w:w). A rabbit was immunized with 1 mg of the peptide-KLH conjugate in Freund's complete adjuvant. After 1 month, boosts were begun with 0.1 mg of the conjugate in Freund's incomplete adjuvant (100 microliters of 1 mg/ml) at two week intervals. Boosts were continued until satisfactory peptide antisera was obtained. Antisera levels were determined by Western Blots of mouse brain extracts.

Figure 4:
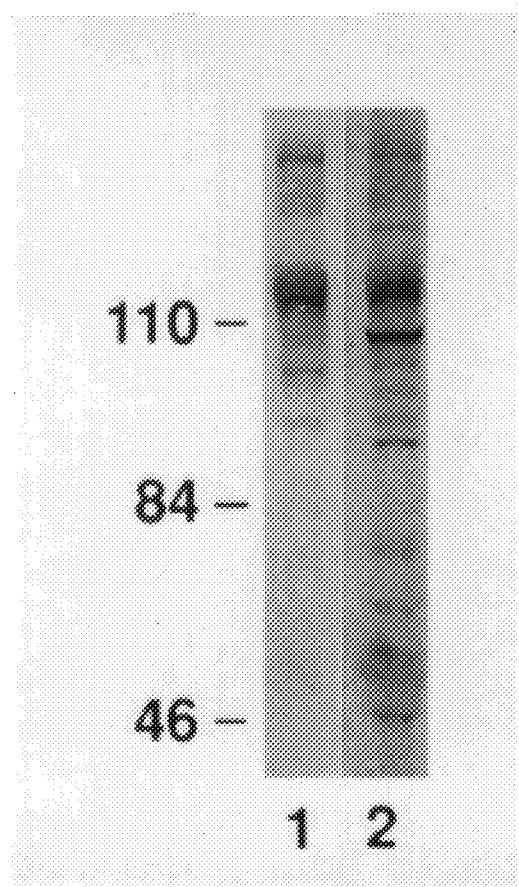
FIG. 4 shows Western blot analysis of Bsk product. 100 μg of a head extract of 16.5 day mouse embryo was loaded in each lane and fractionated using SDS-PAGE and transferred to nitrocellulose membrane. The membranes were then probed with pre-immune serum (lane 1) and an antiserum raised against a peptide CHGSLGSGAYRSVGE near the C-terminal of the predicted amino acid sequence of Bsk (lane 2) respectively. The Bsk protein is indicated by the *.

To identify the Bsk gene product, the rabbit anti-peptide antibody was used to perform western blot (FIG. 4) analysis. The blot was blocked and incubated in 3% Bovine Serum Albumin (BSA) in 1X Tris Buffered Saline (TBS) (Ausubel et al. (eds) (1987) "Current Protocols in Molecular Biology" John Wiley and Sons, New York, N.Y.). The anti-peptide antibody was used at a dilution of 1:500. A 105 kD protein was detected by the anti-serum (FIG. 4, lane 2) but not by the pre-immune serum (FIG. 4, lane 1) using alkaline phosphatase-conjugated secondary antibody (BioRad, California). The apparent molecular weight of Bsk is somewhat higher than the predicted molecular weight (98.6 kD). This discrepancy might be explained by glycosylation of the extracellular domain, as two possible glycosylation sites are present in the extracellular domain (FIG. 2A–C), as well as other post-translational modifications. The proteins at approximately 90 kd and 46 kd detected by the antiserum (FIG. 4, lane 2) but not by the pre-immune serum (FIG. 4, lane 1) are potentially different forms of the Bsk protein.

EXAMPLE 3

Bsk is Expressed in High Levels in Limbic Structures of the Adult Mouse Brain

In situ hybridization

One month old adult normal mouse brain from Balb/c mice and Balb/c embryos (Balb/c mice obtained from, the mouse facility at ABL, Fredrick Cancer Research and Development Center, Frederick, Md.) fixed in 4% paraformaldehyde for between 3–5 hrs. The tissues were then dehydrated through 30%, 50%, 90%, 100% ethanol sequentially and placed in xylenes for 1 hour, then paraffin-embedded. Sections were 5 microns thick and affixed to poly-lysine coated glass slides. The slides were then prepared for hybridization by washes as follows: Xylenes twice for 10 minutes, 100% ethanol twice for one minute, 70% ethanol, 30% ethanol, one minute each, then PBS twice. Post-fixation was achieved in 4% paraformaldehyde for 20 min, then washed in PBS for one minute, in 0.3% Triton X-100 in PBS for 15 min and PBS for one minute (twice). The slides were then permeabilized with Proteinase K (one microgram/ml in 0.1M Tris pH 8 and 50 mM EDTA pH 8) for 30 min at 37° C., then washed in PBS twice. Slides were then acetylated in 400 ml of 0.1M (12 ml/liter) triethanolamine with 1 ml of acetic anhydride for 10 minutes. An incubation of 30 minutes in 0.1M Tris pH 7, 0.1M glycine preceded prehybridization at 55° C. in 50% formamide/1X SSC for 15 minutes. Slides were then hybridized to a full length Bsk CDNA riboprobe which has undergone base hydrolysis to yield a mean probe length of approximately 200 bp. Both sense and antisense riboprobe (Ausubel et al. (eds) (1987) in "Current Protocols in Molecular Biology" John Wiley and Sons, New York, N.Y.), was generated using the pBsk plasmid (ATCC #75620). 500,000 cpm probe per slide was added and hybridized overnight in a 55° C. humidified chamber with 50% formamide/1X SSC. Post hybridization stringency washes were as follows: 50% formamide/1X SSC for 40 minutes, then a 30 minute RNase incubation at 37° C., again 50% formamide/1X SSC at 52° C. for 30 minutes. The slides were then dehydrated through 30%, 50%, 70%, 95%, and 100% ethanol sequentially for five minutes each time and autoradiographed using Kodak NTB-2 emulsion at full strength. Slides were exposed at 4° C. in a desiccator between 2–10 days. After development the slides were counterstained with 0.1% toluidine blue.

Figure 5A:
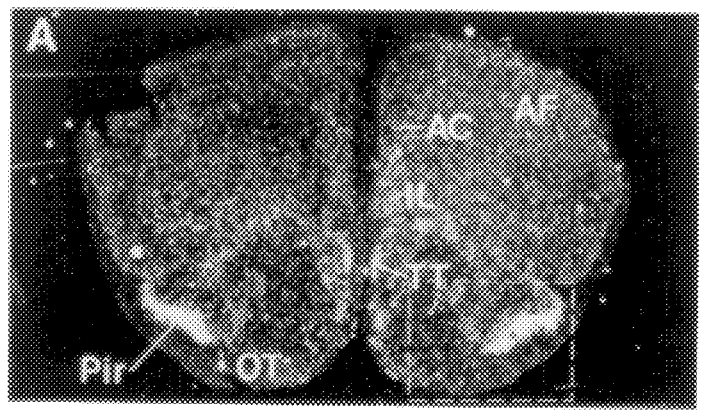
FIGS. 5A–F and 5A'–F'shows coronal views of Bsk expression in adult mouse brain.
Figure 5B:
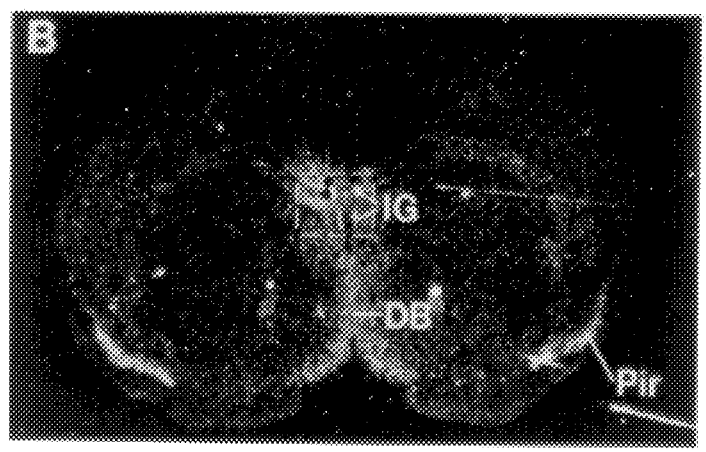
Figure 5C:
Figure 5D:
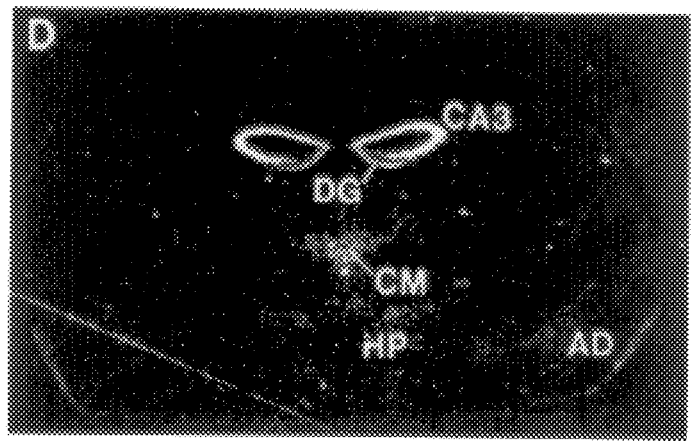
Figure 5E:
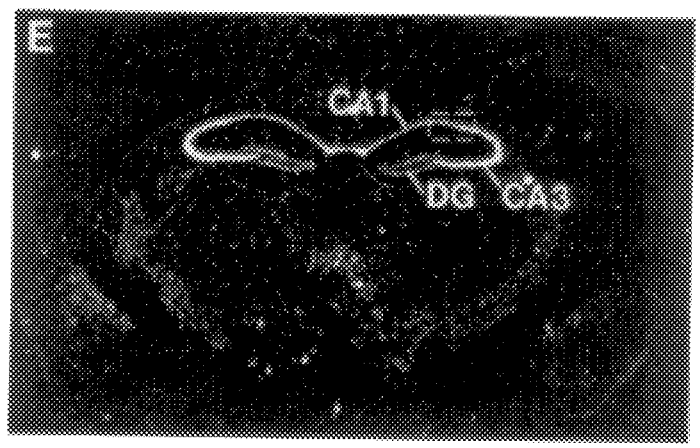
Figure 5F:
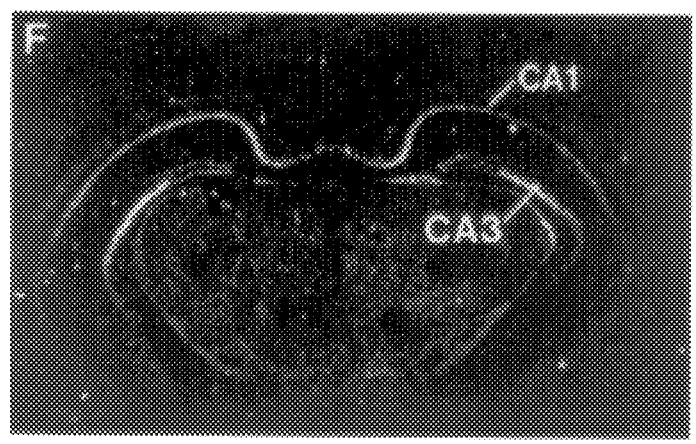
Figure 5A:
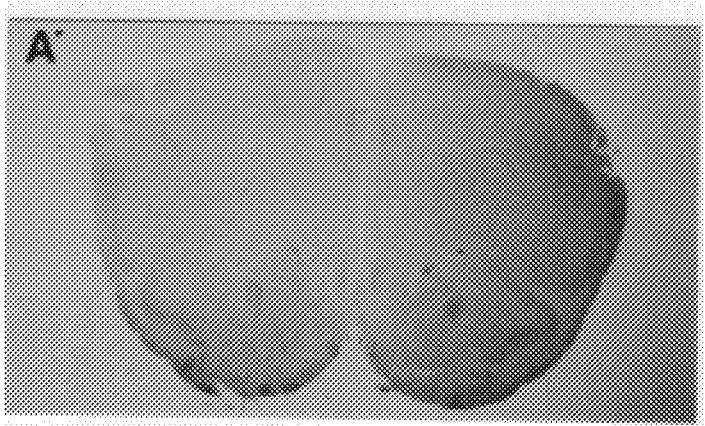
Figure 5B:
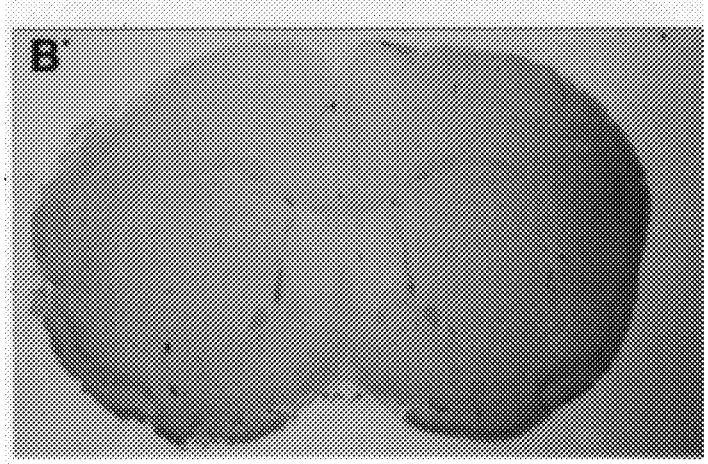
Figure 5C:
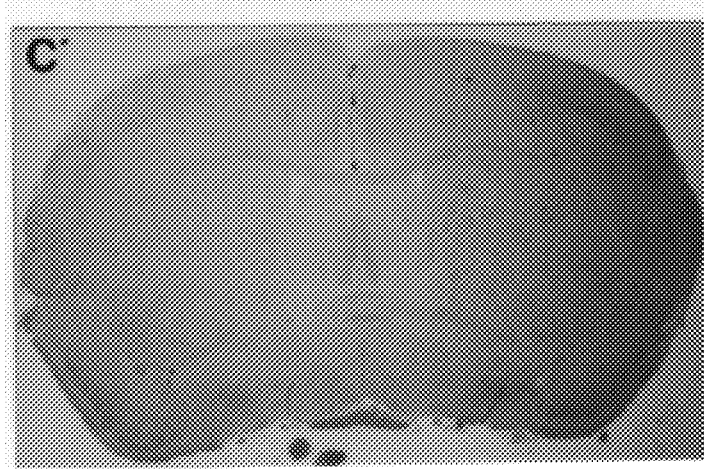
Figure 6A:
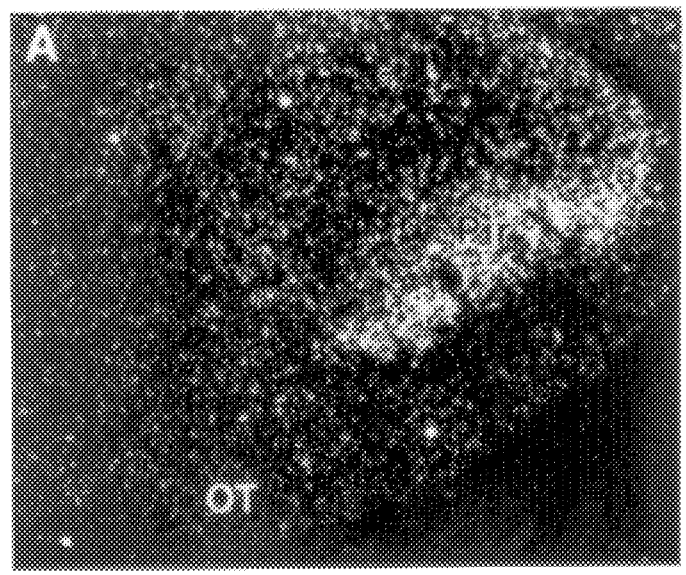
Figure 6B:
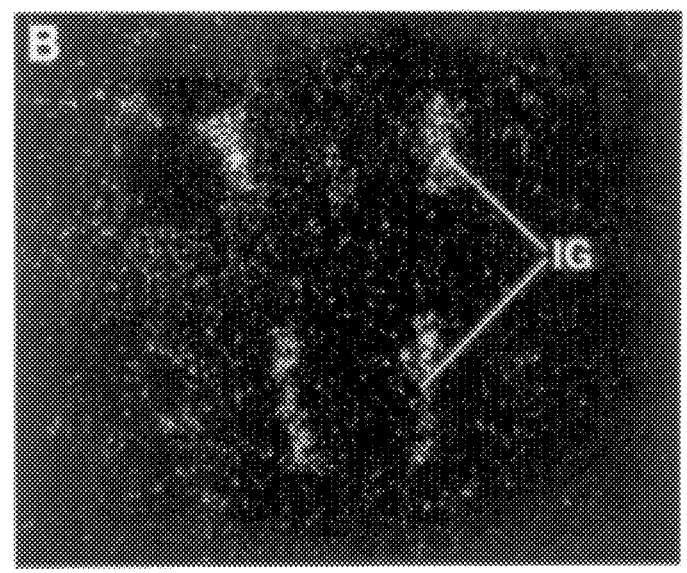
Figure 6C:
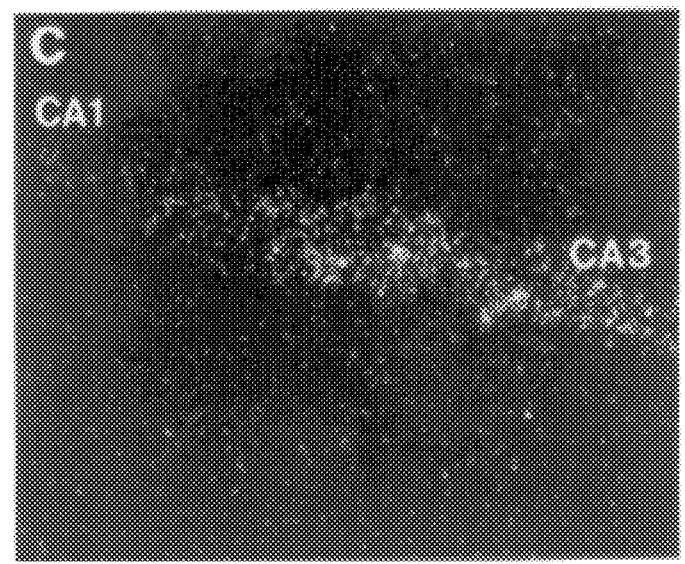
Figure 6A:
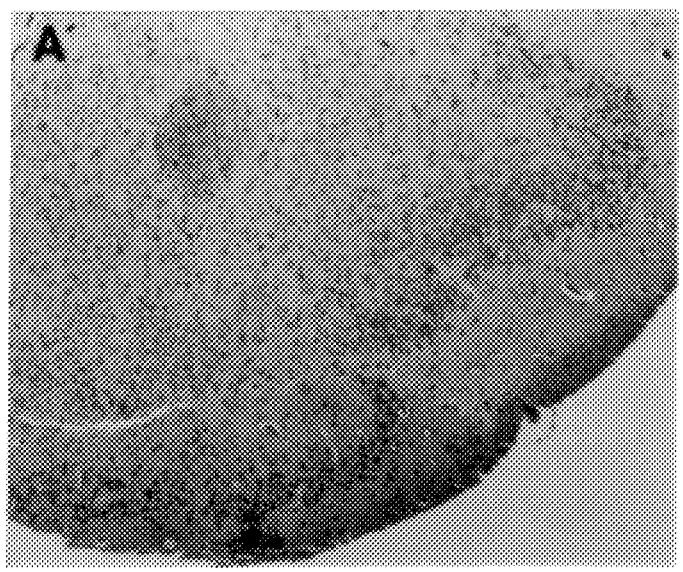
Figure 6B:
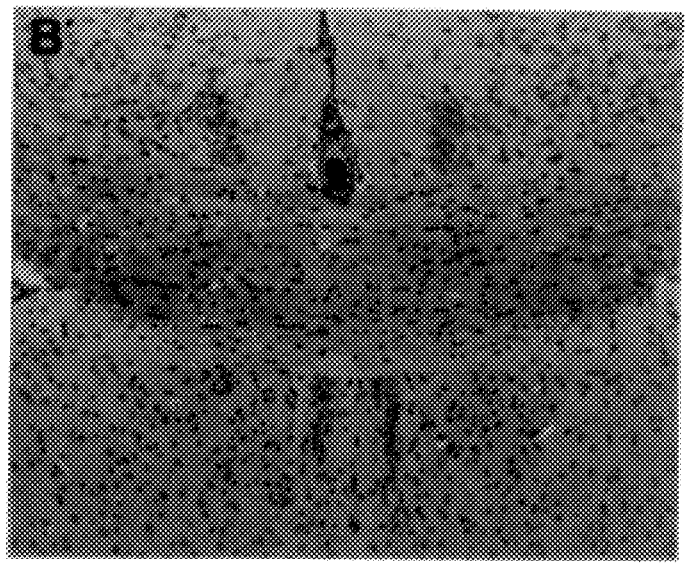
Figure 6C:
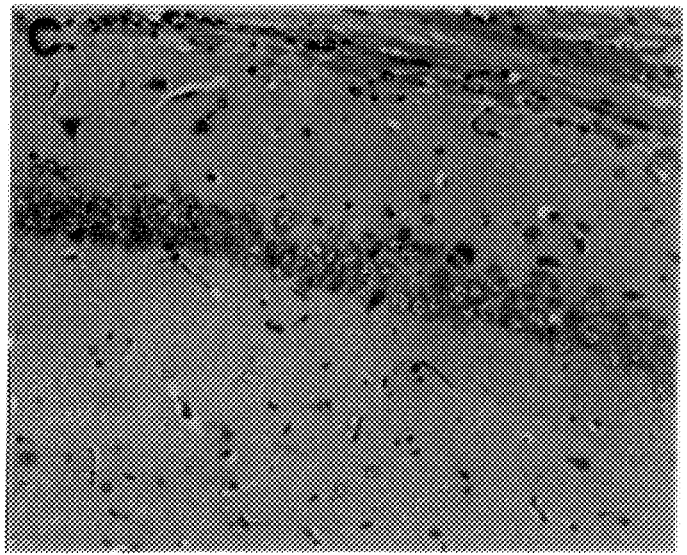

Evaluation of a series of coronal sections hybridized using the [$^{35}$S] -labeled anti-sense Bsk riboprobe revealed that although there was hybridization within many regions of the brain, several areas exhibited more intense hybridization (FIG. 5A–F, 5A'–F'). As a negative control, corresponding coronal sections were hybridized to a sense probe and revealed no distinguishable pattern of hybridization. In the rostral telencephalon the highest levels of hybridization were present in the tenia tecta (hippocampal rudiment) and the pyramidal cell layer (PLC) of the piriform cortex with no labeling in the adjacent pyramidal cell layer of the olfactory tubercle (FIG. 5A–FIG. 6A). The infralimbic cortex and anterior cingulate cortex exhibited moderate levels of hybridization with somewhat lower levels in the prefrontal cortex (FIG. 5A). At the level of the septum and anterior commissure the highest degree of hybridization was still observed in the PCL of the piriform cortex, the tenia tecta, and the indusium griseum (FIG. 5B, FIG. 6B). Elevated levels of hybridization were also present in the medial septum and vertical and horizontal limbs of the diagonal band within the area that contains the cholinergic basal forebrain neurons (FIG. 5B–C). Coronal sections through the rostral end of the hippocampus demonstrated highly specific hybridization in both the large CA3 pyramidal cells and smaller CA1 pyramidal cells of Ammon's horn with a lower signal in the granule cell layer of the dentate gyrus (FIG. 5D–E, FIG. 6C). Sections through the amygdaloid complex demonstrated that there was moderately high hybridization in both the basolateral and medial amygdaloid nuclei (FIG. 5D–E). This level of signal was somewhat lower than that observed in the PCL of the piriform cortex or in the pyramidal cells of Ammon's horn and dorsal subiculum. In the caudal telencephalon the highest hybridization was still observed in the subiculum and CA1-3 pyramidal cells of the dorsal hippocampus with somewhat less hybridization apparent in these regions as they extend into the ventral hippocampus (FIG. 5F). Although some hybridization was observed in corpus callosum and anterior commissure (FIG. 5B–C), a similar signal was observed in the hybridization with the control probe. Thus the hybridization in these regions may not be specific.

Figure 7A:
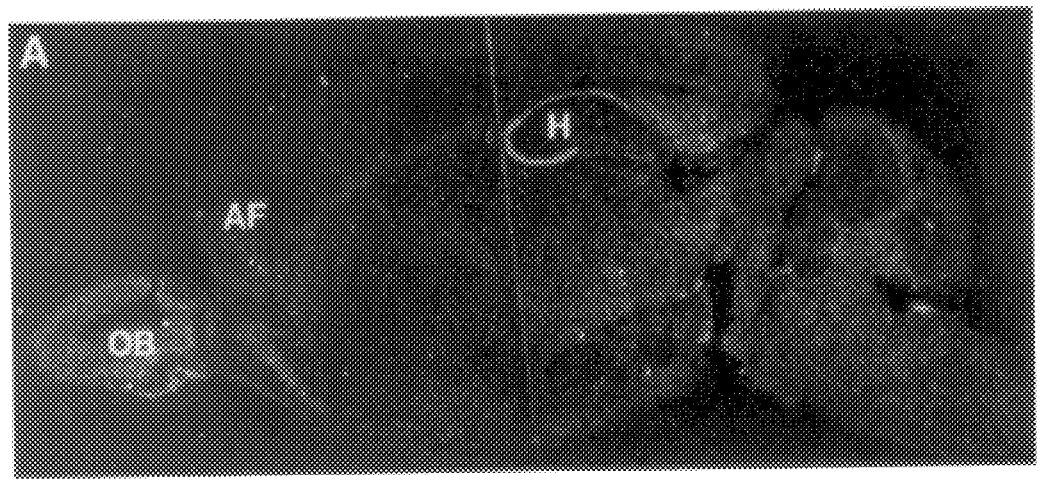
FIGS. 7A–B, 7A'–B' shows sagittal view of Bsk expression in adult brain. FIGS. A and A' show the dark and bright field view of neighboring parasagittal sections hybridized with Bsk probe or silver-stained respectively.
Figure 7B:
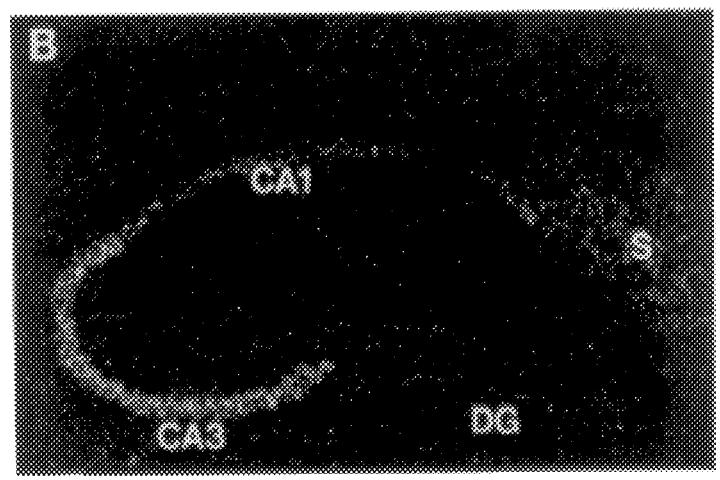
Figure 7A:
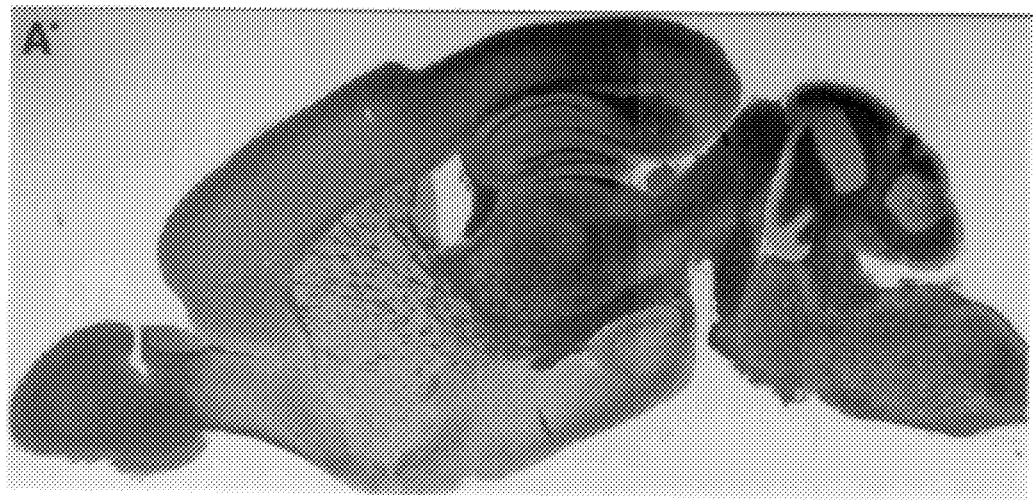
Figure 7B:
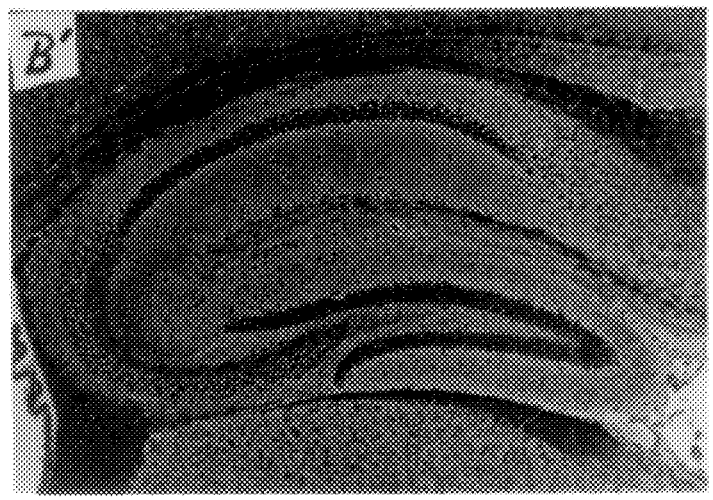

Horizontal and sagittal sections (FIG. 7A–B, 7A'–B') confirmed this regional distribution of hybridization intensity (FIG. 7A–B, 7A'–B'). In addition, sagittal sections, which included portions of the olfactory bulb, exhibited extensive hybridization in the mitral cell layer and the granule cell layer of this structure (FIG. 7A). Thus, although many areas of the brain exhibited some hybridization with Bsk probe, the overall distribution of regions with the highest hybridization signal appeared to be associated with several of the major subcomponents of the limbic system (MacLean, (1990): In Maclean PD, (eds) "Triune brain in evolution: role in paleocerebral functions" Plenum Press, pp269–313) such as the hippocampus, amygdala, piriform cortex, and medial septum/diagonal band of Broca.

Figure 8A:
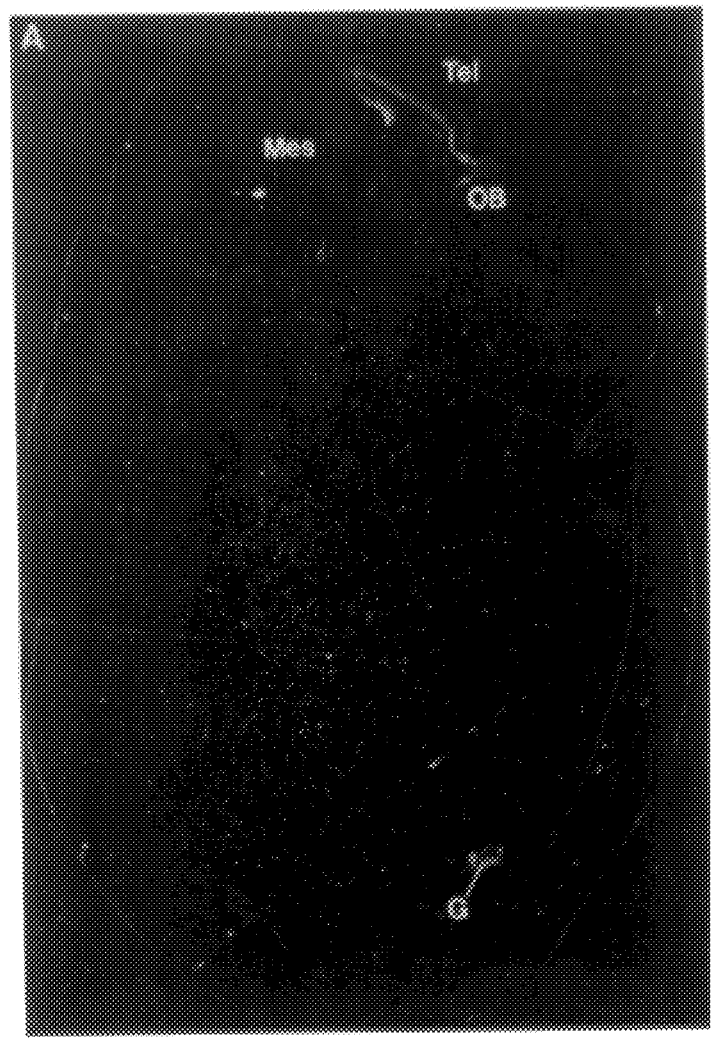
FIGS. 8A–B, 8A'–B' shows Bsk expression in mouse embryo. FIGS. A and A' show the dark and bright field view of the parasagittal sections of a 16.5 day mouse embryo. FIGS. B and B' show detailed dark and bright field views of the embryonic telencephalon respectively. Tel: telencephalon; Mes: mesencephalon; G: gonadal tissue; E; external zone; I: intermediate zone; S: subventricular zone; V: ventricular epithelium. Magnification 12.5×.
Figure 8B:
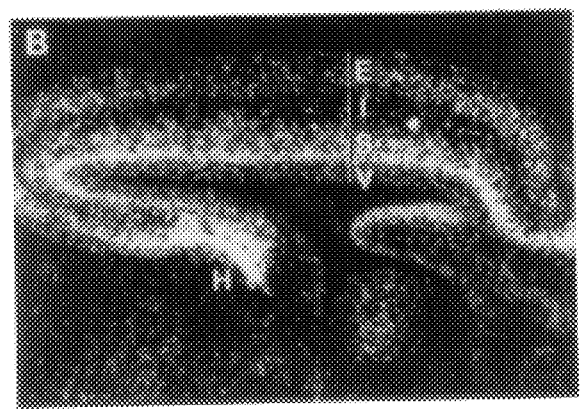
Figure 8A:
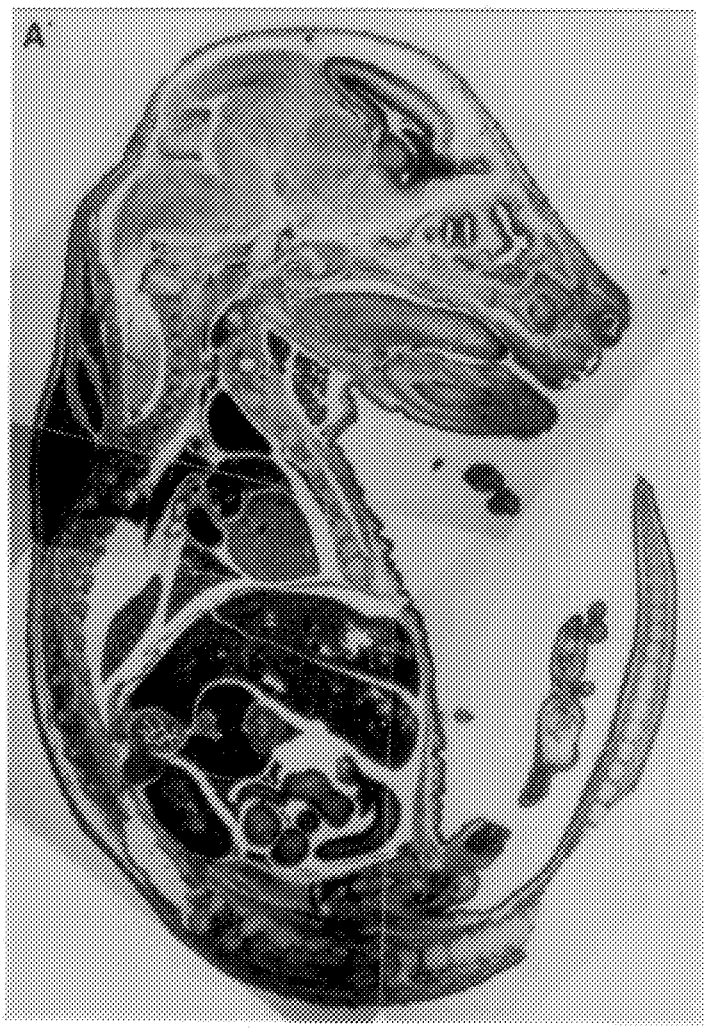
Figure 8B:

In situ hybridization analysis of 16.5 day mouse embryos utilizing the Bsk riboprobe described above, revealed that Bsk expression is confined to the embryonic brain in the telencephalon and in the olfactory bulb (FIG. 8A–B, 8A'–B'). The highest level of expression was found in the subventricular zone and in the external layer of the cortex. This pattern of expression suggests that Bsk is expressed mainly in the postmitotic neurons when they migrate away from the ventricular zone.

In situ hybridization in the adult brain showed that expression is predominantly in the hippocampus and other limbic structures with particularly high levels found in the hippocampal CA3 area. Moderate levels of expression was also observed in the medial dorsal thalamic nucleus, ventral medial and lateral nucleus of the hypothalamus (FIG. 5–E). These structures have extensive connections with the limbic system and are considered by some authors (MacLean, (1990). In Maclean PD (eds) "Triune brain in evolution: role in paleocerebral functions" Plenum Press, pp269–313; Levitt P (1984) *Science* 223: 299–301) as part of the limbic system. These results indicate that Bsk expression is relatively restricted to the limbic system, in sharp contrast with the expression patterns of trk-B (Klein et al., (1990) *Development* 109:845–850) and trk-C (Tessarollo et al., (1993): *Development* 118:463–475) which are widely expressed both in the central and peripheral nervous systems.

The expression of the growth factor receptor in a particular type of neuron is an indication of its trophic function in these neurons. The expression of the NGF receptor trk in the sensory, cranial, and spinal ganglia (Martin-Zanca et al. (1990) *Genes & Development* 4:683–694), and in the adult basal forebrain cholinergic neurons (Holtzman et al., (1992): *Neuron* 9:465–478) correlates well with the response of these neurons to NGF (Levi-Montalcini R, (1987) *Science* 237:1154–1162). Therefore, the receptor for limbic neuron survival factors should be expressed in the limbic neurons and possibly also in developmentally or functionally related neurons. Although the BDNF receptor trk-B, and NT-3 receptor trk-C are expressed in the hippocampus, they are also widely expressed elsewhere, in both the central and peripheral nervous systems (Klein et al. (1990) *Development* 109:845–850; Tessarollo et al. (1993) *Development* 118:463–475). Thus, like FGF, the function of BDNF and NT-3 in hippocampus can not explain the unique aspects of hippocampal neuronal structure and function.

Bsk is predominantly expressed in the hippocampus and its associated limbic structures. Therefore it may function as a growth or trophic factor receptor for neurons of the limbic system, particularly for the hippocampal CA3 pyramidal neurons since the expression is highest in these cells. Specific degeneration of CA3 hippocampal neurons is associated with pharmacologically intractable partial complex seizures (Nadler JV (1989): Seizures and neuronal death in the hippocampus. In Chan-Palay V, Koehler C (eds): "The Hippocampus-New Vistas" Alan R. Liss, Inc., pp 463–481). The high level of Bsk expression in the limbic system suggests it may be important for the function and survival of limbic neurons.

EXAMPLE 4

Study Of the Biolocrical Function of Bsk Methods
[$^{35}$S] Methionine/Cysteine Labeling of Proteins Cells including, but not limited to, PC12 cells, and NIH/3T3 cells, are grown to 80% confluence in 100-mm tissue culture dishes, washed twice in methionine/ cysteine-free DMEM, (Dulbecco's Modified Eagle Media) starved in the same medium supplemented with 5% dialyzed fetal calf serum for 30 min, and then incubated for 2, 4, or 8 hours in the same medium with Translabel (Amersham, 70% [$^{35}$S] cysteine). The labeled cells will be lysed and immunoprecipitated as described below.

Cell Surface Labeling

Cells expressing the chimeric receptor will be grown to 80% confluence on 175-cm$^2$ flasks. Cells are washed twice with PBS, removed gently will a cell scraper, and resuspended in PBS containing 6 U of lactoperoxidase, 20 U of glucose oxidase and 2 mCi of [$^{125}$I]. After 0, 10, and 20 min, 140 ul of 1M glucose will be added. At 30 min, the reaction is stopped by three washes in PBS. The cells are then lysed and immunoprecipitated using appropriate antibodies.

Preparation of Cell Extracts and Immunoprecipitation

Cells will be washed in Wash Buffer (HEPES 50 mM, pH 7.4, NaCl 150 mM, glycerol 10%, EDTA 10 mM, NaF 100 mM, vanadate 2 mM, Na$_4$P$_2$O7 10 mM, trypsin inhibitor 1000 U/ml, PMSF 1 mM, aprotinin 1 mM, leupeptin 20 uM); the cells are lysed for 30 min at 4° C. in 200 ul of lysis buffer (Wash Buffer containing 1% Triton X-100) and centrifuged for 30 min at 150,000 g in a Beckman TL-100 ultracentrifuge. The extracts are then cleared twice by 15 min incubation with protein A Sepharose (40 ul of 10% gel for 200 ul of cell extracts). After a 5 min. centrifugation, supernatants are mixed with appropriate antibodies adsorbed on protein-A-Sepharose and incubated for 2 h at 4° C. with agitation. The samples are then centrifuged for 30 sec and the pellets are washed 6 times (3 times with Wash Buffer, 3 times with Wash Buffer supplemented with 500 mM NaCl, 0.1% Triton X-100, 0.1% SDS). The washed pellets are then resuspended in SDS-PAGE buffer and subjected to SDS-PAGE analysis. Labeled proteins are visualized by autoradiography.

Ligand Binding Study

Cells are grown in 100 mm culture dishes in DMEM to 80% confluence and then washed with PBS and incubated with 5 ml of 25 mM EDTA in PBS for 2 min. Cells are then removed from the plate, washed once with Binding Buffer (100 mM HEPES, pH 7.6, 120 mM NaCl, 5 mM KCl, 1.2 mM MgSO4, 1 mM EDTA, 10 mM glucose, 15 mM sodium acetate, 1% dialyzed BSA), and resuspended in 5 ml of Binding Buffer to determine the cell number. 400 ul of this cell suspension is then incubated with [$^{125}$I] -M-CSF (5 pM) and increasing concentrations of unlabeled M-CSF (from 0 to 10$^{-6}$M) in a total volume of 500 ul for 90 min at 15° C. After incubation, cells are washed with Binding Buffer. Free [$^{125}$I] -MCSF is removed by six washes in Binding Buffer. Finally, the [$^{125}$I] radioactivity bound to the cells is determined in a γ-counter. Data obtained will be analyzed by the method of Scatchard (Scatchard, (1949) *Ann. N.Y. Acad. Sci.* 51:660–672).

Thymidine Incorporation Assay

Confluent cell monolayers in 12-well culture dishes will be grown to quiescence in medium containing 0.5% fetal bovine serum for 24 hours (h). DNA synthesis will be stimulated by adding various amount of M-CSF. Eighteen hours later, cells will be labeled for 4 h with 0.5 uCi [methyl-$^3$H] thymidine at 3 TBq/mmol, then washed three times with ice cold PBS, incubated with 1 ml of 10% trichloroacetic acid for 30 min, and washed twice with the same solution at 4° C. Cells will be then solubilized in 0.5 ml of 0.2N NaOH, 1% SDS for 1 h at 37° C. and the lysate will be brought to neutral pH with Tris buffer. The incorporated radioactivity will be determined in a liquid scintillation counter.

Construction of Recombinant Adenovirus (Ad-CR)

The recombinant adenovirus is constructed by in vivo homologous recombination between an adenoviral vector containing the chimeric receptor and an adenovirus deletion mutant Ad1327 genomic DNA (Stratford-Perricaudt et al., (1992) *J.Clin Invest* 90:626–630) in 293 cells which expresse adenoviral early genes (Graham et al., (1977) *J. Gen Virol* 36:59–72). Briefly, 293 cells are cotransfected with 5 ug of linearized plasmid pAd-CR and 5 ug of the large Cla I fragment (2.6–100 mu) of Ad5 DNA. After overlaying with agar and incubating for 10 days at 37° C., plaques containing recombinant adenoviruses are isolated and amplified in 293 cells, viral DNA is purified, and recombinant adenovirus plaques containing the Bsk chimeric receptor are identified by restriction cleavage and Southern analysis.

Hippocampal Neuron Cultures

Hippocampi are dissected from E18 rat embryos and collected in F10 medium (Gibco). The tissues are minced, rinsed twice with F10 medium, and the cells are dissociated by gentle trituration and collected by low speed centrifugation (500 rpm) for 30 sec. The pellet is washed again in the same medium by resuspension and centrifugation. The cell pellets are resuspended in MEM supplemented with 10% fetal calf serum, 2 mM glutamine, 25 U/ml Penicillin and 25 ug/ml Streptomycin and plated onto polyorthinine (10 ug/ml) and laminin (10 ug/ml) coated 6 mm microtiter wells at a density of 70,000 cells/cm$^2$. Six hours following the plating of cells, the medium is changed to a serum-free medium containing 25 ug/ml insulin, 100 ug/ml transferrin, 60 uM putrescine, 20 nM progesterone, 30 nM selenium, 6 mg/ml glucose (Lu et al., (1991) *Proc. Natl Acad Sci USA* 88:6289–6292 and penicillin-streptomycin (25 U/ml and 25 ug/ml, respectively), and infected with the viruses at a moi of 10, 5, 2, and 1 respectively. M-CSF is added at the same time. Medium is changed every 3–4 days with the readdition of fresh factors.

Measurement of Neurofilament Protein

Cells are fixed with 4% (v/v) paraformaldehyde for 4 h at 4° C., permeabilized with 0.1% (v/v) Triton X-100 in PBS for 15 min, and blocked with 10% FCS in PBS for 1 h. The cells are then incubated with anti-neurofilament 200 antibody for 1 h at room temperature, washed twice with PBS containing 10% FCS, and incubated with the secondary antibody (horseradish peroxidase-conjugated) for 1 h. Following sequential washing with PBS and water, the cells are incubated with 0.2% (w/v) O-phenylenediamine and 0.02% (v/v) $H_2O_2$ in citrate buffer (50 mM) for 30 min. The reaction is stopped by adding an equal volume of 4.5M $H_2SO_4$. Product formation will be quantitated by reading the optical density of the reaction product at 492 nm.

Immunocytochemistry

Cells are rinsed twice with PBS, fixed with 4% paraformaldehyde for 30 min at room temperature, and blocked with 10% FCS in PBS containing 0.1% Triton X-100. The cells are then incubated with the primary antibodies overnight at 4° C., washed with 0.1% Triton X-100 in PBS three times and incubated with Texas Red conjugated secondary antibodies for 90 min at room temperature. The cells are washed again and positive cells are visualized under a fluorescent microscope.

Measurement of High-Affinity Uptake of GABA

High-affinity GABA uptake will be measured as described (Ip et al., (1991) *J. Neuro Sci.* 11:3124–3134). Cells are washed in the GABA uptake buffer containing 140 mM NaCl, 2.5 mM KCl, 1 mM $KH_2PO_4$. 1 mM $Na_2HPO_4$, 6 mg/ml glucose, 1 mM $MgCl_2$, 1 mM $CaCl_2$, and 0.1% BSA. Following washing, cells are incubated in the GABA uptake buffer for 5 min at 37° C. [$^3$H]- GABA is then added to a final concentration of 12 nM, and incubated at 37° C. for 10 min. Cells are kept on ice and washed three times with the uptake buffer. Cells are then solubilized with 0.14N NaOH for 2 h at room temperature, and [$^3$H]-GABA in the extract is counted. Update of GABA into non-neuronal cells is inhibited by the addition of 2 mM beta-alanine, whereas uptake specific for neurons is verified by inhibition with nipecotic acid at 1 mM. Specific neuronal GABA uptake is determined as GABA uptake that is blocked in the presence of 1 mM nipecotic acid.

Placental Alkaline Phosphatase Activity Assay

The assay is performed by heating a portion of the supernatant at 65° C. for 10 min to inactivate background phosphatase activity and then measuring the optical density at 405 nm after incubation with 1M diethanolamine (pH 9.8), 0.5 mM $MgCl_2$, 10 $\mu$M L-homoarginine (a phosphatase inhibitor), 0.5 mg/ml BSA, and 12 mM p-nitropheyl phosphate. The highest alkaline phosphatase-expressing clone will be selected for the purification of AP-tag-Bsk fusion protein. To concentrate and purify AP-tag-Bsk protein, the supernatant will be incubated with a monoclonal antibody to placental alkaline phosphatase coupled to CNBr-activated Sepharose. Specifically bound protein will be eluted with 144 mM NaCl, 1 mM $MgCl_2$, 1 mM $CaCl_2$, 50 mM sodium citrate (pH 2.5), and will be then immediately neutralized with 1M HEPES (pH 8.0). The purified protein will be used as a probe to screen a brain expression library.

Library Screening Using AP-tag Bsk

A brain expression cDNA library will be plated at a density of 50,000 pfu per 150 mm plate. Duplicate filters will be lifted from the plates and rinsed in TBST. The filters are then blocked with TBST with 10% goat serum, rinsed once in TBST, and incubated in TBST with APtag-Bsk probe for 3 hours. The Filters are then washed in three changes of TBST, 3 min each. The positive clones will be detected by color formation when the filters are incubated with alkaline phosphatase substrates 5-bromo-4-chloro-3-indolyl phosphate (BCIP, 0.017 mg/ml) and nitrobluetetrazolium (NBT, 0.33 mg/ml) in 100 mM Tris-HCl (pH 9.5), 100 mM NaCl, 5mM $MgCl_2$. A non-specific alkaline phosphatase inhibitor, L-homoarginine (10 mM), will be added if required.

Construction Of a Chimeric Receptor

To construct a M-CSFR/Bsk chimeric receptor, a combination of restriction enzyme digestion and PCR approaches will be used to ligate the M-CSFR extracellular domain and the Bsk transmembrane and intracellular domains (M-CSFR/Bsk). An alternative construct, M-CSFR/Bsk 2, would contain M-CSFR extracellular and transmembrane domains and Bsk intracellular domain.

The chimeric receptor will be expressed under the LTR promoter in the pMEX expression vector (Oskam et al., (1988) *Proc. Natl Acad Sci. USA* 85:2964–2968) in NIH/3T3 cells to study whether it has a mitogenic effect and in PC12 cells to study whether it induces differentiation. The expression cassette pMEX-CR (CR for chimeric receptor), will be cotransfected with pSV2Neo. Neo-resistant colonies will be grown up and tested for the expression of the chimeric receptor using immunoprecipitation or Western blot analysis (Ausubel et. al., (1987) In "Current Protocols in Molecular Biology" John Wiley and Sons, New York, N.Y.). To study if the chimeric receptor is properly localized in the cytoplasmic membrane, cell surface labeling will be performed (see Methods). The labeled cells will be lysed and immunoprecipitated with either Bsk- or M-CSFR-specific antibodies. If the receptor is properly localized on the cell surface, a positive labeling of the chimeric product should result.

To examine the binding property of the chimeric receptor to M-CSF, [$^{125}$I]-MCSF will be used to bind intact transfected or control cells. To measure the receptor binding affinity and specificity, the concentration of MCSF needed to cause 50% inhibition of maximal [$^{125}$I] -MCSF binding to the cells will be determined (IC50). Scatchard analysis will be performed on the binding competition data (Scatchard, (1949) *Ann. N.Y. Acad Sci* 51:660–672) and the dissociation constant (Kd) will be calculated. Cells transfected with vector alone will be used as controls.

To study if the chimeric receptor functions properly, the chimeric receptor will be immunoprecipitated with either M-CSFR or Bsk-specific antibodies from M-CSF-stimulated cells for various times, using unstimulated cells as a control. The precipitated receptor will be analyzed by the Western blot technique with anti-phosphotyrosine antibody to examine the activation of the receptor tyrosine kinase.

The biological effects of the stimulation of the chimeric receptor with M-CSF will be studied in NIH/3T3 cells by stimulation of DNA synthesis under low serum (calf serum at 0.3%) conditions. To determine the functions of Bsk in neuronal differentiation, the effects of the chimeric receptor activation on neurite outgrowth in PC12 cells will be studied.

Constitutively Active Bsk Receptor

As an alternative approach to study the biological function of the Bsk kinase is to create mutant Bsk kinases which are constitutively active. Constitutively active Bsk receptor will be generated and their effect on NIH/3T3 and PC12 cells studied.

The selection for receptor activation is transforming activity. However, this may select for mitogenic function of the mutated receptor rather than the true biological function. Although there is no clear evidence to rule out this possibility, studies of trk family receptors indicate that the mitogenic and differentiation functions of the receptors are similar (Klein et al., (1991) *Cell* 66:395–403; Glass et al., (1991) *Cell* 66:405–413). The phenotypes of receptor activation are determined by the cell types in which the receptor is expressed (Squinto et al. 1991 *Cell* 65:885–893; Glass et al., (1991) *Cell* 66:405–413); Klein et al., (1991) *Cell* 66:395–403). Thus, trk activation by NGF in PC12 cells induces neurite outgrowth and in NIH/3T3 cell induces transformation. Therefore, it is likely that this selection will give biologically relevant mutations. In addition, mutated, especially truncated Bsk may have a different function from that of the ligand-activated wild type Bsk kinase because of possibly different subcellular localization and/or lack of certain substrate interaction sites. Studies with tpr-trk, which is an activated from of trk with a substitution of the N-terminal domain by tpr sequences, showed that it retains the function of ligand-activated trk protein (Greco et al., (1993) *Cell Growth and Diff* 4:539–546). Tpr-trk induces neurite outgrowth when introduced in PC12 cells (Greco et al., (1993) *Cell Growth and Diff* 4:539–546. Therefore, mutation- and ligand-activated receptors do share at least part of the functions. Furthermore, the possible differences of subcellular localization and substrate interaction sites between the mutation- and ligand- activated Bsk receptors will be minimized by using only the viruses which have the least amount of structural changes in Bsk.

Effect of the Chimeric Receptor in Hippocampal Neurons

A vector system which is based on an adenovirus (Stratford-Perricaudet et al., (1992) *J Clin Invest* 90:626–630) will be used to deliver CSFR/Bsk into hippocampal neurons from E18 rat embryos. This vector has been used successfully in the nervous system and no cytotoxicity was observed (Le Gal La Salle at al., (1993) *Science* 259:988–990). In addition, long term expression of genes was achieved with this vector (Le Gal La Salle et al., (1993) *Science* 259:988–990).

To clone M-CSF/Bsk chimeric receptor into an adenoviral promoter, a vector plasmid, pAd-CR, containing a chimeric receptor expressing cassette driven by M-MLV LTR promoter will be constructed. The cassette will be bordered at the 5' end by the left end (map unit 0–1.3) of adenovirus type 5 (Ad5) and at the 3' end by sequences from mu 9.4–17 (Blg II - Hind III fragment of Ad5) to allow homologous recombination with the adenoviral genome to generate recombinant virus (see Methods section). The resulting recombinant virus will lack the early gene E1 and therefore will be replication incompetent except when provided with E1 function in 293 cells (Graham et al., (1977) *J Gen Virol* 36:59–72.

To study the effect of Bsk chimeric receptor on the survival of hippocampal neurons, hippocampal neuron culture will be established in polyornithine- and laminin-coated plastic dishes in MEM supplemented with 10% fetal calf serum (FCS) and glutamine and infected with Ad-CR or control virus. Later, the medium will be changed to a serum-free medium containing hormone supplements (see Methods). M-CSF will be added at this time. After various times of treatment, cells will be stained with antibody against neuron-specific enolase to identify neurons in the culture. The number of neurons in cultures infected with virus containing M-CSFR/Bsk or with viral vector only will be compared to determine the effect of MCSF stimulation on the survival of specific neurons. Parallel infected cultures will be studied for Bsk protein expression at various time points using Western blot or immunoprecipitation, and for ligand-dependent activation of tyrosine kinase activity of the chimeric receptor (Kaplan et al., (1991) *Nature* 350:158–160; Klein et al., (1991) *Cell* 65:189–197).

To examine if Bsk has any effect on the neurite outgrowth of the hippocampal neurons, changes in the level of neurofilament protein upon M-CSF treatment will be examined. Hippocampal neurons will be infected with virus carrying M-CSF/Bsk and treated with various concentrations (0.001–10ng/ml) of M-CSF for 8 days and neurofilament protein levels will be measured by ELISA (see Methods) Neurons infected with vector alone will be used as controls. To delineate which neuronal population which respond to Bsk kinase activation, the effect of M-CSF treatment of neurons expressing the chimeric receptor on the number of GABAergic-and calbindin-positive neurons will be studied. Infected neurons will be treated with various concentrations of M-CSF (0.001–100ng/ml). After 8 days of treatment, cells will be stained with anti-GABA receptor or anti-calbindin antibodies to study the effect of Bsk activation on the survival of various neuronal populations. In addition to the immunostaining with different antibodies, we will study the changes of the high-affinity update for GABA after various times of M-CSF treatment. [$^3$H]-GABA binding by the neurons in cultures infected with the virus expressing the chimeric receptor or with control virus will be compared (see Methods). β-alanine will be used to inhibit the uptake of GABA into non-neuronal cells (Ip et al., (1991) *Neurosci* 11:3124–3134).

An alternative vector system which is based on a herpes virus may also be used to deliver CSFR/Bsk into hippocampal neurons (Anderson et al., (1992) *Human Gene Therapy* 3:487–499; Fink et al., (1992) *Human Gene Therapy* 3:11–19).

EXAMPLE 5

Isolation of the Bsk Ligand

Screening of a cDNA Expression Library for Bsk Ligand Using an Extracellular Domain-Alkaline Phosphatase Fusion Protein as a Probe To construct a fusion protein between the extracellular domain of Bsk and the secreted placental alkaline phosphatase (SEAP), a vector named APtag-1, constructed by Flannagan and Leder (1990) *Cell* 63:185–194 will be used. APtag-1 contains a set of restriction sites for the insertion of the region of the Bsk cDNA encoding the extracellular domain. Downstream of the insertion sites is the full length sequence of SEAP, which will be fused to the upstream sequence.

To generate a Bsk receptor fusion protein, the 5' end of the Bsk cDNA sequence will be inserted into APtag-1, including sequences encoding the Bsk secreation signal peptide and the entire extracellular domain, ending immediately before the first hydrophobic amino acid of the transmembrane region. The resulting plasmid will therefore encode a fusion protein with the Bsk extracellular domain joined to SEAP. The fusion protein will be expressed from a Moloney Murine Leukemia virus LTR promoter. The fusion construct will be transfected into NIH/3T3 cells which have been shown to express high levels of an APtag-Kit fusion protein (Flanagen and Leder, (1990) (*Cell* 63:185–194). The fusion construct will be cotransfected with a selectable marker plasmid pSV2neo, and selected with G418 (400–800 ug/ml). Neo-resistant colonies will be grown in 96-well plates and screened for secretion of SEAP activity into the media (see Methods section, example 4). The fusion protein will be concentrated, purified and used as a probe to screen a cDNA expression library from mammalian brain, preferably mouse.

Three types of positive clones are expected: 1) clones having background alkaline phosphatase activity; 2) clones which bind non-specifically to the fusion protein; and 3) clones encoding the putative Bsk ligand. Background phosphatase clones will be positive without the added probe in the presence of alkaline phosphatase substrates. To distinguish the specific from the non-specific interacting clones, extracts from bacteria expressing these clones will be used to stimulate the tyrosine kinase activity of Bsk in a Bsk expressing NIH/3T3 cells. Only the ligand will be able to stimulate activation of Bsk tyrosine activity.

Is it preferable to produce the receptor probe in NIH/3T3 cells rather than bacteria to receive proper glycosylation of the Bsk extracellular domain. It has however been demonstrated that glycosylation of growth factors is often not necessary for their activity. For example, M-CSF (Metcalf, (1986) *Blood* 67:257–267 and NGF (available from Boehringer Mannheim) produced in bacteria are biologically active. Therefore, the glycosylated receptor probe should interact properly with its ligand synthesized by *E. coli* in a phase plaque during the screening.

In addition to using the Ap-tagged Bsk probe to screen for putative ligand in vitro, the probe can also be used in histological staining mammalian on brain sections to localize expression of the ligand. Determination of the loci of express in of the Bsk ligand will allow for biochemical purification of the ligand from that tissue cell source further for analysis.

Functional Screening of Bsk Ligand

An alternative approach to isolate the Bsk ligand is to utilize a functional screening approach. Full length cDNA of Bsk will be cloned into an expression vector pMEX under a MMLV LTR promoter. The Bsk expression vector will be co-transfected into NIH/3T3 cells together with pSV2Hygro containing a hygromycin β-phosphotransferase gene which confers hygromycin resistance (Gritz and Davies, (1983) *Gene* 25:179–188). The transfected cells with be selected with hygromycin B at a concentration of 350 ug/ml. The resistant clones will be grown in 12-well plates and screened for Bsk expression with anti-Bsk antibody by Wester blot analysis.

The vector system developed by Miki et al. (1989) *Gene* 83:137–146 will be used to construct a directional eukaryotic cDNA library from mouse brain mRNA. The vector has a MMLV LTR promoter for the expression of cDNA inserts and a SV40 early promoter-driven Neo gene as a selectable marker. In addition, this vector contains a pBR322 replication origin, and the cDNA inserts of interest can be obtained easily by Not I digestion of crude Lambda DNA preparations and ligation followed by transfection of bacterial cells. The cDNA library will be constructed as described in detail by Miki et al. (1989) *Gene* 83:137–146.

The cDNA library will be transfected into Bsk-expressing NIH/3T3 mouse embryo fibroblasts. Foci from transfected cells will be isolated and tested for Neo resistance to eliminate the background transformation in NIH/3T3 cells. Genomic DNA from each Neo-resistant transformant will be cleaved by Not I which will release the plasmid. Digested DNA will be ligated under diluted conditions and used to transform competent bacteria. Plasmid DNA from each focus will be purified and transfected in NIH/3T3 cells with or without Bsk expression. The transformation by the putative Bsk ligand but not other oncogenes is expected to be dependent on the present of Bsk expression. Putative clones will then be further analyzed by sequencing, the encoded protein purified and assayed for Bsk binding.

Although the present invention has been described on some detail by way of illustration and examples for purposes of clarity of understanding it will be obvious that certain changes and modifications may be practiced within the scope of the approached claims.

We claim:

1. An isolated nucleic acid sequence encoding a protein comprising the amino acid sequence shown in SEQ ID NO:2.

2. An isolated and purified sequence encoding Bsk and having the nucleic acid sequence shown in SEQ ID:1.

3. A recombinant expression vector comprising the nucleic acid sequence according to claim 2 or claim 1.

4. A host cell transformed or transfected with a recombinant expression vector according to claim 3.

5. A method of producing a recombinant Bsk protein, comprising:

(a) inserting the nucleic acid sequence shown in SEQ ID NO:1 into an expression vector;

(b) transfecting the expression vector into a host cell;

(c) culturing the host cell under conditions appropriate for amplification of the vector and expression of the protein; and (d) harvesting the protein.

6. The method of claim 5, wherein the expression vector is a eukaryotic expression vector or prokaryotic expression vector.

7. The method of claim 5, wherein the expression vector is a baculovirus vector.

8. The method of claim 5, wherein the host cell is a eukaryotic cell or prokaryotic cell.

9. The method of claim 5, wherein the eukaryotic cell is an insect cell.

10. An isolated and purified nucleic acid sequence encoding a part of Bsk and having the nucleic acid sequence selected from the group consisting of (a) nucleic acids 418 to 570 SEQ ID NO:1; (b) nucleic acids 571 to 1653 of SEQ ID NO:1; (c) nucleic acids 1654 to 1716 of SEQ ID NO:1; (d) nucleic acids 1717 to 3048 of SEQ ID NO:1; (e) nucleic acids 571 to 1335 of SEQ ID NO:1; (f) nucleic acids 1336 to 1653 of SEQ ID NO:1; and (g) nucleic acids 1717 to 1797 of SEQ ID NO:1.

11. An isolated and purified nucleic acid sequence encoding a part of Bsk and having the nucleic acid sequence selected from the group consisting of (a) 418 to 570 of SEQ ID NO:1; (b) 418 to 1335 of SEQ ID NO:1; (c) 418 to 1657 of SEQ ID NO:1; (d) 418 to 1716 of SEQ ID NO:1; (e) 418 to 1797 of SEQ ID NO:1; (f) 571 to 1335 of SEQ ID NO:1; (g) 571 to 1653 of SEQ ID NO:1; (h) 571 to 1716 of SEQ ID NO:1; (i) 571 to 1797 of SEQ ID NO:1; (j) 571 to 3048 of SEQ ID NO:1; (k) 1336 to 1653 of SEQ ID NO:1; (l) 1336 to 1716 of SEQ ID NO:1; (m) 1336 to 1797 of SEQ ID NO:1; (n) 1336 to 3048 of SEQ ID NO:1; (o) 1654 to 1716 of SEQ ID NO:1; (p) 1654 to 1797 of SEQ ID NO:1; (q) 1654 to 3048 of SEQ ID NO:1; (r) 1717 to 1797 of SEQ ID NO:1; (s) 1717 to 3048 of SEQ ID NO:1; and (t) 1798 to 3048 of SEQ ID NO:1.

12. A recombinant expression vector comprising at least one of the nucleic acid sequences of claim 10 or 11.

13. A host cell transformed or transfected with a recombinant expression vector according to claim 12.

14. An isolated and purified nucleic acid sequence encoding a part of Bsk amino acid sequence, said amino acid sequence being selected from the group consisting of: (a) 1 to 51 of SEQ ID NO:2; (b) 52 to 412 of SEQ ID NO:2; (c) 413 to 433 of SEQ ID NO:2; (d) 434 to 460 of SEQ ID NO:2; (e) 434 to 877 of SEQ ID NO:2; (f) amino acids 52 to 306 of SEQ ID NO:2; and (g) 307 to 412 of SEQ ID NO:2.

15. An isolated and purified nucleic acid sequence encoding a part of Bsk amino acid sequence, said amino acid sequence being selected from the group consisting of: (a) 1 to 51 of SEQ ID NO:2; (b) 1 to 306 of SEQ ID NO:2; (c) 1 to 412 of SEQ ID NO:2; (d) 1 to 433 of SEQ ID NO:2; (e) 1 to 460 of SEQ ID NO:2; (f) 52 to 306 of SEQ ID NO:2; (g) 52 to 412 of SEQ ID NO:2; (h) 52 to 433 of SEQ ID NO:2; (i) 52 to 460 of SEQ ID NO:2; (j) 52 to 877 of SEQ ID NO:2; (k) 307 to 412 of SEQ ID NO:2; (l) 307 to 433 of SEQ ID NO:2; (m) 307 to 460 SEQ ID NO:2; (n) 307 to 877 of SEQ ID NO:2; (o) 413 to 433 of SEQ ID NO:2; (p) 413 to 460 of SEQ ID NO:2; (q) 413 to 877 of SEQ ID NO:2; (r) 434 to 460 of SEQ ID NO:2; (s) 434 to 877 of SEQ ID NO:2; and (t) 461 to 877 of SEQ ID NO:2.

16. A recombinant expression vector comprising at least one of the nucleic acid sequences of claim 14 or claim 15.

17. A host cell transformed or transfected with a recombinant expression vector according to claim 16.

* * * * *

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
        ( A ) LENGTH: 4322
        ( B ) TYPE: NUCLEOTIDE
        ( C ) STRANDEDNESS: DOUBLE
        ( D ) TOPOLOGY: UNKNOWN ( x i ) SEQUENCE DESCRIPTION: SEQ ID NO:1:

-continued

| | | | | |
|---|---|---|---|---|
| AATTCGGCAC | GAGTGAAAGG | GAACCTTCAC | CACCACTCCG | 40 |
| AACCCTGGTG | GCACTTAAAA | AAAAAAAGA | AGAAGAAGAA | 80 |
| GAAGGGGGT | GCCAGAAAAA | GAAAAAGTCT | TAAAGGGCAA | 120 |
| AGAAGCGGGA | CTCCCGACCC | TCTACAGACC | CTTGACCGAG | 160 |
| CCCACCCAGG | ACTGTACTAG | CCATCAGAAC | TTCTAATTCA | 200 |
| TCTTATCCAA | CTGAAAGGGA | GGGCGACAGG | AGCCAGAAGC | 240 |
| AAACTTCTTC | AGCGGTCTCT | GCGGATCTGT | GGATTCCCGC | 280 |
| ATTTAGAGGG | GTCGAGAGCC | AGAAGGTACA | GGACCCCACC | 320 |
| AGGAGGAGGA | GTTCCACGTC | TCTCTCGCCC | CTTCCACCAA | 360 |
| GCCTGAACCT | TAGGCTGAGC | CACGCAGGAC | ACAAGAGGCA | 400 |
| GAAGAGGGTA | GTAGAAAATG | CGGGGCTCCG | GGCCCGCGG | 440 |
| TGCGGGACAC | CGACGGACCC | AGGGCAGAGG | TGGCGGCGAC | 480 |
| GACACCCCCC | GCGTCCCTGC | CTCTCTGGCA | GGCTGCTATT | 520 |
| CGGCACCTCT | AAAGGGCCCC | CTCTGGACGT | GCCTTCTCTT | 560 |
| GTGTGCGGCG | CTCCGGACCC | TTTTGGCCAG | CCCCAGCAAC | 600 |
| GAAGTGAATT | TGTTGGATTC | GCGCACTGTC | ATGGGGGACC | 640 |
| TTGGATGGAT | TGCTTTTCCA | AAGAACGGGT | GGGAAGAGAT | 680 |
| TGGTGAAGTT | GATGAGAACT | ATGCCCCCAT | CCACACATAC | 720 |
| CAAGTGTGCA | AAGTTATGGA | ACAGAATCAG | AATAATTGGC | 760 |
| TGTTGACCAG | TTGGATCTCT | AACGAAGGTG | CTTCCAGAAT | 800 |
| CTTTATTGAA | CTCAAGTTTA | CTTTAAGGGA | CTGCAACAGC | 840 |
| CTTCCTGGAG | GACTGGGGAC | TTGTAAGGAG | ACATTTAACA | 880 |
| TGTATTATTT | TGAATCAGAT | GATGAGAATG | GGAGAAGTAT | 920 |
| CAAAGAGAAC | CAATACATCA | AGATTGATAC | CATCGCTGCA | 960 |
| GATGAGAGCT | TCACAGAACT | TGATCTTGGT | GACCGTGTCA | 1000 |
| TGAAACTGAA | TACAGAGGTC | AGAGATGTCG | GACCTCTGAG | 1040 |
| CAAAAAGGGA | TTTTATCTTG | CTTTCCAAGA | TGTCGGTGCT | 1080 |
| TGCATTGCTC | TGGTTTCTGT | CCGTGTCTAC | TATAAAAGT | 1120 |
| GTCCCTCTGT | AGTAAGACAC | TTGGCTATCT | TCCCTGACAC | 1160 |
| TATCACTGGA | GCAGATTCAT | CACAGTTGTT | AGAGGTGTCA | 1200 |
| GGCTCCTGCG | TCAACCATTC | TGTGACAGAT | GATCCTCCCA | 1240 |
| AGATGCATTG | CAGTGCTGAA | GGGGAGTGGC | TGGTTCCCAT | 1280 |
| TGGGAAATGC | ATGTGCAAGG | CTGGATATGA | AGAGAAAAT | 1320 |
| GGTACCTGCC | AAGCTCCTTC | TCCAGTCACC | AATGTGAAAA | 1360 |
| AGGGGAAGAT | TGCAAAGAAC | AGCATTTCTT | TGTCTTGGCA | 1400 |
| AGAGCCAGAT | CGCCCCAATG | GAATTATCCT | GGAGTATGAA | 1440 |
| ATCAAGTACT | TTGAAAAGGA | CCAAGAGACC | AGTTACACAA | 1480 |
| TTATCAAGTC | TAAAGAGACC | AGTATTACAG | CCGAGGGCCT | 1520 |
| GAAACCTGCA | TCTGTGTATG | TCTTCCAAAT | TCGAGCACGT | 1560 |
| ACAGCAGCAG | GCTACGGCGT | CTTCAGTCGA | AGATTTGAGT | 1600 |

```
TTGAAACCAC  ACCAGTGTCA  GTTGCAGCAT  CTAATGATCA              1640

AAGCCAGATT  CCCATCATTG  CAGTGTCAGT  GACAGTGGGA              1680

GTCATCTTGT  TGGCAGTGAT  GATCGGCTTC  CTCCTCAGTG              1720

GCAGTTGCTG  CGATTGTGGC  TGTGGGAGGG  CTTCTTCCCT              1760

GTGCGCTGTT  GCCCATCCAA  GCCTAATATG  GCGGTGTGGC              1800

TACAGCAAAG  CAAAGCAGGA  TCCAGAAGAG  GAAAGATGC               1840

ACTTTCATAA  CGGGCACATT  AAACTGCCAG  GAGTCAGAAC              1880

CTATATTGAT  CCGCACACTT  ATGAAGATCC  CAATCAAGCT              1920

GTTCATGAAT  TTGCGAAGGA  GATTGAAGCT  TCATGCATCA              1960

CCATTGAGAG  AGTGATCGGA  GCAGGTGAAT  TTGGTGAAGT              2000

TTGCAGTGGA  TGTTTGAAAC  TACCTGGAAA  AAGAGAATTA              2040

CCTGTGGCTA  TCAAAACTCT  TAAAGTAGGC  TATACTGAAA              2080

AGCAGCGCAG  AGATTTCCTG  GGTGAAGCAA  GTATTATGGG              2120

GCAGTTCGAT  CATCCAAACA  TCATCCATCT  AGAAGGTGTT              2160

GTGACTAAAA  GCAAACCTGT  GATGATAGTG  ACAGAGTACA              2200

TGGAGAACGG  CTCCTTAGAC  ACGTTTTTAA  AGAAAAACGA              2240

TGGGCAGTTC  ACTGTGATTC  AGCTTGTTGG  CATGCTGAGA              2280

GGCATCGCTG  CAGGAATGAA  GTACCTTTCT  GACATGGGCT              2320

ACGTGCATAG  AGACCTTGCT  GCTAGAAACA  TCTTAATCAA              2360

CAGTAACCTT  GTGTGCAAGG  TGTCTGACTT  TGGACTTTCC              2400

AGGGTACTGG  AAGATGATCC  TGAGGCAGCC  TACACCACAA              2440

GGGGAGGCAA  AATTCCAATC  AGATGGACTG  CCCCGGAGGC              2480

AATAGCTTTT  CGAAAGTTCA  CCTCTGCCAG  TGATGTCTGG              2520

AGCTATGGCA  TTGTAATGTG  GGAAGTTGTA  TCTTATGGAG              2560

AGAGACCCTA  CTGGGAGATG  ACCAATCAGG  ATGTGATCAA              2600

GGCAGTGGAA  GAAGGCTACC  GCCTGCCAAG  CCCCATGGAT              2640

TGCCCTGCTG  CTCTCTATCA  ATTAATGCTG  GATTGCTGGC              2680

AGAAAGATCG  AAACAGCAGG  CCCAAGTTTG  ATGAAATCGT              2720

CAACATGCTG  GACAAACTGA  TACGAAACCC  AAGTAGTCTG              2760

AAGACACTGG  TGAATGCGTC  GAGCAGAGTG  TCTACATTGT              2800

TGGCAGAACA  TGGTTCTTTG  GGGTCTGGGG  CCTACAGATC              2840

AGTAGGTGAA  TGGCTGGAAG  CAATCAAAAT  GGGTCGGTAC              2880

ACAGAGATTT  TCATGGAAAA  TGGATACAGT  TCAATGGACG              2920

CTGTGGCTCA  GGTGACCTTG  GAGGATTTGA  GGCGCCTGGG              2960

AGTGACTCTG  GTCGGTCACC  AGAAGAAGAA  GATCATGAGC              3000

AGCCTTCAAG  AGATGAAGGT  GCAGATGGTA  AACGGGATGG              3040

TGCCAGTGTG  ACCCGCGCAT  GGGTCACACT  TCTCCAAGTG              3080

AACAACTCAG  CACTTTGTAA  ACAACCCTGA  GATTTATTTT              3120

AACAGAGAAA  GGGGAAAGGG  TGGTTTCTAA  ACCTTTGGAG              3160

GCATTTGCCT  TAACCTTTGA  GTTTATAATC  AATATTTTAC              3200
```

-continued

| | | | | |
|---|---|---|---|---|
| TAAAATCTCC | TGATCTTCCT | CTTAATTCCA | CAATGTACAG | 3240 |
| GTAACCTGCA | AAGAGAGCTA | ACATGACGAT | CAAACATCCT | 3280 |
| TTATTAAAAT | ATGTAACGAA | ATCTTCCCCA | CTTCTTCCAT | 3320 |
| GGAGTCTTGT | ACAGGAAATG | TATCAAGCTA | GAGCACCTTT | 3360 |
| AGAGACTGTT | AAGGCAGCCC | CTTTCAAAAC | TTCCAGGGAT | 3400 |
| CAACTTGAAA | GGAAAAGTTT | TAAAGCCATG | TGTGGGCTAA | 3440 |
| GAAAAGCTGC | ATTTACTGA | CGTTTACTTC | AAGTCTTAAT | 3480 |
| TGTCTACATG | AGTGTATTGA | AGAGCAATAT | GATTAGATTA | 3520 |
| TTTCTTAAAT | AGACTTTGTA | ATTTAAAATG | AAATTGCATG | 3560 |
| TTGTTAAGTT | ATAGAAGATA | GTTTATAAAC | ATGTTGCTTG | 3600 |
| GTCAAGGAAA | AGTTCAATAC | AGGGTGTATA | TTTATTTTTC | 3640 |
| TGTGTTAGAA | AATTTACTTT | TAGTTGCTCT | TCTAGAGAGT | 3680 |
| ATTAGGTAAT | GAATGTGTAT | ATATGTATAG | TTTGCAATAT | 3720 |
| ATGCAGGAAC | TGACTTACAT | CGAAATTGTG | TGTGTGTGTG | 3760 |
| TGTGCGTCGG | TGCGAGAGTA | TGTGTAGTAT | TTGAATATGT | 3800 |
| GGAGGGTATT | TTTTGCTTGC | CTTTTGGATA | GTGTTTTAAT | 3840 |
| TTTGACGACA | TACAGGAAAG | TGTCTTCTAG | ACTCTATCAT | 3880 |
| GGGTAAAAGA | GTAGAAAGCC | GTAGACCAAA | TTCCCATCCA | 3920 |
| AGTTGGTATC | TTATGCTCTC | ATTTTAAAG | CAACTAATTA | 3960 |
| GTTCATTTAA | ACAGCTAATG | CCTCTAGACT | AAATTCCCTT | 4000 |
| TGGATTTTAC | AAACACTCCC | TACCTGCCTG | TGACAGAGAA | 4040 |
| GTTCTTACCA | TTAATCTTTC | ATGCTTCTTT | GAAATTCCAC | 4080 |
| CTAAGTTCCT | GAAAATATCT | TCTAAAGCAA | ATTTGACACA | 4120 |
| AAGGGCACAC | TTGTGAAGAA | GAAGAGAGAT | GTGACTGCGC | 4160 |
| TGGCTTCTGT | TACCATCCAA | TTCAGGCAGA | GGGTACTCTA | 4200 |
| TATCTCCCTT | CATGTTTATC | CATTTGTGAC | CACTTCCACT | 4240 |
| GTGACTCATT | CACAGAGGCA | TGTTTTATAC | TAAGACAGCA | 4280 |
| TTAAAAAGTG | AAGAAAAATT | ATGAAAAAAA | AAAAAAAAA | 4320 |
| AA | | | | 4322 |

( 2 ) INFORMATION FOR SEQ ID NO: 2:

( i ) SEQUENCE CHARACTERISTICS:
        ( A ) LENGTH: 877
        ( B ) TYPE: AMINO ACID
        ( C ) STRANDEDNESS: UNKNOWN
        ( D ) TOPOLOGY: UNKNOWN ( x i ) SEQUENCE DESCRIPTION: SEQ ID NO:2:

| Met | Arg | Gly | Ser | Gly | Pro | Arg | Gly | Ala | Gly | His | Arg |
|---|---|---|---|---|---|---|---|---|---|---|---|
| 1 | | | | 5 | | | | | 10 | | |

| Arg | Thr | Gln | Gly | Arg | Gly | Gly | Gly | Asp | Asp | Thr | Pro |
|---|---|---|---|---|---|---|---|---|---|---|---|
| | | 15 | | | | | 20 | | | | |

| Arg | Val | Pro | Ala | Ser | Leu | Ala | Gly | Cys | Tyr | Ser | Ala |
|---|---|---|---|---|---|---|---|---|---|---|---|
| 25 | | | | | 30 | | | | | 35 | |

| Pro | Leu | Lys | Gly | Pro | Leu | Trp | Thr | Cys | Leu | Leu | Leu |
|---|---|---|---|---|---|---|---|---|---|---|---|

|     |     |     |     | 40  |     |     | 45  |     |     |
| --- | --- | --- | --- | --- | --- | --- | --- | --- | --- |
| Cys | Ala | Ala | Leu | Arg | Thr | Leu | Ala | Ser | Pro | Ser |
|     | 50  |     |     |     | 55  |     |     |     | 60  |
| Asn | Glu | Val | Asn | Leu | Leu | Asp | Ser | Arg | Thr | Val | Met |
|     |     |     |     | 65  |     |     |     | 70  |
| Gly | Asp | Leu | Gly | Trp | Ile | Ala | Phe | Pro | Lys | Asn | Gly |
|     |     | 75  |     |     |     | 80  |
| Trp | Glu | Glu | Ile | Gly | Glu | Val | Asp | Glu | Asn | Tyr | Ala |
| 85  |     |     |     | 90  |     |     |     |     | 95  |
| Pro | Ile | His | Thr | Tyr | Gln | Val | Cys | Lys | Val | Met | Glu |
|     |     |     | 100 |     |     |     | 105 |
| Gln | Asn | Gln | Asn | Asn | Trp | Leu | Leu | Thr | Ser | Trp | Ile |
|     | 110 |     |     |     | 115 |     |     |     | 120 |
| Ser | Asn | Glu | Gly | Ala | Ser | Arg | Ile | Phe | Ile | Glu | Leu |
|     |     |     |     | 125 |     |     |     | 130 |
| Lys | Phe | Thr | Leu | Arg | Asp | Cys | Asn | Ser | Leu | Pro | Gly |
|     |     | 135 |     |     |     | 140 |
| Gly | Leu | Gly | Thr | Cys | Lys | Glu | Thr | Phe | Asn | Met | Tyr |
| 145 |     |     |     | 150 |     |     |     | 155 |
| Tyr | Phe | Glu | Ser | Asp | Asp | Glu | Asn | Gly | Arg | Ser | Ile |
|     |     |     | 160 |     |     |     | 165 |
| Lys | Glu | Asn | Gln | Tyr | Ile | Lys | Ile | Asp | Thr | Ile | Ala |
|     | 170 |     |     |     | 175 |     |     |     | 180 |
| Ala | Asp | Glu | Ser | Phe | Thr | Glu | Leu | Asp | Leu | Gly | Asp |
|     |     |     |     | 185 |     |     |     | 190 |
| Arg | Val | Met | Lys | Leu | Asn | Thr | Glu | Val | Arg | Asp | Val |
|     |     | 195 |     |     |     | 200 |
| Gly | Pro | Leu | Ser | Lys | Lys | Gly | Phe | Tyr | Leu | Ala | Phe |
| 205 |     |     |     | 210 |     |     |     | 215 |
| Gln | Asp | Val | Gly | Ala | Cys | Ile | Ala | Leu | Val | Ser | Val |
|     |     |     | 220 |     |     |     | 225 |
| Arg | Val | Tyr | Tyr | Lys | Lys | Cys | Pro | Ser | Val | Val | Arg |
|     | 230 |     |     |     | 235 |     |     |     | 240 |
| His | Leu | Ala | Ile | Phe | Pro | Asp | Thr | Ile | Thr | Gly | Ala |
|     |     |     |     | 245 |     |     |     | 250 |
| Asp | Ser | Ser | Gln | Leu | Leu | Glu | Val | Ser | Gly | Ser | Cys |
|     |     | 255 |     |     |     | 260 |
| Val | Asn | His | Ser | Val | Thr | Asp | Asp | Pro | Pro | Lys | Met |
| 265 |     |     |     | 270 |     |     |     | 275 |
| His | Cys | Ser | Ala | Glu | Gly | Glu | Trp | Leu | Val | Pro | Ile |
|     |     |     | 280 |     |     |     | 285 |
| Gly | Lys | Cys | Met | Cys | Lys | Ala | Gly | Tyr | Glu | Glu | Lys |
|     | 290 |     |     |     | 295 |     |     |     | 300 |
| Asn | Gly | Thr | Cys | Gln | Ala | Pro | Ser | Pro | Val | Thr | Asn |
|     |     |     |     | 305 |     |     |     | 310 |
| Val | Lys | Lys | Gly | Lys | Ile | Ala | Lys | Asn | Ser | Ile | Ser |
|     |     | 315 |     |     |     | 320 |
| Leu | Ser | Trp | Gln | Glu | Pro | Asp | Arg | Pro | Asn | Gly | Ile |
| 325 |     |     |     | 330 |     |     |     | 335 |
| Ile | Leu | Glu | Tyr | Glu | Ile | Lys | Tyr | Phe | Glu | Lys | Asp |
|     |     |     | 340 |     |     |     | 345 |
| Gln | Glu | Thr | Ser | Tyr | Thr | Ile | Ile | Lys | Ser | Lys | Glu |
| 350 |     |     |     | 355 |     |     |     | 360 |

```
Thr  Ser  Ile  Thr  Ala  Glu  Gly  Leu  Lys  Pro  Ala  Ser
               365                      370

Val  Tyr  Val  Phe  Gln  Ile  Arg  Ala  Arg  Thr  Ala  Ala
          375                 380

Gly  Tyr  Gly  Val  Phe  Ser  Arg  Arg  Phe  Glu  Phe  Glu
385                      390                      395

Thr  Thr  Pro  Val  Ser  Val  Ala  Ala  Ser  Asn  Asp  Gln
               400                 405

Ser  Gln  Ile  Pro  Ile  Ile  Ala  Val  Ser  Val  Thr  Val
     410                      415                      420

Gly  Val  Ile  Leu  Leu  Ala  Val  Met  Ile  Gly  Phe  Leu
                    425                      430

Leu  Ser  Gly  Ser  Cys  Cys  Asp  Cys  Gly  Cys  Gly  Arg
          435                      440

Ala  Ser  Ser  Leu  Cys  Ala  Val  Ala  His  Pro  Ser  Leu
445                      450                      455

Ile  Trp  Arg  Cys  Gly  Tyr  Ser  Lys  Ala  Lys  Gln  Asp
               460                      465

Pro  Glu  Glu  Glu  Lys  Met  His  Phe  His  Asn  Gly  His
     470                      475                      480

Ile  Lys  Leu  Pro  Gly  Val  Arg  Thr  Tyr  Ile  Asp  Pro
                    485                      490

His  Thr  Tyr  Glu  Asp  Pro  Asn  Gln  Ala  Val  His  Glu
          495                      500

Phe  Ala  Lys  Glu  Ile  Glu  Ala  Ser  Cys  Ile  Thr  Ile
505                      510                      515

Glu  Arg  Val  Ile  Gly  Ala  Gly  Glu  Phe  Gly  Glu  Val
               520                      525

Cys  Ser  Gly  Cys  Leu  Lys  Leu  Pro  Gly  Lys  Arg  Glu
     530                      535                      540

Leu  Pro  Val  Ala  Ile  Lys  Thr  Leu  Lys  Val  Gly  Tyr
               545                      550

Thr  Glu  Lys  Gln  Arg  Arg  Asp  Phe  Leu  Gly  Glu  Ala
          555                      560

Ser  Ile  Met  Gly  Gln  Phe  Asp  His  Pro  Asn  Ile  Ile
565                      570                      575

His  Leu  Glu  Gly  Val  Val  Thr  Lys  Ser  Lys  Pro  Val
               580                      585

Met  Ile  Val  Thr  Glu  Tyr  Met  Glu  Asn  Gly  Ser  Leu
     590                      595                      600

Asp  Thr  Phe  Leu  Lys  Lys  Asn  Asp  Gly  Gln  Phe  Thr
                    605                      610

Val  Ile  Gln  Leu  Val  Gly  Met  Leu  Arg  Gly  Ile  Ala
          615                      620

Ala  Gly  Met  Lys  Tyr  Leu  Ser  Asp  Met  Gly  Tyr  Val
625                      630                      635

His  Arg  Asp  Leu  Ala  Ala  Arg  Asn  Ile  Leu  Ile  Asn
               640                      645

Ser  Asn  Leu  Val  Cys  Lys  Val  Ser  Asp  Phe  Gly  Leu
     650                      655                      660

Ser  Arg  Val  Leu  Glu  Asp  Asp  Pro  Glu  Ala  Ala  Tyr
                    665                      670

Thr  Thr  Arg  Gly  Gly  Lys  Ile  Pro  Ile  Arg  Trp  Thr
          675                      680
```

```
Ala  Pro  Glu  Ala  Ile  Ala  Phe  Arg  Lys  Phe  Thr  Ser
685                690                     695

Ala  Ser  Asp  Val  Trp  Ser  Tyr  Gly  Ile  Val  Met  Trp
               700                 705

Glu  Val  Val  Ser  Tyr  Gly  Glu  Arg  Pro  Tyr  Trp  Glu
     710                 715                          720

Met  Thr  Asn  Gln  Asp  Val  Ile  Lys  Ala  Val  Glu  Glu
                    725                      730

Gly  Tyr  Arg  Leu  Pro  Ser  Pro  Met  Asp  Cys  Pro  Ala
               735                 740

Ala  Leu  Tyr  Gln  Leu  Met  Leu  Asp  Cys  Trp  Gln  Lys
745                      750                      755

Asp  Arg  Asn  Ser  Arg  Pro  Lys  Phe  Asp  Glu  Ile  Val
               760                      765

Asn  Met  Leu  Asp  Lys  Leu  Ile  Arg  Asn  Pro  Ser  Ser
     770                      775                      780

Leu  Lys  Thr  Leu  Val  Asn  Ala  Ser  Ser  Arg  Val  Ser
                    785                      790

Thr  Leu  Leu  Ala  Glu  His  Gly  Ser  Leu  Gly  Ser  Gly
          795                      800

Ala  Tyr  Arg  Ser  Val  Gly  Glu  Trp  Leu  Glu  Ala  Ile
805                      810                      815

Lys  Met  Gly  Arg  Tyr  Thr  Glu  Ile  Phe  Met  Glu  Asn
               820                      825

Gly  Tyr  Ser  Ser  Met  Asp  Ala  Val  Ala  Gln  Val  Thr
     830                      835                      840

Leu  Glu  Asp  Leu  Arg  Arg  Leu  Gly  Val  Thr  Leu  Val
                    845                      850

Gly  His  Gln  Lys  Lys  Lys  Ile  Met  Ser  Ser  Leu  Gln
          855                      860

Glu  Met  Lys  Val  Gln  Met  Val  Asn  Gly  Met  Val  Pro
865                      870                      875

Val
```

(2) INFORMATION FOR SEQ ID NO: 3:

(i) SEQUENCE CHARACTERISTICS:
        (A) LENGTH: 986
        (B) TYPE: AMINO ACID
        (C) STRANDEDNESS: UNKNOWN
        (D) TOPOLOGY: UNKNOWN (xi) SEQUENCE DESCRIPTION: SEQ ID NO:3:

```
Met  Ala  Gly  Ile  Phe  Tyr  Phe  Ile  Leu  Phe  Ser  Phe
 1                  5                        10

Leu  Phe  Gly  Ile  Cys  Asp  Ala  Val  Thr  Gly  Ser  Arg
          15                 20

Val  Tyr  Pro  Ala  Asn  Glu  Val  Thr  Leu  Leu  Asp  Ser
25                       30                            35

Arg  Ser  Val  Gln  Gly  Glu  Leu  Gly  Trp  Ile  Ala  Ser
               40                      45

Pro  Leu  Glu  Gly  Gly  Trp  Glu  Glu  Val  Ser  Ile  Met
     50                      55                         60

Asp  Glu  Lys  Asn  Thr  Pro  Ile  Arg  Thr  Tyr  Gln  Val
                    65                      70
```

```
Cys Asn Val Met Glu Ala Ser Gln Asn Asn Trp Leu
         75                  80

Arg Thr Asp Trp Ile Thr Arg Glu Gly Ala Gln Arg
 85                  90                  95

Val Tyr Ile Glu Ile Lys Phe Thr Leu Arg Asp Cys
            100                 105

Asn Ser Leu Pro Gly Val Met Gly Thr Cys Lys Glu
        110             115                 120

Thr Phe Asn Leu Tyr Tyr Tyr Glu Ser Asp Asn Asp
                125                 130

Lys Glu Arg Phe Ile Arg Glu Ser Gln Phe Gly Lys
        135             140

Thr Asp Thr Ile Ala Ala Asp Glu Ser Phe Thr Gln
145                 150                 155

Val Asp Ile Gly Asp Arg Ile Met Lys Leu Asn Thr
            160             165

Glu Ile Arg Asp Val Gly Pro Leu Ser Lys Lys Gly
    170             175                 180

Phe Tyr Leu Ala Phe Gln Asp Val Gly Ala Cys Ile
                185             190

Ala Leu Val Ser Val Arg Val Phe Tyr Lys Lys Cys
        195             200

Pro Leu Thr Val Arg Asn Leu Ala Gln Phe Pro Asp
205             210                 215

Thr Ile Thr Gly Ala Asp Thr Ser Ser Leu Val Glu
            220             225

Val Arg Gly Ser Cys Val Asn Asn Ser Glu Glu Lys
    230             235                 240

Asp Val Pro Lys Met Tyr Cys Gly Ala Asp Gly Glu
                245             250

Trp Leu Val Pro Ile Gly Asn Cys Leu Cys Asn Ala
        255             260

Gly Tyr Glu Glu Arg Gly Phe Ala Cys Gln Ala Cys
265             270                 275

Lys Ile Gly Tyr Tyr Lys Ala Leu Ser Thr Asp Ala
            280             285

Ser Cys Ala Lys Cys Pro Pro His Ser Tyr Ser Val
    290             295                 300

Trp Glu Gly Ala Thr Ser Cys Thr Cys Asp Arg Gly
                305             310

Phe Phe Arg Ala Asp Asn Asp Ala Ala Ser Met Pro
        315             320

Cys Thr Arg Pro Pro Ser Ala Pro Leu Asn Leu Ile
325             330                 335

Ser Asn Val Asn Glu Thr Ser Val Asn Leu Glu Trp
            340             345

Ser Ser Pro Gln Asn Thr Gly Gly Arg Gln Asp Ile
    350             355                 360

Ser Tyr Asn Val Val Cys Lys Lys Cys Gly Ala Gly
                365             370

Asp Pro Ser Lys Cys Arg Pro Cys Gly Ser Gly Val
        375             380

His Tyr Thr Pro Gln Gln Asn Gly Leu Lys Thr Thr
385             390                 395
```

```
Arg  Val  Ser  Ile  Thr  Asp  Leu  Leu  Ala  His  Thr  Asn
               400                 405

Tyr  Thr  Phe  Glu  Ile  Trp  Ala  Val  Asn  Gly  Val  Ser
     410                 415                           420

Lys  Tyr  Asn  Pro  Ser  Pro  Asp  Gln  Ser  Val  Ser  Val
                    425                 430

Thr  Val  Thr  Thr  Asn  Gln  Ala  Ala  Pro  Ser  Ser  Ile
          435                      440

Ala  Leu  Val  Gln  Ala  Lys  Glu  Val  Thr  Arg  Tyr  Ser
445                      450                      455

Val  Ala  Leu  Ala  Trp  Leu  Glu  Pro  Asp  Arg  Pro  Asn
               460                 465

Gly  Val  Ile  Leu  Glu  Tyr  Glu  Val  Lys  Tyr  Tyr  Glu
     470                 475                           480

Lys  Asp  Gln  Asn  Glu  Arg  Ser  Tyr  Arg  Ile  Val  Arg
                    485                 490

Thr  Ala  Ala  Arg  Asn  Thr  Asp  Ile  Lys  Gly  Leu  Asn
          495                      500

Pro  Leu  Thr  Ser  Tyr  Val  Phe  His  Val  Arg  Ala  Arg
505                      510                      515

Thr  Ala  Ala  Gly  Tyr  Gly  Asp  Phe  Ser  Glu  Pro  Leu
               520                 525

Glu  Val  Thr  Thr  Asn  Thr  Val  Pro  Ser  Arg  Ile  Ile
     530                 535                           540

Gly  Asp  Gly  Ala  Asn  Ser  Thr  Val  Leu  Leu  Val  Ser
                    545                 550

Val  Ser  Gly  Ser  Val  Val  Leu  Val  Val  Ile  Leu  Ile
          555                      560

Ala  Ala  Phe  Val  Ile  Ser  Arg  Arg  Arg  Ser  Lys  Tyr
565                      570                      575

Ser  Lys  Ala  Lys  Gln  Glu  Ala  Asp  Glu  Glu  Lys  His
               580                 585

Ile  Asn  Gln  Gly  Val  Arg  Thr  Tyr  Val  Asp  Pro  Phe
     590                 595                           600

Thr  Tyr  Glu  Asp  Pro  Asn  Gln  Ala  Val  His  Glu  Phe
                    605                 610

Ala  Lys  Glu  Ile  Asp  Ala  Ser  Cys  Ile  Lys  Ile  Glu
          615                      620

Lys  Val  Ile  Gly  Val  Gly  Glu  Phe  Gly  Glu  Val  Cys
625                      630                      635

Ser  Gly  Cys  Leu  Lys  Val  Pro  Gly  Lys  Arg  Glu  Ile
               640                 645

Cys  Val  Ala  Ile  Lys  Thr  Leu  Lys  Ala  Gly  Tyr  Thr
     650                 655                           660

Asp  Lys  Gln  Arg  Arg  Asp  Phe  Leu  Ser  Glu  Ala  Ser
                    665                 670

Ile  Met  Gly  Gln  Phe  Asp  His  Pro  Asn  Ile  Ile  His
          675                      680

Leu  Glu  Gly  Val  Val  Thr  Lys  Cys  Lys  Pro  Val  Met
685                      690                      695

Ile  Ile  Thr  Glu  Tyr  Met  Glu  Asn  Gly  Ser  Leu  Asp
               700                 705

Ala  Phe  Leu  Arg  Lys  Asn  Asp  Gly  Arg  Phe  Thr  Val
```

```
             710                     715                    720
Ile  Gln  Leu  Val  Gly  Met  Leu  Arg  Gly  Ile  Ala  Ser
                    725                 730
Gly  Met  Lys  Tyr  Leu  Ser  Asp  Met  Ser  Tyr  Val  His
          735                 740
Arg  Asp  Leu  Ala  Ala  Arg  Asn  Ile  Leu  Val  Asn  Ser
745                 750                      755
Asn  Leu  Val  Cys  Lys  Val  Ser  Asp  Phe  Gly  Met  Ser
               760                 765
Arg  Val  Leu  Glu  Asp  Asp  Pro  Glu  Ala  Ala  Tyr  Thr
770                      775                           780
Thr  Arg  Gly  Gly  Lys  Ile  Pro  Ile  Arg  Trp  Thr  Ala
                    785                      790
Pro  Glu  Ala  Ile  Ala  Tyr  Arg  Lys  Phe  Thr  Ser  Ala
          795                      800
Ser  Asp  Val  Trp  Ser  Tyr  Gly  Ile  Val  Met  Trp  Glu
805                      810                           815
Val  Met  Ser  Tyr  Gly  Glu  Arg  Pro  Tyr  Trp  Asp  Met
               820                      825
Ser  Asn  Gln  Asp  Val  Ile  Lys  Ala  Ile  Glu  Glu  Gly
          830                 835                           840
Tyr  Arg  Leu  Pro  Pro  Pro  Met  Asp  Cys  Pro  Ile  Ala
                    845                      850
Leu  His  Gln  Leu  Met  Leu  Asp  Cys  Trp  Gln  Lys  Glu
               855                      860
Arg  Ser  Asp  Arg  Pro  Lys  Phe  Gly  Gln  Ile  Val  Asn
865                      870                      875
Met  Leu  Asp  Lys  Leu  Ile  Arg  Asn  Pro  Asn  Ser  Leu
               880                           885
Lys  Arg  Thr  Gly  Ser  Glu  Ser  Ser  Arg  Pro  Asn  Thr
          890                 895                           900
Ala  Leu  Leu  Asp  Pro  Ser  Ser  Pro  Glu  Phe  Ser  Ala
                    905                      910
Val  Val  Ser  Val  Gly  Asp  Trp  Leu  Gln  Ala  Ile  Lys
               915                 920
Met  Asp  Arg  Tyr  Lys  Asp  Asn  Phe  Thr  Ala  Ala  Gly
925                      930                           935
Tyr  Thr  Thr  Leu  Glu  Ala  Val  Val  His  Met  Ser  Gln
               940                      945
Asp  Asp  Leu  Ala  Arg  Ile  Gly  Ile  Thr  Ala  Ile  Thr
          950                 955                           960
His  Gln  Asn  Lys  Ile  Leu  Ser  Ser  Val  Gln  Ala  Met
                    965                      970
Arg  Thr  Gln  Met  Gln  Gln  Met  His  Gly  Arg  Met  Val
               975                      980
Pro  Val
985
```

( 2 ) INFORMATION FOR SEQ ID NO: 4:

( i ) SEQUENCE CHARACTERISTICS:
        ( A ) LENGTH: 982
        ( B ) TYPE: AMINO ACID
        ( C ) STRANDEDNESS: UNKNOWN
        ( D ) TOPOLOGY: UNKNOWN ( x i ) SEQUENCE DESCRIPTION: SEQ ID NO:4:

| Met | Asp | Arg | Arg | Arg | Leu | Pro | Leu | Leu | Leu | Cys |
|---|---|---|---|---|---|---|---|---|---|---|
| 1 | | | | 5 | | | | | 10 | |

| Ala | Ala | Leu | Gly | Ser | Ala | Gly | Arg | Leu | Ser | Ala | Arg |
|---|---|---|---|---|---|---|---|---|---|---|---|
| | | 15 | | | | | 20 | | | | |

| Pro | Gly | Asn | Glu | Val | Asn | Leu | Leu | Asp | Ser | Lys | Thr |
|---|---|---|---|---|---|---|---|---|---|---|---|
| 25 | | | | 30 | | | | | 35 | | |

| Ile | Gln | Gly | Glu | Leu | Gly | Trp | Ile | Ser | Tyr | Pro | Ser |
|---|---|---|---|---|---|---|---|---|---|---|---|
| | | | 40 | | | | 45 | | | | |

| His | Gly | Trp | Glu | Glu | Ile | Ser | Gly | Val | Asp | Glu | Asn |
|---|---|---|---|---|---|---|---|---|---|---|---|
| | 50 | | | | 55 | | | | | | 60 |

| Tyr | Thr | Pro | Ile | Arg | Thr | Tyr | Gln | Glu | Ser | Asn | Val |
|---|---|---|---|---|---|---|---|---|---|---|---|
| | | | | 65 | | | | 70 | | | |

| Met | Asp | His | Ser | Gln | Asn | Asn | Trp | Leu | Arg | Thr | Asn |
|---|---|---|---|---|---|---|---|---|---|---|---|
| | | 75 | | | | | 80 | | | | |

| Trp | Ile | Pro | Arg | Asn | Ser | Ala | Gln | Lys | Ile | Tyr | Val |
|---|---|---|---|---|---|---|---|---|---|---|---|
| 85 | | | | | 90 | | | | | 95 | |

| Glu | Leu | Lys | Phe | Thr | Leu | Arg | Asp | Cys | Asn | Ser | Ile |
|---|---|---|---|---|---|---|---|---|---|---|---|
| | | | 100 | | | | | 105 | | | |

| Pro | Leu | Val | Leu | Gly | Thr | Cys | Lys | Glu | Thr | Phe | Asn |
|---|---|---|---|---|---|---|---|---|---|---|---|
| 110 | | | | | 115 | | | | | | 120 |

| Leu | Tyr | Tyr | Met | Glu | Ser | Asp | Asp | His | Leu | Ala |
|---|---|---|---|---|---|---|---|---|---|---|
| | | | | 125 | | | | | 130 | |

| Lys | Phe | Arg | Glu | His | Gln | Phe | Thr | Lys | Ile | Asp | Thr |
|---|---|---|---|---|---|---|---|---|---|---|---|
| | | 135 | | | | | 140 | | | | |

| Ile | Ala | Ala | Asp | Glu | Ser | Phe | Thr | Gln | Met | Asp | Leu |
|---|---|---|---|---|---|---|---|---|---|---|---|
| 145 | | | | | 150 | | | | | 155 | |

| Gly | Asp | Arg | Ile | Leu | Lys | Leu | Asn | Thr | Glu | Val | Arg |
|---|---|---|---|---|---|---|---|---|---|---|---|
| | | | 160 | | | | | 165 | | | |

| Glu | Val | Gly | Pro | Val | Ser | Lys | Lys | Gly | Phe | Tyr | Leu |
|---|---|---|---|---|---|---|---|---|---|---|---|
| | 170 | | | | | 175 | | | | | 180 |

| Ala | Phe | Gln | Asp | Val | Gly | Ala | Cys | Val | Ala | Leu | Val |
|---|---|---|---|---|---|---|---|---|---|---|---|
| | | | | 185 | | | | | 190 | | |

| Ser | Val | Arg | Val | Tyr | Phe | Lys | Lys | Cys | Pro | Phe | Thr |
|---|---|---|---|---|---|---|---|---|---|---|---|
| | | 195 | | | | | 200 | | | | |

| Val | Lys | Asn | Leu | Ala | Met | Phe | Pro | Asp | Thr | Val | Pro |
|---|---|---|---|---|---|---|---|---|---|---|---|
| 205 | | | | | 210 | | | | | 215 | |

| Met | Asp | Ser | Gln | Ser | Leu | Val | Glu | Val | Arg | Gly | Ser |
|---|---|---|---|---|---|---|---|---|---|---|---|
| | | | 220 | | | | | 225 | | | |

| Cys | Val | Asn | His | Ser | Lys | Glu | Glu | Glu | Pro | Pro | Lys |
|---|---|---|---|---|---|---|---|---|---|---|---|
| | 230 | | | | | 235 | | | | | 240 |

| Met | Tyr | Cys | Ser | Thr | Glu | Gly | Glu | Trp | Leu | Val | Pro |
|---|---|---|---|---|---|---|---|---|---|---|---|
| | | | | 245 | | | | | 250 | | |

| Ile | Gly | Lys | Cys | Leu | Cys | Asn | Ala | Gly | Tyr | Glu | Glu |
|---|---|---|---|---|---|---|---|---|---|---|---|
| | | 255 | | | | | 260 | | | | |

| Arg | Gly | Phe | Ala | Cys | Gln | Ala | Cys | Arg | Pro | Gly | Phe |
|---|---|---|---|---|---|---|---|---|---|---|---|
| 265 | | | | | 270 | | | | | 275 | |

| Tyr | Lys | Ala | Ser | Ala | Gly | Asn | Val | Lys | Cys | Ala | Lys |
|---|---|---|---|---|---|---|---|---|---|---|---|
| | | | 280 | | | | 285 | | | | |

| Cys | Pro | Pro | His | Ser | Tyr | Thr | Tyr | Glu | Asp | Ala | Ser |
|---|---|---|---|---|---|---|---|---|---|---|---|
| | 290 | | | | | 295 | | | | | 300 |

| Leu | Asn | Cys | Arg | Cys | Glu | Lys | Asn | Tyr | Phe | Arg | Ser |
|---|---|---|---|---|---|---|---|---|---|---|---|
| | | | | 305 | | | | | 310 | | |

```
Glu  Lys  Asp  Pro  Pro  Ser  Met  Ala  Cys  Thr  Arg  Pro
          315            320
Pro  Ser  Ala  Pro  Arg  Asn  Val  Ile  Ser  Asn  Ile  Asn
325            330                      335
Glu  Thr  Ser  Val  Ile  Leu  Asp  Trp  Ser  Trp  Pro  Leu
               340                 345
Asp  Thr  Gly  Gly  Arg  Lys  Asp  Val  Thr  Phe  Asn  Ile
     350                 355                           360
Ile  Cys  Lys  Lys  Cys  Gly  Gly  Ser  Ser  Lys  Ile  Cys
                365                      370
Glu  Pro  Cys  Ser  Asp  Asn  Val  Arg  Phe  Leu  Pro  Arg
          375                      380
Gln  Thr  Gly  Leu  Thr  Asn  Thr  Thr  Val  Thr  Val  Val
385                      390                      395
Asp  Leu  Leu  Ala  His  Thr  Asn  Tyr  Thr  Phe  Glu  Ile
                    400                 405
Asp  Ala  Val  Asn  Gly  Val  Ser  Asp  Leu  Ser  Thr  Leu
     410                      415                      420
Ser  Arg  Gln  Phe  Ala  Val  Ser  Ile  Thr  Thr  Asn
                    425                 430
Gln  Ala  Ala  Pro  Ser  Pro  Ile  Thr  Val  Ile  Arg  Lys
          435                      440
Asp  Arg  Thr  Ser  Arg  Asn  Ser  Val  Ser  Leu  Ser  Trp
445                      450                      455
Gln  Glu  Pro  Glu  His  Pro  Asn  Gly  Ile  Ile  Leu  Asp
               460                      465
Tyr  Glu  Val  Lys  Tyr  Glu  Lys  Gln  Glu  Gln  Glu  Thr
     470                 475                           480
Ser  Tyr  Thr  Ile  Leu  Arg  Ala  Lys  Ser  Thr  Asn  Val
                    485                 490
Thr  Ile  Ser  Gly  Leu  Lys  Pro  Asp  Thr  Thr  Tyr  Val
          495                 500
Phe  Gln  Ile  Arg  Ala  Arg  Thr  Ala  Ala  Arg  Tyr  Gly
505                      510                      515
Thr  Ser  Ser  Arg  Lys  Phe  Glu  Phe  Glu  Thr  Ser  Pro
               520                 525
Asp  Ser  Phe  Ser  Ile  Ser  Ser  Glu  Asn  Ser  Gln  Val
     530                      535                      540
Val  Met  Ile  Ala  Ile  Ser  Ala  Ala  Val  Ala  Ile  Ile
                    545                 550
Leu  Leu  Thr  Val  Val  Val  Tyr  Val  Leu  Ile  Gly  Arg
          555                      560
Phe  Cys  Gly  Tyr  Lys  Lys  Ser  Lys  His  Gly  Thr  Asp
565                      570                      575
Glu  Lys  Arg  Leu  His  Phe  Gly  Asn  Gly  His  Ile  Lys
               580                 585
Leu  Pro  Gly  Leu  Arg  Thr  Tyr  Val  Asp  Pro  His  Thr
     590                 595                           600
Tyr  Glu  Asp  Pro  Asn  Gln  Ala  Val  His  Glu  Phe  Ala
                    605                 610
Lys  Glu  Ile  Asp  Ala  Ser  Asn  Ile  Ser  Ile  Asp  Lys
          615                      620
Val  Val  Gly  Ala  Gly  Glu  Phe  Gly  Glu  Val  Cys  Ser
625                      630                      635
```

| | | | | | | | | | |
|---|---|---|---|---|---|---|---|---|---|
| Gly | Arg | Leu | Lys<br>640 | Leu | Pro | Ser | Lys | Lys<br>645 | Glu | Ile | Ser |
| Val | Ala<br>650 | Ile | Lys | Thr | Leu<br>655 | Lys | Val | Gly | Tyr | Thr | Glu<br>660 |
| Lys | Gln | Arg | Arg<br>665 | Asp | Phe | Leu | Gly | Glu<br>670 | Ala | Ser | Ile |
| Met | Gly | Gln<br>675 | Phe | Asp | His | Pro | Asn<br>680 | Ile | Ile | Arg | Leu |
| Glu<br>685 | Gly | Val | Val | Thr | Lys<br>690 | Ser | Lys | Pro | Val<br>695 | Met | Ile |
| Val | Thr | Glu | Tyr<br>700 | Met | Glu | Asn | Gly | Ser<br>705 | Leu | Asp | Ser |
| Phe | Leu<br>710 | Arg | Lys | His | Asp | Ala<br>715 | Gln | Phe | Thr | Val | Ile<br>720 |
| Gln | Leu | Val | Gly | Met<br>725 | Leu | Arg | Gly | Ile | Ala<br>730 | Ser | Gly |
| Met | Lys | Tyr<br>735 | Leu | Ser | Asp | Met | Gly<br>740 | Tyr | Val | His | Arg |
| Asp<br>745 | Leu | Ala | Ala | Arg | Asn<br>750 | Ile | Leu | Ile | Asn<br>755 | Ser | Asn |
| Leu | Val<br>760 | Cys | Lys | Val | Ser | Asp | Phe<br>765 | Gly | Leu | Ser | Arg |
| Val | Leu<br>770 | Glu | Asp | Asp | Pro | Glu<br>775 | Ala | Ala | Tyr | Thr | Thr<br>780 |
| Arg | Gly | Gly | Lys | Ile<br>785 | Pro | Ile | Arg | Trp | Thr<br>790 | Ser | Pro |
| Glu | Ala | Ile<br>795 | Ala | Tyr | Arg | Lys | Phe<br>800 | Thr | Ser | Ala | Ser |
| Asp<br>805 | Ala | Trp | Ser | Tyr | Gly<br>810 | Ile | Val | Leu | Trp<br>815 | Glu | Val |
| Met | Ser | Tyr | Gly<br>820 | Glu | Arg | Pro | Tyr | Trp<br>825 | Glu | Met | Ser |
| Phe | Gln<br>830 | Asp | Val | Ile | Lys | Ala<br>835 | Val | Asp | Glu | Gly | Tyr<br>840 |
| Arg | Leu | Pro | Pro | Pro<br>845 | Met | Asp | Cys | Pro | Ala<br>850 | Ala | Leu |
| Tyr | Gln | Leu<br>855 | Met | Leu | Asp | Cys | Trp<br>860 | Gln | Lys | Asp | Arg |
| Asn<br>865 | Asn | Arg | Pro | Lys | Phe<br>870 | Glu | Gln | Ile | Val<br>875 | Ser | Ile |
| Leu | Asp | Lys | Leu<br>880 | Ile | Arg | Asn | Pro | Ser<br>885 | Ser | Leu | Lys |
| Ile | Ile | Thr<br>890 | Asn | Ala | Ala | Ala | Arg<br>895 | Pro | Ser | Asn | Leu<br>900 |
| Leu | Leu | Asp | Gln | Ser<br>905 | Asn | Ile | Asp | Ile<br>910 | Ser | Ala | Phe |
| Arg | Thr | Ala<br>915 | Gly | Asp | Trp | Leu | Asn<br>920 | Gly | Phe | Arg | Thr |
| Gly<br>925 | Gln | Cys | Lys | Gly | Ile<br>930 | Phe | Thr | Gly | Val<br>935 | Glu | Tyr |
| Ser | Ser | Cys | Asp<br>940 | Thr | Ile | Ala | Lys<br>945 | Ile | Ser | Thr | Asp |
| Asp | Met | Lys | Lys | Val | Gly | Val | Thr | Val | Val | Gly | Pro |

950                    955                         960
Gln  Lys  Lys  Ile  Val  Ser  Ser  Ile  Lys  Thr  Leu  Glu
                         965                         970

Thr  His  Thr  Lys  Asn  Ser  Pro  Val  Pro  Val
          975                    980

( 2 ) INFORMATION FOR SEQ ID NO: 5:

( i ) SEQUENCE CHARACTERISTICS:
      ( A ) LENGTH: 995
      ( B ) TYPE: AMINO ACID
      ( C ) STRANDEDNESS: UNKNOWN
      ( D ) TOPOLOGY: UNKNOWN ( x i ) SEQUENCE DESCRIPTION: SEQ ID NO:5:

Met  Pro  Gly  Pro  Glu  Arg  Thr  Met  Gly  Pro  Leu  Trp
 1                   5                        10

Phe  Cys  Cys  Leu  Pro  Leu  Ala  Leu  Leu  Pro  Leu  Leu
          15                   20

Ala  Ala  Val  Glu  Glu  Thr  Leu  Met  Asp  Ser  Thr  Thr
 25                       30                            35

Ala  Thr  Ala  Glu  Leu  Gly  Trp  Met  Val  His  Pro  Pro
               40                       45

Ser  Gly  Trp  Glu  Glu  Val  Ser  Gly  Tyr  Asp  Glu  Asn
      50                       55                        60

Met  Asn  Thr  Ile  Arg  Thr  Tyr  Gln  Val  Cys  Lys  Val
                    65                        70

Phe  Glu  Ser  Ser  Gln  Asn  Asn  Trp  Leu  Arg  Thr  Lys
               75                   80

Tyr  Ile  Arg  Arg  Arg  Gly  Ala  His  Arg  Ile  His  Val
 85                       90                             95

Glu  Met  Lys  Phe  Ser  Val  Arg  Asp  Cys  Ser  Ser  Ile
                    100                 105

Pro  Asn  Val  Pro  Gly  Ser  Cys  Lys  Glu  Thr  Phe  Asn
     110                      115                       120

Leu  Tyr  Tyr  Tyr  Glu  Ser  Asp  Phe  Asp  Ser  Ala  Thr
                    125                      130

Lys  Thr  Phe  Pro  Asn  Trp  Met  Glu  Asn  Pro  Trp  Met
          135                      140

Lys  Val  Asp  Thr  Ile  Ala  Ala  Asp  Glu  Ser  Phe  Ser
145                      150                      155

Gln  Val  Asp  Leu  Gly  Gly  Arg  Val  Met  Lys  Leu  Asn
               160                      165

Thr  Glu  Val  Arg  Ser  Phe  Gly  Pro  Val  Ser  Lys  Lys
     170                      175                       180

Gly  Phe  Tyr  Leu  Ala  Phe  Gln  Asp  Tyr  Gly  Ala  Cys
                    185                      190

Met  Ser  Leu  Ile  Ala  Val  Arg  Val  Phe  Tyr  Arg  Lys
               195                      200

Cys  Pro  Arg  Val  Ile  Gln  Asn  Gly  Ala  Val  Phe  Gln
205                      210                      215

Glu  Thr  Leu  Ser  Gly  Ala  Glu  Ser  Thr  Ser  Leu  Val
               220                      225

Ala  Ala  Arg  Gly  Thr  Cys  Ile  Ser  Asn  Ala  Glu  Glu
230                      235                      240

Val  Asp  Val  Pro  Ile  Lys  Leu  Tyr  Cys  Asn  Gly  Ala

```
                                        245                                    250
Gly   Glu   Trp   Leu   Val   Pro   Ile   Gly   Arg   Cys   Met   Cys
                  255                           260

Arg   Pro   Gly   Tyr   Glu   Ser   Val   Glu   Asn   Gly   Thr   Val
265                           270                           275

Cys   Arg   Gly   Cys   Pro   Ser   Gly   Thr   Phe   Lys   Ala   Ser
                        280                     285

Gln   Gly   Asp   Glu   Gly   Cys   Val   His   Cys   Pro   Ile   Asn
            290                     295                           300

Ser   Arg   Thr   Thr   Ser   Glu   Gly   Ala   Thr   Asn   Cys   Val
                        305                     310

Cys   Arg   Asn   Gly   Tyr   Tyr   Arg   Ala   Asp   Ala   Asp   Pro
                  315                     320

Val   Asp   Met   Pro   Cys   Thr   Thr   Ile   Pro   Asp   Ala   Pro
325                           330                           335

Gln   Ala   Val   Ile   Ser   Ser   Val   Asn   Glu   Thr   Ser   Leu
                  340                           345

Met   Leu   Glu   Trp   Thr   Pro   Pro   Arg   Asp   Ser   Gly   Gly
      350                                 355                     360

Arg   Glu   Asp   Leu   Val   Tyr   Asn   Ile   Ile   Cys   Lys   Ser
                        365                           370

Cys   Gly   Ser   Gly   Arg   Gly   Ala   Cys   Thr   Arg   Cys   Gly
                  375                           380

Asp   Asn   Val   Gln   Phe   Ala   Pro   Arg   Gln   Leu   Gly   Leu
385                           390                           395

Thr   Glu   Pro   Arg   Ile   Tyr   Ile   Ser   Asp   Leu   Leu   Ala
                        400                     405

His   Thr   Gln   Tyr   Thr   Phe   Glu   Ile   Gln   Ala   Val   Asn
            410                     415                           420

Gly   Val   Thr   Asp   Gln   Ser   Pro   Phe   Ser   Pro   Gln   Phe
                        425                     430

Ala   Ser   Val   Asn   Ile   Thr   Thr   Asn   Gln   Ala   Ala   Pro
            435                           440

Ser   Ala   Val   Ser   Ile   Met   His   Gln   Val   Ser   Arg   Thr
445                           450                           455

Val   Asp   Ser   Ile   Thr   Leu   Ser   Trp   Ser   Gln   Pro   Asp
                  460                           465

Gln   Pro   Asn   Gly   Val   Ile   Leu   Asp   Tyr   Glu   Leu   Gln
      470                           475                           480

Tyr   Tyr   Glu   Lys   Asn   Leu   Ser   Glu   Leu   Asn   Ser   Thr
                        485                     490

Ala   Val   Lys   Ser   Pro   Thr   Asn   Thr   Val   Thr   Val   Gln
                  495                     500

Asn   Leu   Lys   Ala   Gly   Thr   Ile   Tyr   Val   Phe   Gln   Val
505                                 510                     515

Arg   Ala   Arg   Thr   Val   Ala   Gly   Tyr   Gly   Arg   Tyr   Ser
                  520                           525

Gly   Lys   Met   Tyr   Phe   Gln   Thr   Met   Thr   Glu   Ala   Glu
      530                           535                           540

Tyr   Gln   Thr   Ser   Val   Gln   Glu   Lys   Leu   Pro   Leu   Ile
                        545                           550

Ile   Gly   Ser   Ser   Ala   Ala   Gly   Leu   Val   Phe   Leu   Ile
            555                           560
```

```
Ala  Val  Val  Val  Ile  Ile  Ile  Val  Cys  Asn  Arg  Arg
565            570                      575

Arg  Gly  Phe  Glu  Arg  Ala  Asp  Ser  Glu  Tyr  Thr  Asp
               580                 585

Lys  Leu  Gln  His  Tyr  Thr  Ser  Gly  His  Met  Thr  Pro
590                      595                           600

Gly  Met  Lys  Ile  Tyr  Ile  Asp  Pro  Phe  Thr  Tyr  Glu
                    605                      610

Asp  Pro  Asn  Glu  Ala  Val  Arg  Glu  Phe  Ala  Lys  Glu
               615                 620

Ile  Asp  Ile  Ser  Cys  Val  Lys  Ile  Glu  Gln  Val  Ile
625                      630                      635

Gly  Ala  Gly  Glu  Phe  Gly  Glu  Val  Cys  Ser  Gly  His
               640                      645

Leu  Lys  Leu  Pro  Gly  Lys  Arg  Glu  Ile  Phe  Val  Ala
650                      655                           660

Ile  Lys  Thr  Leu  Lys  Ser  Gly  Tyr  Thr  Glu  Lys  Gln
                    665                 670

Arg  Arg  Asp  Phe  Leu  Ser  Glu  Ala  Ser  Ile  Met  Gly
               675                 680

Gln  Phe  Asp  His  Pro  Asn  Val  Ile  His  Leu  Glu  Gly
685                      690                      695

Val  Val  Thr  Lys  Ser  Ser  Pro  Val  Met  Ile  Val  Thr
               700                      705

Glu  Tyr  Met  Glu  Asn  Gly  Ser  Leu  Asp  Ser  Phe  Leu
     710                      715                      720

Arg  Gln  Asn  Asp  Gly  Gln  Phe  Thr  Val  Ile  Gln  Leu
                    725                      730

Val  Gly  Met  Leu  Arg  Gly  Ile  Ala  Ala  Gly  Met  Lys
          735                      740

Tyr  Leu  Ala  Asp  Met  Asn  Tyr  Val  His  Arg  Asp  Leu
745                 750                      755

Ala  Ala  Arg  Asn  Ile  Leu  Val  Asn  Ser  Asn  Leu  Val
               760                      765

Cys  Lys  Val  Ser  Asp  Phe  Gly  Leu  Ser  Arg  Phe  Leu
     770                      775                      780

Glu  Asp  Asp  Thr  Ser  Asp  Pro  Thr  Tyr  Thr  Ser  Ala
                    785                      790

Leu  Gly  Gly  Lys  Ile  Pro  Ile  Arg  Trp  Thr  Ala  Pro
          795                      800

Glu  Ala  Ile  Gln  Tyr  Arg  Lys  Phe  Thr  Ser  Ala  Ser
805                      810                      815

Asp  Val  Trp  Ser  Tyr  Gly  Ile  Val  Met  Trp  Glu  Val
               820                      825

Met  Ser  Tyr  Gly  Glu  Arg  Pro  Tyr  Trp  Asp  Met  Thr
     830                      835                      840

Asn  Gln  Asp  Val  Ile  Asn  Ala  Ile  Glu  Gln  Asp  Tyr
                    845                      850

Arg  Leu  Pro  Pro  Pro  Met  Asp  Cys  Pro  Asn  Ala  Leu
          855                      860

His  Gln  Leu  Met  Leu  Asp  Cys  Trp  Gln  Lys  Asp  Arg
865                      870                      875

Asn  His  Arg  Pro  Lys  Phe  Gly  Gln  Ile  Val  Asn  Thr
               880                      885
```

| Leu | Asp | Lys | Met | Ile | Arg | Asn | Pro | Asn | Ser | Leu | Lys |
|---|---|---|---|---|---|---|---|---|---|---|---|
| | 890 | | | | 895 | | | | | | 900 |

| Ala | Met | Ala | Pro | Leu | Ser | Ser | Gly | Val | Asn | Leu | Pro |
|---|---|---|---|---|---|---|---|---|---|---|---|
| | | | | 905 | | | | | 910 | | |

| Leu | Leu | Asp | Arg | Thr | Ile | Pro | Asp | Tyr | Thr | Ser | Phe |
|---|---|---|---|---|---|---|---|---|---|---|---|
| | | | 915 | | | | 920 | | | | |

| Asn | Thr | Val | Asp | Glu | Trp | Leu | Asp | Ala | Ile | Lys | Met |
|---|---|---|---|---|---|---|---|---|---|---|---|
| 925 | | | | | 930 | | | | | 935 | |

| Ser | Gln | Tyr | Lys | Glu | Ser | Phe | Ala | Ser | Ala | Gly | Phe |
|---|---|---|---|---|---|---|---|---|---|---|---|
| | | | 940 | | | | | 945 | | | |

| Thr | Thr | Phe | Asp | Ile | Val | Ser | Gln | Met | Thr | Val | Glu |
|---|---|---|---|---|---|---|---|---|---|---|---|
| | 950 | | | | | 955 | | | | | 960 |

| Asp | Ile | Leu | Arg | Val | Gly | Val | Thr | Leu | Ala | Gly | His |
|---|---|---|---|---|---|---|---|---|---|---|---|
| | | | | 965 | | | | | 970 | | |

| Gln | Lys | Lys | Ile | Leu | Asn | Ser | Ile | Gln | Val | Met | Arg |
|---|---|---|---|---|---|---|---|---|---|---|---|
| | | 975 | | | | | 980 | | | | |

| Ala | Gln | Met | Asn | Gln | Ile | Gln | Ser | Val | Glu | Val |
|---|---|---|---|---|---|---|---|---|---|---|
| 985 | | | | | 990 | | | | | |

( 2 ) INFORMATION FOR SEQ ID NO: 6:

( i ) SEQUENCE CHARACTERISTICS:
        ( A ) LENGTH: 984
        ( B ) TYPE: AMINO ACID
        ( C ) STRANDEDNESS: UNKNOWN
        ( D ) TOPOLOGY: UNKNOWN ( x i ) SEQUENCE DESCRIPTION: SEQ ID NO:6:

| Met | Ala | Leu | Asp | Cys | Leu | Leu | Leu | Phe | Leu | Leu | Ala |
|---|---|---|---|---|---|---|---|---|---|---|---|
| 1 | | | | 5 | | | | | 10 | | |

| Ser | Ala | Val | Ala | Ala | Met | Glu | Glu | Thr | Leu | Met | Asp |
|---|---|---|---|---|---|---|---|---|---|---|---|
| | | 15 | | | | | 20 | | | | |

| Ser | Arg | Thr | Ala | Thr | Ala | Glu | Leu | Gly | Trp | Thr | Ala |
|---|---|---|---|---|---|---|---|---|---|---|---|
| 25 | | | | | 30 | | | | | 35 | |

| Asn | Pro | Ala | Ser | Gly | Trp | Glu | Glu | Val | Ser | Gly | Tyr |
|---|---|---|---|---|---|---|---|---|---|---|---|
| | | | 40 | | | | | 45 | | | |

| Asp | Glu | Asn | Leu | Asn | Thr | Ile | Arg | Thr | Tyr | Gln | Val |
|---|---|---|---|---|---|---|---|---|---|---|---|
| | 50 | | | | | 55 | | | | | 60 |

| Cys | Asn | Val | Phe | Glu | Pro | Asn | Gln | Asn | Asn | Trp | Leu |
|---|---|---|---|---|---|---|---|---|---|---|---|
| | | | | 65 | | | | | 70 | | |

| Leu | Thr | Thr | Phe | Ile | Asn | Arg | Arg | Gly | Ala | His | Arg |
|---|---|---|---|---|---|---|---|---|---|---|---|
| | | 75 | | | | | 80 | | | | |

| Ile | Tyr | Thr | Glu | Met | Arg | Phe | Thr | Val | Arg | Asp | Cys |
|---|---|---|---|---|---|---|---|---|---|---|---|
| 85 | | | | | 90 | | | | | 95 | |

| Ser | Ser | Leu | Pro | Asn | Val | Pro | Gly | Ser | Cys | Lys | Glu |
|---|---|---|---|---|---|---|---|---|---|---|---|
| | | | 100 | | | | | 105 | | | |

| Thr | Phe | Asn | Leu | Tyr | Tyr | Tyr | Glu | Thr | Asp | Ser | Val |
|---|---|---|---|---|---|---|---|---|---|---|---|
| | 110 | | | | | 115 | | | | | 120 |

| Ile | Ala | Thr | Lys | Lys | Ser | Ala | Phe | Trp | Ser | Glu | Ala |
|---|---|---|---|---|---|---|---|---|---|---|---|
| | | | | 125 | | | | | 130 | | |

| Pro | Tyr | Leu | Lys | Val | Asp | Thr | Ile | Ala | Ala | Asp | Glu |
|---|---|---|---|---|---|---|---|---|---|---|---|
| | | 135 | | | | | 140 | | | | |

| Ser | Phe | Ser | Gln | Val | Asp | Phe | Gly | Gly | Arg | Leu | Met |
|---|---|---|---|---|---|---|---|---|---|---|---|
| 145 | | | | | 150 | | | | | 155 | |

| Lys | Val | Asn | Thr | Glu | Val | Arg | Ser | Phe | Gly | Pro | Leu |
|---|---|---|---|---|---|---|---|---|---|---|---|
| | | | 160 | | | | | 165 | | | |

```
Thr Arg Asn Gly Phe Tyr Leu Ala Phe Gln Asp Tyr
    170             175             180

Gly Ala Cys Met Ser Leu Leu Ser Val Arg Val Phe
                185             190

Phe Lys Lys Cys Pro Ser Ile Val Gln Asn Phe Ala
        195             200

Val Phe Pro Glu Thr Met Thr Gly Ala Glu Ser Thr
205             210             215

Ser Leu Val Ile Ala Arg Gly Thr Cys Ile Pro Asn
            220             225

Ala Glu Glu Val Asp Val Pro Ile Lys Leu Tyr Cys
    230             235             240

Asn Gly Asp Gly Glu Trp Met Val Pro Ile Gly Arg
                245             250

Cys Thr Cys Lys Ala Gly Tyr Glu Pro Glu Asn Ser
        255             260

Val Ala Cys Lys Ala Cys Pro Ala Gly Thr Phe Lys
265             270             275

Ala Ser Gln Glu Ala Glu Gly Cys Ser His Cys Pro
            280             285

Ser Asn Ser Arg Ser Pro Ser Glu Ala Ser Pro Ile
    290             295             300

Cys Thr Cys Arg Thr Gly Tyr Tyr Arg Ala Asp Phe
                305             310

Asp Pro Pro Glu Val Ala Cys Thr Ser Val Pro Ser
        315             320

Gly Pro Arg Asn Val Ile Ser Ile Val Asn Glu Thr
325             330             335

Ser Ile Ile Leu Glu Trp His Pro Pro Arg Glu Thr
            340             345

Gly Gly Arg Asp Asp Val Thr Tyr Asn Ile Ile Cys
    350             355             360

Lys Lys Cys Arg Ala Asp Asp Arg Ser Cys Ser Arg
                365             370

Cys Asp Asp Asn Val Glu Phe Val Pro Arg Gln Leu
        375             380

Gly Leu Thr Glu Cys Arg Val Ser Ile Ser Ser Leu
385             390             395

Trp Ala His Thr Pro Tyr Thr Phe Asp Ile Gln Ala
            400             405

Ile Asn Gly Val Ser Ser Lys Ser Pro Phe Pro Pro
    410             415             420

Gln His Val Ser Val Asn Ile Thr Thr Asn Gln Ala
                425             430

Ala Pro Ser Thr Val Pro Ile Met His Gln Val Ser
        435             440

Ala Thr Met Arg Ser Ile Thr Leu Ser Trp Pro Gln
445             450             455

Pro Glu Gln Pro Asn Gly Ile Ile Leu Asp Tyr Glu
            460             465

Ile Arg Tyr Tyr Glu Lys Glu His Asn Glu Phe Asn
470             475             480

Ser Ser Met Ala Arg Ser Gln Thr Asn Thr Ala Arg
```

-continued

```
                                     485                     490
Ile  Asp  Gly  Leu  Arg  Pro  Gly  Met  Val  Tyr  Val  Val
          495                      500

Gln  Val  Arg  Ala  Arg  Thr  Val  Ala  Gly  Tyr  Gly  Lys
505                      510                     515

Phe  Ser  Gly  Lys  Met  Cys  Phe  Gln  Thr  Leu  Thr  Asp
               520                 525

Asp  Asp  Tyr  Lys  Ser  Glu  Leu  Arg  Glu  Gln  Leu  Pro
     530                      535                     540

Leu  Ile  Ala  Gly  Ser  Ala  Ala  Gly  Val  Val  Phe
                    545                     550

Val  Val  Ser  Leu  Val  Ala  Ile  Ser  Ile  Val  Cys  Ser
               555                 560

Arg  Lys  Arg  Ala  Tyr  Ser  Lys  Glu  Ala  Val  Tyr  Ser
565                           565                     570

Asp  Lys  Leu  Gln  His  Tyr  Ser  Thr  Gly  Arg  Gly  Ser
                    575                580

Pro  Gly  Met  Lys  Ile  Tyr  Ile  Asp  Pro  Phe  Thr  Tyr
     585                      595                     600

Glu  Asp  Pro  Asn  Glu  Ala  Val  Arg  Glu  Phe  Ala  Lys
                         605                610

Glu  Ile  Asp  Val  Ser  Phe  Val  Lys  Ile  Glu  Glu  Val
          615                      620

Ile  Gly  Ala  Gly  Glu  Phe  Gly  Glu  Val  Tyr  Lys  Gly
625                           630                     635

Arg  Leu  Lys  Leu  Pro  Gly  Lys  Arg  Glu  Ile  Tyr  Val
                    640                645

Ala  Ile  Lys  Thr  Leu  Lys  Ala  Gly  Tyr  Ser  Glu  Lys
     650                      655                     660

Gln  Arg  Arg  Asp  Phe  Leu  Ser  Glu  Ala  Ser  Ile  Met
                    665                 670

Gly  Gln  Phe  Asp  His  Pro  Asn  Ile  Ile  Arg  Leu  Glu
          675                      680

Gly  Val  Val  Thr  Lys  Ser  Arg  Pro  Val  Met  Ile  Ile
685                      690                     695

Thr  Glu  Phe  Met  Glu  Asn  Gly  Ala  Leu  Asp  Ser  Phe
               700                      705

Leu  Arg  Gln  Asn  Asp  Gly  Gln  Phe  Thr  Val  Ile  Gln
     710                      715                     720

Leu  Val  Gly  Met  Leu  Arg  Gly  Ile  Ala  Ala  Gly  Met
                    725                     730

Lys  Tyr  Leu  Ser  Glu  Met  Asn  Tyr  Val  His  Arg  Asp
               735                      740

Leu  Ala  Ala  Arg  Asn  Ile  Leu  Val  Asn  Ser  Asn  Leu
745                      750                     755

Val  Cys  Lys  Val  Ser  Asp  Phe  Gly  Leu  Ser  Arg  Tyr
               760                      765

Leu  Gln  Asp  Asp  Thr  Ser  Asp  Pro  Thr  Tyr  Thr  Ser
     770                      775                     780

Ser  Leu  Gly  Gly  Lys  Ile  Pro  Val  Arg  Trp  Thr  Ala
                    785                     790

Pro  Glu  Ala  Ile  Ala  Tyr  Arg  Lys  Phe  Thr  Ser  Ala
     795                      800
```

| Ser | Asp | Val | Trp | Ser | Tyr | Gly | Ile | Val | Met | Trp | Glu |
| 805 | | | | 810 | | | | | 815 | | |

| Val | Met | Ser | Phe | Gly | Glu | Arg | Pro | Tyr | Trp | Asp | Met |
| | | | 820 | | | | 825 | | | | |

| Ser | Asn | Gln | Asp | Val | Ile | Asn | Ala | Val | Glu | Gln | Asp |
| | 830 | | | | 835 | | | | | | 840 |

| Tyr | Arg | Leu | Pro | Pro | Met | Asp | Cys | Pro | Ala | Ala |
| | | | 845 | | | | | 850 | | |

| Leu | His | Gln | Leu | Met | Leu | Asp | Cys | Trp | Gln | Lys | Asp |
| | | 855 | | | | | 860 | | | | |

| Arg | Asn | Ser | Arg | Pro | Arg | Phe | Ala | Glu | Ile | Val | Asn |
| 865 | | | | | 870 | | | | | | 875 |

| Thr | Leu | Asp | Lys | Met | Ile | Arg | Asn | Pro | Ala | Ser | Leu |
| | | | 880 | | | | | 885 | | | |

| Lys | Thr | Val | Ala | Thr | Ile | Thr | Ala | Val | Pro | Ser | Gln |
| | 890 | | | | 895 | | | | | | 900 |

| Pro | Leu | Leu | Asp | Arg | Ser | Ile | Pro | Asp | Phe | Thr | Ala |
| | | | | 905 | | | | | 910 | | |

| Phe | Thr | Thr | Val | Asp | Asp | Trp | Leu | Ser | Ala | Ile | Lys |
| | | 915 | | | | | 920 | | | | |

| Met | Val | Gln | Tyr | Arg | Asp | Ser | Phe | Leu | Thr | Ala | Gly |
| 925 | | | | | 930 | | | | | 935 | |

| Phe | Thr | Ser | Leu | Gln | Leu | Val | Thr | Gln | Met | Thr | Ser |
| | | | 940 | | | | 945 | | | | |

| Glu | Asp | Leu | Leu | Arg | Ile | Gly | Val | Thr | Leu | Ala | Gly |
| 950 | | | | | 955 | | | | | | 960 |

| His | Gln | Lys | Lys | Ile | Leu | Ser | Ser | Ile | His | Ser | Met |
| | | | | 965 | | | | | 970 | | |

| Arg | Val | Gln | Met | Asn | Gln | Ser | Pro | Ser | Val | Met | Ala |
| | | 975 | | | | | 980 | | | | |

( 2 ) INFORMATION FOR SEQ ID NO: 7:

( i ) SEQUENCE CHARACTERISTICS:
      ( A ) LENGTH: 970
      ( B ) TYPE: AMINO ACID
      ( C ) STRANDEDNESS: UNKNOWN
      ( D ) TOPOLOGY: UNKNOWN ( x i ) SEQUENCE DESCRIPTION: SEQ ID NO:7:

| Gly | Val | Ser | Ser | Arg | Ala | Arg | Arg | Pro | Pro | Gly | Ser |
| 1 | | | | 5 | | | | | 10 | | |

| Ser | Arg | Ser | Ser | Arg | Arg | Gly | Val | Thr | Ser | Glu | Leu |
| | | 15 | | | | | 20 | | | | |

| Ala | Trp | Thr | Thr | His | Pro | Glu | Thr | Gly | Trp | Glu | Glu |
| 25 | | | | | 30 | | | | | 35 | |

| Val | Ser | Gly | Tyr | Asp | Glu | Ala | Met | Gln | Pro | Ile | Arg |
| | | | 40 | | | | | 45 | | | |

| Thr | Tyr | Gln | Val | Cys | Gln | Val | Arg | Glu | Ala | Gln | Gln |
| | | 50 | | | | 55 | | | | | 60 |

| Gln | Gln | Trp | Leu | Arg | Thr | Lys | Phe | Ile | Asn | Arg | Gln |
| | | | | 65 | | | | | 70 | | |

| Asp | Val | Gln | Arg | Val | Tyr | Val | Glu | Leu | Lys | Phe | Thr |
| | | | 75 | | | | 80 | | | | |

| Val | Arg | Asp | Cys | Lys | Ser | Ile | Pro | Lys | Ile | Pro | Gly |
| 85 | | | | | 90 | | | | | 95 | |

```
Ser  Cys  Lys  Glu  Thr  Phe  Asn  Leu  Phe  Tyr  Tyr  Glu
               100                      105

Ser  Asp  Thr  Asp  Ser  Ala  Ser  Ala  Asn  Ser  Pro  Phe
          110                 115                      120

Trp  Met  Glu  Asn  Pro  Tyr  Ile  Lys  Val  Asp  Thr  Ile
                    125                      130

Ala  Pro  Asp  Glu  Ser  Phe  Ser  Lys  Leu  Glu  Ser  Gly
               135                 140

Arg  Val  Asn  Thr  Lys  Val  Arg  Ser  Phe  Gly  Pro  Leu
145                      150                      155

Ser  Lys  Asn  Gly  Phe  Tyr  Leu  Ala  Phe  Gln  Asp  Leu
               160                 165

Gly  Ala  Cys  Met  Ser  Leu  Ile  Leu  Val  Arg  Ala  Phe
          170                 175                      180

Tyr  Lys  Lys  Cys  Ser  Asn  Thr  Ile  Ala  Gly  Phe  Ala
                    185                      190

Ile  Phe  Pro  Glu  Thr  Leu  Thr  Gly  Ala  Glu  Pro  Thr
               195                 200

Ser  Leu  Val  Ile  Ala  Pro  Gly  Thr  Cys  Ile  Pro  Gln
205                      210                      215

Ala  Val  Glu  Val  Ser  Val  Pro  Leu  Lys  Leu  Tyr  Cys
               220                      225

Asn  Gly  Asp  Gly  Glu  Trp  Met  Val  Pro  Val  Gly  Ala
     230                      235                      240

Cys  Thr  Cys  Ala  Ala  Gly  Tyr  Glu  Pro  Ala  Met  Lys
                    245                      250

Asp  Thr  Gln  Cys  Gln  Ala  Cys  Gly  Pro  Gly  Thr  Phe
          255                      260

Lys  Ser  Lys  Gln  Gly  Glu  Gly  Pro  Cys  Ser  Pro  Cys
265                      270                      275

Pro  Pro  Asn  Ser  Arg  Thr  Thr  Ala  Gly  Ala  Ala  Thr
               280                      285

Val  Cys  Ile  Cys  Arg  Ser  Gly  Phe  Phe  Arg  Ala  Asp
     290                 295                           300

Ala  Asp  Pro  Ala  Asp  Ser  Ala  Cys  Thr  Ser  Val  Pro
               305                           310

Ser  Ala  Pro  Arg  Ser  Val  Ile  Ser  Asn  Val  Asn  Glu
               315                 320

Thr  Ser  Phe  Val  Leu  Glu  Trp  Ser  Glu  Pro  Gln  Asp
325                      330                      335

Ala  Gly  Gly  Arg  Asp  Asp  Leu  Leu  Tyr  Asn  Val  Ile
               340                      345

Cys  Lys  Lys  Cys  Ser  Val  Glu  Arg  Arg  Leu  Cys  Ser
     350                      355                      360

Arg  Cys  Asp  Asp  Asn  Val  Glu  Phe  Val  Pro  Arg  Gln
                    365                      370

Leu  Gly  Leu  Thr  Glu  Arg  Arg  Ile  Tyr  Ile  Ser  Lys
          375                      380

Val  Met  Ala  His  Pro  Gln  Tyr  Thr  Phe  Glu  Ile  Gln
385                      390                      395

Ala  Val  Asn  Gly  Ile  Ser  Ser  Lys  Ser  Pro  Tyr  Pro
               400                 405

Pro  His  Phe  Ala  Ser  Val  Asn  Ile  Thr  Thr  Asn  Gln
     410                      415                      420
```

```
Ala  Val  Leu  Ser  Ala  Val  Pro  Thr  Met  His  Leu  His
                    425                      430

Ser  Ser  Thr  Gly  Asn  Ser  Met  Thr  Leu  Ser  Trp  Thr
               435                 440

Pro  Pro  Glu  Arg  Pro  Asn  Gly  Ile  Ile  Leu  Asp  Tyr
445                      450                           455

Glu  Ile  Lys  Tyr  Ser  Glu  Lys  Gln  Gly  Gln  Gly  Asp
               460                      465

Gly  Ile  Ala  Asn  Thr  Val  Thr  Ser  Gln  Lys  Asn  Ser
          470                 475                      480

Val  Arg  Leu  Asp  Gly  Leu  Lys  Ala  Asn  Ala  Arg  Tyr
                    485                 490

Met  Val  Gln  Val  Arg  Ala  Arg  Thr  Val  Ala  Gly  Tyr
               495                 500

Gly  Arg  Tyr  Ser  Leu  Pro  Thr  Glu  Phe  Gln  Thr  Thr
505                      510                      515

Ala  Glu  Asp  Gly  Ser  Thr  Ser  Lys  Thr  Phe  Gln  Glu
               520                      525

Leu  Pro  Leu  Ile  Val  Gly  Ser  Ala  Thr  Ala  Gly  Leu
     530                      535                      540

Leu  Phe  Val  Ile  Val  Val  Ile  Ile  Ala  Ile  Val
                    545                 550

Cys  Phe  Arg  Lys  Gln  Arg  Asn  Ser  Thr  Asp  Pro  Glu
               555                 560

Tyr  Thr  Glu  Lys  Leu  Gln  Gln  Tyr  Val  Thr  Pro  Gly
565                      570                      575

Met  Lys  Val  Tyr  Ile  Asp  Pro  Phe  Thr  Tyr  Glu  Asp
               580                      585

Pro  Asn  Glu  Ala  Val  Arg  Glu  Phe  Ala  Lys  Glu  Ile
     590                      595                      600

Asp  Ile  Ser  Cys  Val  Lys  Ile  Glu  Glu  Val  Ile  Gly
                    605                      610

Ala  Gly  Glu  Phe  Gly  Glu  Val  Cys  Arg  Gly  Arg  Leu
          615                      620

Lys  Leu  Pro  Gly  Lys  Arg  Glu  Ile  Phe  Val  Ala  Ile
625                      630                      635

Lys  Thr  Leu  Lys  Val  Gly  Tyr  Thr  Glu  Arg  Gln  Arg
               640                      645

Arg  Asp  Phe  Leu  Ser  Glu  Ala  Ser  Ile  Met  Gly  Gln
     650                      655                      660

Phe  Asp  His  Pro  Asn  Ile  Ile  His  Leu  Glu  Gly  Val
                    665                      670

Val  Thr  Lys  Ser  Arg  Pro  Val  Met  Ile  Val  Thr  Glu
               675                      680

Glu  Met  Glu  Asn  Cys  Ala  Leu  Asp  Ser  Phe  Leu  Arg
685                      690                      695

Leu  Asn  Asp  Gly  Gln  Phe  Thr  Val  Ile  Gln  Leu  Val
               700                      705

Gly  Met  Leu  Arg  Gly  Ile  Ala  Ala  Gly  Met  Lys  Tyr
     710                      715                      720

Leu  Ser  Glu  Met  Asn  Tyr  Val  His  Arg  Asp  Leu  Ala
                    725                      730

Ala  Arg  Asn  Ile  Leu  Val  Asn  Ser  Asn  Leu  Val  Cys
```

735                         740

Lys   Val   Ser   Asp   Phe   Gly   Leu   Ser   Arg   Phe   Leu   Glu
745                           750                           755

Asp   Asp   Pro   Ala   Asp   Pro   Thr   Tyr   Thr   Ser   Ser   Leu
                  760                     765

Gly   Gly   Lys   Ile   Pro   Ile   Arg   Trp   Thr   Ala   Pro   Glu
      770                     775                                 780

Ala   Ile   Ala   Tyr   Arg   Lys   Phe   Thr   Ser   Ala   Ser   Asp
                        785                           790

Val   Trp   Ser   Tyr   Gly   Ile   Val   Met   Trp   Glu   Val   Met
            795                           800

Ser   Tyr   Gly   Glu   Arg   Pro   Tyr   Trp   Asp   Met   Ser   Asn
805                           810                           815

Gln   Asp   Val   Ile   Asn   Ala   Val   Glu   Gln   Asp   Tyr   Arg
                  820                           825

Leu   Pro   Pro   Pro   Met   Asp   Cys   Pro   Thr   Ala   Leu   His
            830                     835                           840

Gln   Leu   Met   Leu   Asp   Cys   Trp   Val   Arg   Asp   Arg   Asn
                        845                           850

Leu   Arg   Pro   Lys   Phe   Ala   Gln   Ile   Val   Asn   Thr   Leu
            855                           860

Asp   Lys   Leu   Ile   Arg   Asn   Ala   Ala   Ser   Leu   Lys   Val
865                           870                           875

Ile   Ala   Ser   Val   Gln   Ser   Gly   Val   Ser   Gln   Pro   Leu
                  880                           885

Ala   Asp   Arg   Thr   Val   Pro   Asp   Tyr   Thr   Thr   Phe   Thr
      890                     895                                 900

Thr   Val   Gly   Asp   Trp   Leu   Asp   Ala   Ile   Lys   Met   Gly
                        905                           910

Arg   Tyr   Lys   Glu   Asn   Phe   Val   Asn   His   Gly   Phe   Ala
                  915                     920

Ser   Phe   Asp   Leu   Val   Ala   Gln   Met   Thr   Ala   Glu   Asp
925                           930                           935

Leu   Leu   Arg   Ile   Gly   Val   Thr   Leu   Ala   Gly   His   Gln
                  940                           945

Lys   Lys   Ile   Leu   Ser   Ser   Ile   Gln   Asp   Met   Arg   Leu
      950                           955                           960

Gln   Met   Asn   Gln   Thr   Leu   Pro   Val   Gln   Val
                        965                     970

( 2 ) INFORMATION FOR SEQ ID NO: 8:

( i ) SEQUENCE CHARACTERISTICS:
        ( A ) LENGTH: 977
        ( B ) TYPE: AMINO ACID
        ( C ) STRANDEDNESS: UNKNOWN
        ( D ) TOPOLOGY: UNKNOWN ( x i ) SEQUENCE DESCRIPTION: SEQ ID NO:8:

Met   Glu   Leu   Gln   Ala   Ala   Arg   Ala   Cys   Phe   Ala   Leu
1                       5                           10

Leu   Trp   Gly   Cys   Ala   Leu   Ala   Ala   Ala   Ala   Ala   Ala
            15                          20

Gln   Gly   Lys   Glu   Val   Val   Leu   Leu   Asp   Phe   Ala   Ala
25                            30                            35

Ala   Gly   Gly   Glu   Leu   Gly   Trp   Leu   Thr   His   Pro   Tyr

```
                          40                          45

Gly  Lys  Gly  Trp  Asp  Leu  Met  Gln  Asn  Ile  Met  Asn
     50                       55                         60

Asp  Met  Pro  Ile  Tyr  Met  Tyr  Ser  Val  Cys  Asn  Val
               65                       70

Met  Ser  Gly  Asp  Gln  Asp  Asn  Trp  Leu  Arg  Ser  Asn
          75                      80

Trp  Ile  Tyr  Arg  Gly  Glu  Ala  Glu  Arg  Asn  Asn
85                       90                       95

Phe  Glu  Leu  Asn  Phe  Thr  Val  Arg  Asp  Cys  Lys  Ser
               100                      105

Phe  Pro  Gly  Gly  Ala  Ser  Ser  Cys  Lys  Glu  Thr  Phe
          110                 115                         120

Asn  Leu  Tyr  Tyr  Ala  Glu  Ser  Asp  Leu  Asp  Tyr  Gly
                    125                      130

Thr  Asn  Phe  Gln  Lys  Arg  Leu  Phe  Thr  Lys  Ile  Asp
               135                 140

Thr  Ile  Ala  Pro  Asp  Glu  Ile  Thr  Val  Ser  Ser  Asp
145                      150                      155

Phe  Glu  Ala  Arg  His  Val  Lys  Leu  Asn  Val  Glu  Glu
                    160                 165

Arg  Ser  Val  Gly  Pro  Leu  Thr  Arg  Lys  Gly  Phe  Tyr
170                           175                         180

Leu  Ala  Phe  Gln  Asp  Ile  Gly  Ala  Cys  Val  Ala  Leu
                    185                      190

Leu  Ser  Val  Arg  Val  Tyr  Tyr  Lys  Lys  Cys  Pro  Glu
          195                      200

Leu  Leu  Gln  Gly  Leu  Ala  His  Phe  Pro  Glu  Thr  Ile
205                      210                      215

Ala  Gly  Ser  Asp  Ala  Pro  Ser  Leu  Ala  Thr  Val  Ala
               220                      225

Gly  Thr  Cys  Val  Asp  His  Ala  Val  Val  Pro  Pro  Gly
          230                 235                         240

Gly  Glu  Glu  Pro  Arg  Met  His  Cys  Ala  Val  Asp  Gly
                    245                      250

Glu  Trp  Leu  Val  Pro  Ile  Gly  Gln  Cys  Leu  Cys  Gln
          255                      260

Ala  Gly  Tyr  Glu  Lys  Val  Glu  Asp  Ala  Cys  Gln  Ala
265                      270                      275

Cys  Ser  Pro  Gly  Phe  Phe  Lys  Phe  Glu  Ala  Ser  Glu
               280                      285

Ser  Pro  Cys  Leu  Glu  Cys  Pro  Glu  His  Thr  Leu  Pro
290                      295                           300

Ser  Pro  Glu  Gly  Ala  Thr  Ser  Cys  Glu  Cys  Glu  Glu
                    305                      310

Gly  Phe  Phe  Arg  Ala  Pro  Gln  Asp  Pro  Ala  Ser  Met
               315                      320

Pro  Cys  Thr  Arg  Pro  Pro  Ser  Ala  Pro  His  Tyr  Leu
325                           330                      335

Thr  Ala  Val  Gly  Met  Gly  Ala  Lys  Val  Glu  Leu  Arg
                    340                      345

Trp  Thr  Pro  Pro  Gln  Asp  Ser  Gly  Gly  Arg  Glu  Asp
          350                      355                    360
```

|  |  |  |  |  |  |  |  |  |  |
|---|---|---|---|---|---|---|---|---|---|
| Ile | Val | Tyr | Ser | Val<br>365 | Thr | Cys | Glu | Gln<br>370 | Cys | Trp | Pro |
| Glu | Ser | Gly<br>375 | Glu | Cys | Gly | Pro<br>380 | Cys | Glu | Ala | Ser | Val |
| Arg<br>385 | Tyr | Ser | Glu | Pro | Pro<br>390 | His | Gly | Leu | Thr | Arg<br>395 | Thr |
| Ser | Val | Thr | Val<br>400 | Ser | Asp | Leu | Glu | Pro<br>405 | His | Met | Asn |
| Tyr | Thr<br>410 | Phe | Thr | Val | Glu | Ala<br>415 | Arg | Asn | Gly | Val | Ser<br>420 |
| Gly | Leu | Val | Thr | Ser<br>425 | Arg | Ser | Phe | Arg | Thr<br>430 | Ala | Ser |
| Val | Ser | Ile<br>435 | Asn | Gln | Thr | Glu | Pro<br>440 | Pro | Lys | Val | Arg |
| Asn<br>445 | Glu | Gly | Arg | Ser | Thr<br>450 | Thr | Ser | Leu | Ser | Val<br>455 | Ser |
| Trp | Ser | Ile | Pro<br>460 | Pro | Pro | Gln | Gln<br>465 | Ser | Arg | Val | Trp |
| Lys | Tyr<br>470 | Glu | Val | Thr | Tyr<br>475 | Arg | Lys | Lys | Gly | Asp<br>480 | Ser |
| Asn | Ser | Tyr | Asn | Val<br>485 | Arg | Arg | Thr | Glu | Gly<br>490 | Phe | Ser |
| Val | Thr | Leu<br>495 | Asp | Asp | Leu | Ala | Pro<br>500 | Asp | Thr | Thr | Tyr |
| Leu<br>505 | Val | Gln | Val | Gln | Ala<br>510 | Leu | Thr | Gln | Glu | Gly<br>515 | Gln |
| Gly | Ala | Gly | Ser<br>520 | Lys | Val | His | Glu | Phe<br>525 | Gln | Thr | Leu |
| Ser | Pro<br>530 | Glu | Gly | Ser | Gly | Asn<br>535 | Leu | Ala | Val | Ile | Gly<br>540 |
| Gly | Val | Ala | Val | Gly<br>545 | Val | Val | Leu | Leu | Leu<br>550 | Val | Leu |
| Ala | Gly | Val<br>555 | Gly | Phe | Phe | Ile | His<br>560 | Arg | Arg | Arg | Lys |
| Asn<br>565 | Gln | Arg | Ala | Arg | Gln<br>570 | Ser | Pro | Glu | Asp | Val<br>575 | Tyr |
| Phe | Ser | Lys | Ser<br>580 | Glu | Gln | Leu | Lys | Pro<br>585 | Leu | Lys | Thr |
| Tyr | Val<br>590 | Asp | Pro | His | Thr | Tyr<br>595 | Glu | Asp | Pro | Asn | Gln<br>600 |
| Ala | Val | Leu | Lys | Phe<br>605 | Thr | Thr | Glu | Ile | His<br>610 | Pro | Ser |
| Cys | Val | Thr | Arg<br>615 | Gln | Thr | Val | Ile<br>620 | Gly | Glu | Gly | Glu |
| Phe<br>625 | Gly | Glu | Val | Tyr | Lys<br>630 | Gly | Met | Leu | Lys | Thr<br>635 | Ser |
| Ser | Gly | Lys | Lys<br>640 | Glu | Val | Pro | Val | Ala<br>645 | Ile | Lys | Thr |
| Leu | Lys<br>650 | Ala | Gly | Tyr | Thr | Glu<br>655 | Lys | Gln | Arg | Arg | Asp<br>660 |
| Phe | Leu | Gly | Glu | Ala<br>665 | Gly | Ile | Met | Gly | Gln<br>670 | Phe | Ser |
| His | His | Asn<br>675 | Ile | Ile | Arg | Leu | Glu<br>680 | Gly | Val | Ile | Ser |

```
Lys  Tyr  Lys  Pro  Met  Met  Ile  Ile  Thr  Glu  Tyr  Met
685                 690                      695

Glu  Asn  Gly  Ala  Leu  Asp  Lys  Phe  Leu  Arg  Glu  Lys
               700                 705

Asp  Gly  Gln  Phe  Ser  Val  Leu  Gln  Leu  Val  Gly  Met
          710                 715                      720

Leu  Arg  Gly  Ile  Ala  Ala  Gly  Met  Lys  Tyr  Leu  Ala
                    725                      730

Asn  Met  Asn  Tyr  Val  His  Arg  Asp  Leu  Ala  Ala  Arg
          735                      740

Asn  Ile  Leu  Val  Asn  Ser  Asn  Leu  Val  Cys  Lys  Val
745                      750                 755

Ser  Asp  Phe  Gly  Leu  Ser  Arg  Val  Leu  Glu  Asp  Asp
               760                      765

Pro  Glu  Ala  Thr  Tyr  Thr  Thr  Ser  Gly  Gly  Lys  Ile
770                           775                      780

Pro  Ile  Arg  Trp  Thr  Ala  Pro  Glu  Ala  Ile  Ser  Tyr
                    785                      790

Arg  Lys  Phe  Thr  Ser  Ala  Ser  Asp  Val  Trp  Ser  Phe
          795                      800

Gly  Ile  Val  Met  Trp  Glu  Val  Met  Thr  Tyr  Gly  Glu
805                      810                           815

Arg  Pro  Tyr  Trp  Glu  Leu  Ser  Asn  His  Glu  Val  Met
               820                      825

Lys  Ala  Ile  Asn  Asp  Gly  Phe  Arg  Leu  Pro  Thr  Pro
830                           835                      840

Met  Asp  Cys  Pro  Ser  Ala  Ile  Tyr  Gln  Leu  Met  Met
                    845                      850

Gln  Cys  Trp  Gln  Gln  Glu  Arg  Ala  Arg  Arg  Pro  Lys
               855                      860

Phe  Ala  Asp  Ile  Val  Ser  Ile  Leu  Asp  Lys  Leu  Ile
865                           870                      875

Arg  Ala  Pro  Asp  Ser  Leu  Lys  Thr  Leu  Ala  Asp  Phe
               880                           885

Asp  Pro  Arg  Val  Ser  Ile  Arg  Leu  Pro  Ser  Thr  Ser
890                           895                      900

Gly  Ser  Asp  Gly  Ile  Pro  Tyr  Arg  Thr  Val  Ser  Glu
                    905                      910

Trp  Leu  Glu  Ser  Ile  Lys  Met  Gln  Gln  Tyr  Thr  Glu
          915                      920

His  Phe  Met  Ala  Ala  Gly  Tyr  Thr  Ala  Ile  Glu  Lys
925                      930                      935

Val  Val  Gln  Met  Thr  Asn  Asp  Asp  Ile  Lys  Arg  Ile
               940                      945

Gly  Val  Arg  Leu  Pro  Gly  His  Gln  Lys  Arg  Ile  Ala
     950                      955                      960

Tyr  Ser  Leu  Leu  Gly  Leu  Lys  Asp  Gln  Val  Asn  Thr
                    965                      970

Val  Gly  Ile  Pro  Ile
               975
```

( 2 ) INFORMATION FOR SEQ ID NO: 9:

( i ) SEQUENCE CHARACTERISTICS:

(A) LENGTH: 984
(B) TYPE: AMINO ACID
(C) STRANDEDNESS: UNKNOWN
(D) TOPOLOGY: UNKNOWN (xi) SEQUENCE DESCRIPTION: SEQ ID NO:9:

```
Met Glu Arg Arg Trp Pro Leu Gly Leu Val
 1               5                  10

Leu Leu Leu Cys Ala Pro Leu Pro Gly Ala Arg
            15              20

Ala Lys Glu Val Thr Leu Met Asp Thr Ser Lys Ala
 25              30                  35

Gln Gly Glu Leu Gly Trp Leu Leu Asp Pro Pro Lys
            40              45

Asp Gly Trp Ser Glu Gln Gln Gln Ile Leu Asn Gly
    50              55                      60

Thr Pro Leu Tyr Met Tyr Gln Asp Cys Pro Met Gln
                65              70

Gly Arg Arg Asp Thr Asp His Trp Leu Arg Ser Asn
        75              80

Trp Ile Tyr Arg Gly Glu Glu Ala Ser Arg Val His
 85              90                  95

Val Glu Leu Gln Phe Thr Val Arg Asp Cys Lys Ser
            100             105

Phe Pro Gly Gly Ala Gly Pro Leu Gly Cys Lys Glu
    110             115                     120

Thr Phe Asn Leu Leu Tyr Met Glu Ser Asp Gln Asp
            125             130

Val Gly Ile Gln Leu Arg Arg Pro Leu Phe Gln Lys
        135             140

Val Thr Thr Val Ala Ala Asp Gln Ser Phe Thr Ile
145             150             155

Arg Asp Leu Ala Ser Gly Ser Val Lys Leu Asn Val
            160             165

Glu Arg Cys Ser Leu Gly Arg Leu Thr Arg Arg Gly
    170             175                     180

Leu Tyr Leu Ala Phe His Asn Pro Gly Ala Cys Val
                185             190

Ala Leu Val Ser Val Arg Val Phe Tyr Gln Arg Cys
        195             200

Pro Glu Thr Leu Asn Gly Leu Ala Gln Phe Pro Asp
205             210             215

Thr Leu Pro Gly Pro Ala Gly Leu Val Glu Val Ala
            220             225

Gly Thr Cys Leu Pro His Ala Arg Ala Ser Pro Arg
        230             235             240

Pro Ser Gly Ala Pro Arg Met His Cys Ser Pro Asp
            245             250

Gly Glu Trp Leu Val Pro Val Gly Arg Cys His Cys
            255             260

Glu Pro Gly Tyr Glu Glu Gly Gly Ser Gly Glu Ala
265             270             275

Cys Val Ala Cys Pro Ser Gly Ser Tyr Arg Met Asp
            280             285

Met Asp Thr Pro His Cys Leu Thr Cys Pro Gln Gln
```

|     |     |     |     |     |     |     |     |     |     |
|-----|-----|-----|-----|-----|-----|-----|-----|-----|-----|
|     |     |     |     | 290 |     |     | 295 |     | 300 |
| Ser | Thr | Ala | Glu | Ser | Glu | Gly | Ala | Thr | Ile | Cys | Thr |
|     |     |     |     |     | 305 |     |     | 310 |     |
| Cys | Glu | Ser | Gly | His | Tyr | Arg | Ala | Pro | Gly | Glu | Gly |
|     |     | 315 |     |     |     | 320 |     |     |     |
| Pro | Gln | Val | Ala | Cys | Thr | Gly | Pro | Pro | Ser | Ala | Pro |
| 325 |     |     |     |     | 330 |     |     |     | 335 |
| Arg | Asn | Leu | Ser | Phe | Ser | Ala | Ser | Gly | Thr | Gly | Leu |
|     |     |     | 340 |     |     |     | 345 |     |     |
| Ser | Leu | Arg | Trp | Glu | Pro | Pro | Ala | Asp | Thr | Gly | Gly |
|     | 350 |     |     |     |     | 355 |     |     |     | 360 |
| Arg | Gln | Asp | Val | Arg | Tyr | Ser | Val | Arg | Cys | Ser | Gln |
|     |     |     |     | 365 |     |     |     |     | 370 |
| Cys | Gln | Gly | Thr | Ala | Gln | Asp | Gly | Gly | Pro | Cys | Gln |
|     |     | 375 |     |     |     | 380 |     |     |     |
| Pro | Cys | Gly | Val | Gly | Val | His | Phe | Ser | Pro | Gly | Ala |
| 385 |     |     |     |     | 390 |     |     |     | 395 |
| Arg | Ala | Leu | Lys | Thr | Pro | Ala | Val | His | Val | Asn | Gly |
|     |     |     | 400 |     |     |     | 405 |     |     |
| Leu | Glu | Pro | Tyr | Ala | Asn | Tyr | Thr | Phe | Asn | Val | Glu |
|     | 410 |     |     |     |     | 415 |     |     |     | 420 |
| Ala | Gln | Asn | Gly | Val | Ser | Gly | Leu | Gly | Ser | Ser | Gly |
|     |     |     |     | 425 |     |     |     | 430 |     |
| His | Ala | Ser | Thr | Ser | Val | Ser | Ile | Ser | Met | Gly | His |
|     |     | 435 |     |     |     | 440 |     |     |     |
| Ala | Glu | Ser | Leu | Ser | Gly | Leu | Ser | Leu | Arg | Leu | Val |
| 445 |     |     |     |     | 450 |     |     |     | 455 |
| Lys | Lys | Glu | Pro | Arg | Gln | Leu | Glu | Leu | Thr | Trp | Ala |
|     |     |     | 460 |     |     |     | 465 |     |     |
| Gly | Ser | Arg | Pro | Arg | Ser | Pro | Gly | Ala | Asn | Leu | Thr |
|     | 470 |     |     |     |     | 475 |     |     |     | 480 |
| Tyr | Glu | Leu | His | Val | Leu | Asn | Gln | Asp | Glu | Glu | Arg |
|     |     |     |     | 485 |     |     |     | 490 |     |
| Tyr | Gln | Met | Val | Leu | Glu | Pro | Arg | Val | Leu | Leu | Thr |
|     |     | 495 |     |     |     | 500 |     |     |     |
| Glu | Leu | Gln | Pro | Asp | Thr | Thr | Tyr | Ile | Val | Arg | Val |
| 505 |     |     |     |     | 510 |     |     |     | 515 |
| Arg | Met | Leu | Thr | Pro | Leu | Gly | Pro | Gly | Pro | Phe | Ser |
|     |     |     | 520 |     |     |     | 525 |     |     |
| Pro | Asp | His | Glu | Phe | Arg | Thr | Ser | Pro | Pro | Val | Ser |
|     | 530 |     |     |     |     | 535 |     |     |     | 540 |
| Arg | Gly | Leu | Thr | Gly | Gly | Glu | Ile | Val | Ala | Val | Ile |
|     |     |     |     | 545 |     |     |     | 550 |     |
| Phe | Gly | Leu | Leu | Leu | Gly | Ala | Ala | Leu | Leu | Leu | Gly |
|     |     |     | 555 |     |     |     | 560 |     |     |
| Ile | Leu | Val | Phe | Arg | Ser | Arg | Arg | Ala | Gly | Arg | Gln |
| 565 |     |     |     |     | 570 |     |     |     | 575 |
| Arg | Gln | Gln | Arg | His | Val | Thr | Ala | Pro | Pro | Met | Trp |
|     |     |     | 580 |     |     |     | 585 |     |     |
| Ile | Glu | Arg | Thr | Ser | Cys | Ala | Glu | Ala | Leu | Cys | Gly |
|     |     | 590 |     |     |     | 595 |     |     |     | 600 |
| Thr | Ser | Arg | His | Thr | Arg | Thr | Leu | His | Arg | Glu | Pro |
|     |     |     |     | 605 |     |     |     | 610 |     |

```
Trp  Thr  Leu  Pro  Gly  Gly  Trp  Ser  Asn  Phe  Pro  Ser
          615            620

Arg  Glu  Leu  Asp  Pro  Ala  Trp  Leu  Met  Val  Asp  Thr
625                 630                      635

Val  Ile  Gly  Glu  Gly  Phe  Gly  Val  Tyr  Arg
               640            645

Gly  Thr  Leu  Arg  Leu  Pro  Ser  Gln  Asp  Cys  Lys  Thr
     650                 655                           660

Val  Ala  Ile  Lys  Thr  Leu  Lys  Asp  Thr  Ser  Pro  Gly
               665                      670

Gly  Gln  Trp  Trp  Asn  Phe  Leu  Arg  Glu  Ala  Thr  Ile
          675                      680

Met  Gly  Gln  Phe  Ser  His  Pro  Asn  Ile  Leu  His  Leu
685                      690                      695

Glu  Gly  Val  Val  Thr  Lys  Arg  Lys  Pro  Ile  Met  Ile
               700                 705

Ile  Thr  Glu  Phe  Met  Glu  Asn  Ala  Ala  Leu  Asp  Ala
     710                      715                      720

Phe  Leu  Arg  Glu  Arg  Glu  Asp  Gln  Leu  Val  Pro  Gly
                    725                      730

Gln  Leu  Val  Ala  Met  Leu  Gln  Gly  Ile  Ala  Ala  Gly
          735                      740

Met  Asn  Tyr  Leu  Ser  Asn  His  Asn  Tyr  Val  His  Arg
745                      750                      755

Asp  Leu  Ala  Ala  Arg  Asn  Ile  Leu  Val  Asn  Gln  Asn
               760                      765

Leu  Cys  Cys  Lys  Val  Ser  Asp  Phe  Gly  Leu  Thr  Arg
     770                      775                      780

Leu  Leu  Asp  Asp  Phe  Asp  Gly  Thr  Tyr  Glu  Thr  Gln
                    785                      790

Gly  Gly  Lys  Ile  Pro  Ile  Arg  Trp  Thr  Ala  Pro  Glu
          795                      800

Ala  Ile  Ala  His  Arg  Ile  Phe  Thr  Thr  Ala  Ser  Asp
805                      810                      815

Val  Trp  Ser  Phe  Gly  Ile  Val  Met  Trp  Glu  Val  Leu
               820                      825

Ser  Phe  Gly  Asp  Lys  Pro  Tyr  Gly  Glu  Met  Ser  Asn
     830                      835                      840

Gln  Glu  Val  Met  Lys  Ser  Ile  Glu  Asp  Gly  Tyr  Arg
                    845                      850

Leu  Pro  Pro  Pro  Val  Asp  Cys  Pro  Ala  Pro  Leu  Tyr
          855                      860

Glu  Leu  Met  Lys  Asn  Cys  Trp  Ala  Tyr  Asp  Arg  Ala
865                      870                      875

Arg  Arg  Pro  His  Phe  Gln  Lys  Leu  Gln  Ala  His  Leu
               880                      885

Glu  Gln  Leu  Leu  Ala  Asn  Pro  His  Cys  Leu  Arg  Thr
     890                      895                      900

Ile  Ala  Asn  Phe  Asp  Pro  Arg  Val  Thr  Leu  Arg  Leu
                    905                      910

Pro  Cys  Leu  Ser  Gln  Ser  Asp  Gly  Ile  Pro  Tyr  Arg
          915                      920

Thr  Val  Ser  Glu  Trp  Leu  Glu  Ser  Ile  Arg  Met  Lys
925                      930                      935
```

| Arg | Tyr | Ile | Leu | His | Phe | His | Ser | Ala | Gly | Leu | Asp |
|-----|-----|-----|-----|-----|-----|-----|-----|-----|-----|-----|-----|
|     |     |     | 940 |     |     |     |     | 945 |     |     |     |

| Thr | Met | Glu | Cys | Val | Leu | Glu | Leu | Thr | Ala | Glu | Asp |
|-----|-----|-----|-----|-----|-----|-----|-----|-----|-----|-----|-----|
|     | 950 |     |     |     |     | 955 |     |     |     |     | 960 |

| Leu | Thr | Gln | Met | Gly | Ile | Thr | Leu | Pro | Gly | His | Gln |
|-----|-----|-----|-----|-----|-----|-----|-----|-----|-----|-----|-----|
|     |     |     |     | 965 |     |     |     |     | 970 |     |     |

| Lys | Arg | Ile | Leu | Cys | Ser | Ile | Gln | Gly | Phe | Lys | Asp |
|-----|-----|-----|-----|-----|-----|-----|-----|-----|-----|-----|-----|
|     |     | 975 |     |     |     |     | 980 |     |     |     |     |

(2) INFORMATION FOR SEQ ID NO: 10:

(i) SEQUENCE CHARACTERISTICS:
        (A) LENGTH: 849
        (B) TYPE: AMINO ACID
        (C) STRANDEDNESS: UNKNOWN
        (D) TOPOLOGY: UNKNOWN (xi) SEQUENCE DESCRIPTION: SEQ ID NO:10:

| Gly | Glu | Ser | Gln | Phe | Ala | Lys | Ile | Asp | Thr | Ile | Ala |
|-----|-----|-----|-----|-----|-----|-----|-----|-----|-----|-----|-----|
| 1   |     |     |     | 5   |     |     |     |     | 10  |     |     |

| Ala | Asp | Glu | Ser | Phe | Thr | Gln | Val | Asp | Ile | Gly | Asp |
|-----|-----|-----|-----|-----|-----|-----|-----|-----|-----|-----|-----|
|     |     | 15  |     |     |     |     | 20  |     |     |     |     |

| Arg | Ile | Met | Lys | Leu | Asn | Thr | Glu | Val | Arg | Asp | Val |
|-----|-----|-----|-----|-----|-----|-----|-----|-----|-----|-----|-----|
| 25  |     |     |     |     | 30  |     |     |     |     | 35  |     |

| Gly | Pro | Leu | Ser | Lys | Lys | Gly | Phe | Tyr | Leu | Ala | Phe |
|-----|-----|-----|-----|-----|-----|-----|-----|-----|-----|-----|-----|
|     |     |     | 40  |     |     |     |     | 45  |     |     |     |

| Gln | Asp | Val | Gly | Ala | Cys | Ile | Ala | Leu | Val | Ser | Val |
|-----|-----|-----|-----|-----|-----|-----|-----|-----|-----|-----|-----|
|     | 50  |     |     |     |     | 55  |     |     |     |     | 60  |

| Arg | Val | Phe | Tyr | Lys | Lys | Cys | Pro | Leu | Thr | Val | Arg |
|-----|-----|-----|-----|-----|-----|-----|-----|-----|-----|-----|-----|
|     |     |     |     | 65  |     |     |     |     | 70  |     |     |

| Asn | Leu | Ala | Gln | Phe | Pro | Asp | Thr | Ile | Thr | Gly | Ala |
|-----|-----|-----|-----|-----|-----|-----|-----|-----|-----|-----|-----|
|     |     | 75  |     |     |     |     | 80  |     |     |     |     |

| Asp | Thr | Ser | Ser | Leu | Val | Glu | Val | Arg | Gly | Ser | Cys |
|-----|-----|-----|-----|-----|-----|-----|-----|-----|-----|-----|-----|
| 85  |     |     |     |     | 90  |     |     |     |     | 95  |     |

| Val | Asn | Asn | Ser | Glu | Glu | Lys | Asp | Val | Pro | Lys | Met |
|-----|-----|-----|-----|-----|-----|-----|-----|-----|-----|-----|-----|
|     |     |     | 100 |     |     |     |     | 105 |     |     |     |

| Tyr | Cys | Gly | Ala | Asp | Gly | Glu | Trp | Leu | Val | Pro | Ile |
|-----|-----|-----|-----|-----|-----|-----|-----|-----|-----|-----|-----|
|     | 110 |     |     |     |     | 115 |     |     |     |     | 120 |

| Gly | Asn | Cys | Leu | Cys | Asn | Ala | Gly | Tyr | Glu | Glu | Arg |
|-----|-----|-----|-----|-----|-----|-----|-----|-----|-----|-----|-----|
|     |     |     |     | 125 |     |     |     |     | 130 |     |     |

| Asn | Gly | Glu | Cys | Gln | Ala | Cys | Lys | Ile | Gly | Tyr | Tyr |
|-----|-----|-----|-----|-----|-----|-----|-----|-----|-----|-----|-----|
|     |     | 135 |     |     |     |     | 140 |     |     |     |     |

| Lys | Ala | Leu | Ser | Thr | Asp | Val | Ala | Cys | Ala | Lys | Cys |
|-----|-----|-----|-----|-----|-----|-----|-----|-----|-----|-----|-----|
| 145 |     |     |     |     | 150 |     |     |     |     | 155 |     |

| Pro | Pro | His | Ser | Tyr | Ser | Ile | Trp | Glu | Gly | Ser | Thr |
|-----|-----|-----|-----|-----|-----|-----|-----|-----|-----|-----|-----|
|     |     |     | 160 |     |     |     |     | 165 |     |     |     |

| Ser | Cys | Thr | Cys | Asp | Arg | Gly | Phe | Phe | Arg | Ala | Glu |
|-----|-----|-----|-----|-----|-----|-----|-----|-----|-----|-----|-----|
|     | 170 |     |     |     |     | 175 |     |     |     |     | 180 |

| Asn | Asp | Ala | Ala | Ser | Met | Pro | Cys | Thr | Arg | Pro | Pro |
|-----|-----|-----|-----|-----|-----|-----|-----|-----|-----|-----|-----|
|     |     |     |     | 185 |     |     |     |     | 190 |     |     |

| Ser | Ala | Pro | Gln | Asn | Leu | Ile | Ser | Asn | Val | Asn | Glu |
|-----|-----|-----|-----|-----|-----|-----|-----|-----|-----|-----|-----|
|     |     | 195 |     |     |     |     | 200 |     |     |     |     |

| Thr | Ser | Val | Asn | Leu | Glu | Trp | Ser | Ala | Pro | Gln | Asn |
|-----|-----|-----|-----|-----|-----|-----|-----|-----|-----|-----|-----|
| 205 |     |     |     |     | 210 |     |     |     |     | 215 |     |

| Lys | Gly | Gly | Arg | Asp | Asp | Ile | Ser | Tyr | Asn | Val | Val |
|-----|-----|-----|-----|-----|-----|-----|-----|-----|-----|-----|-----|
|     |     |     | 220 |     |     |     |     | 225 |     |     |     |

Cys Lys Arg Cys Gly Ala Gly Glu Pro Ser His Cys
230                     235                     240

Arg Ser Cys Gly Ser Gly Val His Phe Ser Pro Gln
            245                 250

Gln Asn Gly Leu Lys Thr Thr Lys Val Ser Ile Thr
            255             260

Asp Leu Leu Ala His Thr Asn Tyr Thr Phe Glu Val
265                 270                 275

Trp Ala Val Asn Gly Val Ser Lys His Asn Pro Ser
            280             285

Gln Asp Gln Ala Val Ser Val Thr Val Thr Thr Asn
290                 295                     300

Gln Ala Ala Pro Ser Pro Ile Ala Leu Ile Gln Ala
                305             310

Lys Glu Ile Thr Arg His Ser Val Ala Leu Ala Trp
        315                 320

Leu Glu Pro Asp Arg Pro Asn Gly Val Ile Leu Glu
325                 330                 335

Tyr Glu Val Lys Tyr Tyr Glu Lys Asp Gln Asn Glu
            340                 345

Arg Thr Tyr Arg Ile Val Lys Thr Ala Ser Arg Asn
350                     355                     360

Thr Asp Ile Lys Gly Leu Asn Pro Leu Thr Ser Tyr
                365                 370

Val Phe His Val Arg Ala Arg Thr Ala Ala Gly Tyr
        375                 380

Gly Asp Phe Ser Gly Pro Phe Glu Phe Thr Thr Asn
385                 390                 395

Thr Val Pro Ser Pro Ile Ile Gly Asp Gly Thr Asn
                400                 405

Pro Thr Val Leu Leu Val Ser Val Ala Gly Ser Val
        410                 415                 420

Val Leu Val Val Ile Leu Ile Ala Ala Phe Val Ile
                425                 430

Ser Arg Arg Arg Ser Lys Tyr Ser Lys Ala Lys Gln
            435                 440

Glu Ala Asp Glu Glu Lys His Leu Asn Gln Gly Val
445                 450                 455

Arg Thr Tyr Val Asp Pro Phe Thr Tyr Glu Asp Pro
            460                 465

Asn Gln Ala Val Arg Glu Phe Ala Lys Glu Ile Asp
470                 475                     480

Ala Ser Cys Ile Lys Ile Glu Lys Val Ile Gly Val
            485                     490

Gly Glu Phe Gly Glu Val Cys Ser Gly Arg Leu Lys
        495                 500

Val Pro Gly Lys Arg Glu Ile Cys Val Ala Ile Lys
505                 510                 515

Thr Leu Lys Ala Gly Tyr Thr Asp Lys Gln Arg Arg
            520                 525

Asp Phe Leu Ser Glu Ala Ser Ile Met Gly Gln Phe
530                 535                     540

Asp His Pro Asn Ile Ile His Leu Glu Gly Val Val

|     |     |     |     |     | 545 |     |     |     | 550 |     |     |
| --- | --- | --- | --- | --- | --- | --- | --- | --- | --- | --- | --- |

Thr Lys Cys Lys Pro Val Met Ile Ile Thr Glu Tyr
        555                 560

Met Glu Asn Gly Ser Leu Asp Ala Phe Leu Arg Lys
565             570                 575

Asn Asp Gly Arg Phe Thr Val Ile Gln Leu Val Gly
            580             585

Met Leu Arg Gly Ile Gly Ser Gly Met Lys Tyr Leu
        590             595                 600

Ser Asp Met Ser Tyr Val His Arg Asp Leu Ala Ala
                605             610

Arg Asn Ile Leu Val Asn Ser Asn Leu Val Cys Lys
            615             620

Val Ser Asp Phe Gly Met Ser Arg Val Leu Glu Asp
625             630             635

Asp Pro Glu Ala Ala Tyr Thr Thr Arg Gly Gly Lys
            640                 645

Ile Pro Ile Arg Trp Thr Ala Pro Glu Ala Ile Ala
        650             655                 660

Tyr Arg Lys Phe Thr Ser Ala Ser Asp Val Trp Ser
            665                 670

Tyr Gly Ile Val Met Trp Glu Val Met Ser Tyr Gly
        675             680

Glu Arg Pro Tyr Trp Asp Met Ser Asn Gln Asp Val
685             690                 695

Ile Lys Ala Ile Glu Glu Gly Tyr Arg Leu Pro Pro
            700                 705

Pro Met Asp Cys Pro Ile Ala Leu His Gln Leu Met
    710                 715                 720

Leu Asp Cys Trp Gln Lys Glu Arg Ser Asp Arg Pro
                725                 730

Lys Phe Gly Gln Ile Val Asn Met Leu Asp Lys Leu
        735                 740

Ile Arg Asn Pro Asn Ser Leu Lys Arg Thr Asp Ser
745             750                 755

Glu Ser Ser Arg Pro Ser Thr Ala Leu Leu Asp Pro
            760                 765

Ser Ser Pro Glu Phe Ser Ala Val Val Ser Val Ser
    770                 775                 780

Asp Trp Leu Gln Ala Ile Lys Met Glu Arg Tyr Lys
                785                 790

Asp Asn Phe Cys Ala Ala Gly Tyr Thr Thr Leu Glu
        795                 800

Ala Val Val His Met Asn Gln Asp Leu Ala Arg
805             810                 815

Ile Gly Ile Thr Ala Ile Thr His Gln Asn Lys Ile
            820                 825

Leu Ser Ser Val Gln Ala Met Arg Ser Gln Met Gln
    830                 835                 840

Gln Met His Gly Arg Met Val Pro Val
                845

(2) INFORMATION FOR SEQ ID NO: 11:

( i ) SEQUENCE CHARACTERISTICS:
  ( A ) LENGTH: 612
  ( B ) TYPE: AMINO ACID
  ( C ) STRANDEDNESS: UNKNOWN
  ( D ) TOPOLOGY: UNKNOWN ( x i ) SEQUENCE DESCRIPTION: SEQ ID NO:11:

```
Val  Arg  Cys  Gly  Asp  Asn  Val  Gln  Phe  Glu  Pro  Arg
 1                    5                        10

Gln  Val  Gly  Leu  Thr  Glu  Ser  Val  Ser  Gln  Val  Ser
          15                   20

Asn  Leu  Leu  Ala  Arg  Val  Gln  Tyr  Thr  Phe  Glu  Ile
 25                      30                        35

Gln  Ala  Val  Asn  Leu  Val  Thr  Glu  Leu  Ser  Ser  Glu
               40                       45

Ala  Pro  Gln  Tyr  Ala  Thr  Ile  Asn  Val  Ser  Thr  Ser
     50                      55                         60

Gln  Ser  Val  Pro  Ser  Ala  Ile  Pro  Met  Met  His  Gln
                    65                        70

Val  Ser  Arg  Ala  Thr  Ser  Ser  Ile  Thr  Leu  Ser  Trp
          75                        80

Pro  Gln  Pro  Asp  Gln  Pro  Asn  Gly  Val  Ile  Leu  Asp
 85                      90                        95

Tyr  Gln  Leu  Arg  Tyr  Phe  Asp  Lys  Ala  Glu  Asp  Glu
               100                      105

Asp  Asn  Ser  Phe  Thr  Leu  Thr  Ser  Glu  Thr  Asn  Met
     110                     115                        120

Ala  Thr  Ile  Leu  Asn  Leu  Ser  Pro  Gly  Lys  Ile  Tyr
                    125                       130

Val  Phe  Gln  Val  Arg  Ala  Arg  Thr  Ala  Val  Gly  Tyr
          135                       140

Gly  Pro  Tyr  Ser  Gly  Lys  Met  Tyr  Phe  Gln  Thr  Leu
145                      150                       155

Met  Gly  Gly  Glu  His  Ser  Glu  Met  Ala  Gln  Asp  Arg
               160                      165

Leu  Pro  Leu  Ile  Val  Gly  Ser  Ala  Leu  Gly  Gly  Leu
     170                     175                        180

Ala  Phe  Leu  Val  Ile  Ala  Ala  Ile  Ala  Ile  Leu  Ala
                    185                       190

Ile  Ile  Phe  Lys  Ser  Lys  Arg  Arg  Glu  Thr  Pro  Tyr
          195                       200

Thr  Asp  Arg  Leu  Gln  Gln  Tyr  Ile  Ser  Thr  Arg  Gly
205                      210                       215

Leu  Gly  Val  Lys  Tyr  Tyr  Ile  Asp  Pro  Ser  Thr  Tyr
               220                      225

Glu  Asp  Pro  Asn  Glu  Ala  Ile  Arg  Glu  Phe  Ala  Lys
     230                     235                        240

Glu  Ile  Asp  Val  Ser  Phe  Ile  Lys  Ile  Glu  Glu  Val
                    245                       250

Ile  Gly  Ser  Gly  Glu  Phe  Gly  Glu  Val  Cys  Phe  Gly
          255                       260

Arg  Leu  Lys  His  Pro  Gly  Lys  Arg  Glu  Tyr  Thr  Val
265                      270                       275

Ala  Ile  Lys  Thr  Leu  Lys  Ser  Gly  Tyr  Thr  Asp  Glu
               280                      285
```

| | | | | | | | | | |
|---|---|---|---|---|---|---|---|---|---|
| Gln | Arg | Arg | Glu | Phe | Leu | Ser | Glu | Ala | Ser | Ile | Met |
| 290 | | | | | 295 | | | | 300 |

Gln Arg Arg Glu Phe Leu Ser Glu Ala Ser Ile Met
290                         295                    300

Gly Gln Phe Glu His Pro Asn Val Ile His Leu Glu
                305                310

Gly Val Val Thr Lys Ser Arg Pro Val Met Ile Val
        315                 320

Thr Glu Phe Met Glu Asn Gly Ser Leu Asp Ser Phe
325                 330                      335

Leu Arg Gln Lys Glu Gly Gln Phe Ser Val Leu Gln
            340                 345

Leu Val Gly Met Leu Arg Gly Ile Ala Ala Gly Met
        350                 355                 360

Arg Tyr Leu Ser Asp Met Asn Tyr Val His Arg Asp
                365                 370

Leu Ala Ala Arg Asn Ile Leu Val Asn Ser Asn Leu
            375                 380

Val Cys Lys Val Ser Asp Phe Gly Leu Ser Arg Phe
385                 390                     395

Leu Glu Asp Asp Ala Ser Asn Pro Thr Tyr Thr Gly
            400                 405

Ala Leu Gly Cys Lys Ile Pro Ile Arg Trp Thr Ala
410                 415                     420

Pro Glu Ala Val Gln Tyr Arg Lys Phe Thr Ser Ser
                425                 430

Ser Asp Val Trp Ser Tyr Gly Ile Val Met Trp Glu
            435                 440

Val Met Ser Tyr Gly Glu Arg Pro Tyr Trp Asp Met
445                 450                     455

Ser Asn Gln Asp Val Ile Asn Ala Ile Asp Gln Asp
            460                 465

Tyr Arg Leu Pro Pro Pro Asp Cys Pro Thr Val
            470                 475             480

Leu His Leu Leu Met Leu Asp Cys Trp Gln Lys Asp
                485                 490

Arg Val Gln Arg Pro Lys Phe Glu Gln Ile Val Ser
        495                 500

Ala Leu Asp Lys Met Ile Arg Lys Pro Ser Ala Leu
505                 510                     515

Lys Ala Thr Gly Thr Gly Ser Ser Arg Pro Ser Gln
            520                 525

Pro Leu Ala Ser Asn Ser Pro Asp Phe Pro Ser
530                 535                     540

Leu Ser Asn Ala His Glu Trp Leu Asp Ala Ile Lys
            545                 550

Met Gly Arg Tyr Lys Glu Asn Phe Asp Gln Ala Gly
        555                 560

Leu Ile Thr Phe Asp Val Ile Ser Arg Met Thr Leu
565                 570                     575

Glu Asp Leu Gln Arg Ile Gly Ile Thr Leu Val Gly
            580                 585

His Gln Lys Lys Ile Leu Asn Ser Ile Gln Leu Met
        590                 595                 600

Lys Val His Leu Asn Gln Leu Glu Pro Val Glu Val
                605                 610

( 2 ) INFORMATION FOR SEQ ID NO: 12:

( i ) SEQUENCE CHARACTERISTICS:
        ( A ) LENGTH: 19
        ( B ) TYPE: AMINO ACID
        ( C ) STRANDEDNESS: UNKNOWN
        ( D ) TOPOLOGY: UNKNOWN ( x i ) SEQUENCE DESCRIPTION: SEQ ID NO:12:

```
Leu  Ser  Arg  Ile  Cys  Thr  Pro  Asp  Val  Ser  Gly  Thr  Val  Gly
 1              5                        10

Ser  Arg  Pro  Ala  Ala
15
```

( 2 ) INFORMATION FOR SEQ ID NO: 13:

( i ) SEQUENCE CHARACTERISTICS:
        ( A ) LENGTH: 490
        ( B ) TYPE: AMINO ACID
        ( C ) STRANDEDNESS: UNKNOWN
        ( D ) TOPOLOGY: UNKNOWN ( x i ) SEQUENCE DESCRIPTION: SEQ ID NO:13:

```
Tyr  Val  Phe  Gln  Ile  Arg  Ala  Arg  Thr  Ala  Ala  Gly
 1              5                        10

Tyr  Gly  Gly  Phe  Ser  Arg  Arg  Phe  Glu  Phe  Glu  Thr
         15                        20

Ser  Pro  Val  Leu  Ala  Ala  Ser  Ser  Asp  Gln  Ser  Gln
25                       30                        35

Ile  Pro  Ile  Ile  Val  Val  Ser  Val  Thr  Val  Gly  Val
              40                        45

Ile  Leu  Leu  Ala  Val  Val  Ile  Gly  Phe  Leu  Leu  Ser
         50                        55                   60

Gly  Ser  Cys  Cys  Asp  His  Gly  Cys  Gly  Trp  Ala  Ser
                   65                        70

Ser  Leu  Arg  Ala  Val  Ala  Tyr  Pro  Ser  Leu  Ile  Trp
              75                        80

Arg  Cys  Gly  Tyr  Ser  Lys  Ala  Lys  Gln  Asp  Pro  Glu
85                       90                        95

Glu  Glu  Lys  Met  His  Phe  His  Asn  Gly  His  Ile  Lys
                   100                       105

Leu  Pro  Gly  Val  Arg  Thr  Tyr  Ile  Asp  Pro  His  Thr
         110                       115                  120

Tyr  Glu  Asp  Pro  Asn  Gln  Ala  Val  His  Glu  Phe  Ala
                   125                       130

Lys  Glu  Ile  Glu  Ala  Ser  Cys  Ile  Thr  Ile  Glu  Arg
              135                       140

Val  Ile  Gly  Ala  Gly  Glu  Phe  Gly  Glu  Val  Cys  Ser
145                      150                       155

Gly  Arg  Leu  Lys  Leu  Gln  Gly  Lys  Arg  Glu  Phe  Pro
              160                       165

Val  Ala  Ile  Lys  Thr  Leu  Lys  Val  Gly  Tyr  Thr  Glu
         170                       175                  180

Lys  Gln  Arg  Arg  Asp  Phe  Leu  Gly  Glu  Ala  Ser  Ile
                   185                       190

Met  Gly  Gln  Phe  Asp  His  Pro  Asn  Ile  Ile  His  Leu
         195                       200
```

| | | | | | | | | | |
|---|---|---|---|---|---|---|---|---|---|
| Glu 205 | Gly | Val | Val | Thr 210 | Lys | Ser | Lys | Pro | Val Met Ile 215 |

Glu Gly Val Val Thr Lys Ser Lys Pro Val Met Ile
205                    210                     215

Val Thr Glu Tyr Met Glu Asn Gly Ser Leu Asp Thr
            220                 225

Phe Leu Lys Lys Asn Asp Gly Gln Phe Thr Val Ile
        230                 235                     240

Gln Leu Val Gly Met Leu Arg Gly Ile Ala Ser Gly
                245                     250

Met Lys Tyr Leu Ser Asp Met Gly Tyr Val His Arg
            255                 260

Asp Leu Ala Ala Arg Asn Ile Leu Ile Asn Ser Asn
265                     270                 275

Leu Val Cys Lys Val Ser Asp Phe Gly Leu Ser Arg
            280                 285

Val Leu Glu Asp Asp Pro Glu Ala Ala Tyr Thr Thr
        290                 295                     300

Arg Gly Gly Lys Ile Pro Ile Arg Trp Thr Ala Pro
                305                     310

Glu Ala Ile Ala Phe Arg Lys Phe Thr Ser Ala Ser
            315                 320

Asp Val Trp Ser Tyr Gly Ile Val Met Trp Glu Val
325                     330                 335

Met Ser Tyr Gly Glu Arg Pro Tyr Trp Glu Met Thr
            340                 345

Asn Gln Asp Val Ile Lys Ala Val Glu Glu Gly Tyr
    350                 355                     360

Arg Leu Pro Ser Pro Met Asp Cys Pro Ala Ala Leu
                365                     370

Tyr Gln Leu Met Leu Asp Cys Trp Gln Lys Asp Arg
        375                 380

Asn Ser Arg Pro Lys Phe Asp Glu Ile Val Ser Met
385                     390                 395

Leu Asp Lys Leu Ile Arg Asn Pro Ser Ser Leu Lys
            400                 405

Thr Leu Val Asn Ala Ser Ser Arg Val Ser Asn Leu
    410                 415                     420

Leu Val Glu His Ser Pro Val Gly Ser Gly Ala Tyr
                425                     430

Arg Ser Val Gly Glu Trp Leu Glu Ala Ile Lys Met
        435                 440

Gly Arg Tyr Thr Glu Ile Phe Met Glu Asn Gly Tyr
445                     450                 455

Ser Ser Met Asp Ser Val Ala Gln Val Thr Leu Glu
            460                 465

Asp Glu Ser Pro Cys Glu Lys Trp Ser Leu Thr Leu
    470                 475                     480

His Pro Leu Phe Pro Thr Gly Tyr Gln Thr
                485                 490

( 2 ) INFORMATION FOR SEQ ID NO: 14:

( i ) SEQUENCE CHARACTERISTICS:
        ( A ) LENGTH: 371
        ( B ) TYPE: AMINO ACID
        ( C ) STRANDEDNESS: UNKNOWN
        ( D ) TOPOLOGY: UNKNOWN ( x i ) SEQUENCE DESCRIPTION: SEQ ID NO:14:

| Ile | Glu | Lys | Ile | Ile | Gly | Ile | Ser | Gly | Glu | Ser | Gly |
| 1 | | | | 5 | | | | | 10 | | |

| Glu | Val | Cys | Tyr | Gly | Arg | Leu | Gln | Val | Pro | Gly | Gln |
| | | 15 | | | | | 20 | | | | |

| Arg | Asp | Val | Pro | Val | Ala | Ile | Lys | Ala | Leu | Lys | Ala |
| 25 | | | | | 30 | | | | | 35 | |

| Gly | Tyr | Thr | Glu | Arg | Gln | Arg | Gln | Asp | Phe | Leu | Arg |
| | | | 40 | | | | | 45 | | | |

| Glu | Ala | Ala | Ile | Met | Gly | Gln | Phe | Asp | His | Pro | Asn |
| | | 50 | | | | 55 | | | | | 60 |

| Ile | Ile | Arg | Leu | Glu | Gly | Val | Val | Thr | Arg | Gly | Arg |
| | | | | 65 | | | | | 70 | | |

| Leu | Ala | Met | Ile | Val | Thr | Glu | Tyr | Met | Glu | Asn | Gly |
| | | 75 | | | | | 80 | | | | |

| Ser | Leu | Asp | Ala | Phe | Leu | Arg | Thr | His | Asp | Gly | Gln |
| 85 | | | | | 90 | | | | | 95 | |

| Phe | Thr | Ile | Leu | Gln | Leu | Val | Gly | Met | Leu | Lys | Gly |
| | | | 100 | | | | | 105 | | | |

| Val | Gly | Ala | Gly | Met | Arg | Tyr | Leu | Ser | Asp | Leu | Gly |
| | 110 | | | | | 115 | | | | | 120 |

| Tyr | Ile | His | Arg | Asp | Leu | Ala | Ala | Arg | Asn | Ile | Leu |
| | | | | 125 | | | | | 130 | | |

| Val | Asp | Gly | Arg | Leu | Val | Cys | Lys | Val | Ser | Asp | Phe |
| | | 135 | | | | | 140 | | | | |

| Gly | Leu | Ser | Arg | Ala | Leu | Glu | Asp | Pro | Glu | Ala |
| 145 | | | | | 150 | | | | | 155 |

| Ala | Tyr | Thr | Thr | Ala | Gly | Gly | Lys | Ile | Pro | Ile | Arg |
| | | | 160 | | | | | 165 | | | |

| Trp | Thr | Ala | Pro | Glu | Ala | Ile | Ala | Phe | Arg | Thr | Phe |
| | 170 | | | | | 175 | | | | | 180 |

| Ser | Ser | Ala | Ser | Asp | Val | Trp | Ser | Phe | Gly | Val | Val |
| | | | | 185 | | | | | 190 | | |

| Met | Trp | Glu | Val | Leu | Ala | Tyr | Gly | Glu | Arg | Pro | Tyr |
| | | 195 | | | | | 200 | | | | |

| Trp | Asn | Met | Thr | Asn | Gln | Asp | Val | Ile | Ser | Ser | Val |
| 205 | | | | | 210 | | | | | 215 | |

| Glu | Glu | Gly | Tyr | Arg | Leu | Pro | Ala | Pro | Met | Gly | Cys |
| | | | 220 | | | | | 225 | | | |

| Pro | Arg | Ala | Leu | His | Gln | Leu | Met | Leu | Asp | Cys | Trp |
| | 230 | | | | | 235 | | | | | 240 |

| His | Lys | Asp | Arg | Ala | Gln | Arg | Pro | Arg | Phe | Ser | His |
| | | | | 245 | | | | | 250 | | |

| Val | Val | Ser | Val | Leu | Glu | Ala | Leu | Val | His | Ser | Pro |
| | | 255 | | | | | 260 | | | | |

| Glu | Ser | Leu | Arg | Ala | Thr | Ala | Thr | Val | Ser | Arg | Cys |
| 265 | | | | | 270 | | | | | 275 | |

| Pro | Ala | Pro | Ala | Phe | Ala | Arg | Ser | Cys | Phe | Asp | Leu |
| | | | 280 | | | | | 285 | | | |

| Arg | Ala | Gly | Gly | Asn | Gly | Asn | Gly | Asp | Leu | Thr | Val |
| | 290 | | | | | 295 | | | | | 300 |

| Gly | Asp | Trp | Leu | Asp | Ser | Ile | Arg | Met | Gly | Arg | Tyr |
| | | | | 305 | | | | | 310 | | |

-continued

| Arg | Arg | Asp 315 | His | Phe | Ala | Ala | Gly 320 | Gly | Tyr | Ser | Ser |
| --- | --- | --- | --- | --- | --- | --- | --- | --- | --- | --- | --- |
| Leu 325 | Gly | Met | Val | Leu | His 330 | Met | Asn | Ala | Gln | Asp 335 | Val |
| Arg | Ala | Leu | Gly 340 | Ile | Thr | Leu | Met | Gly 345 | His | Gln | Lys |
| Lys | Ile 350 | Leu | Gly | Ser | Ile | Gln 355 | Thr | Met | Arg | Ser | Gln 360 |
| Leu | Ser | Cys | Thr | Gln 365 | Gly | Pro | Arg | Arg | His 370 | Leu | |